(12) United States Patent
Dickson

(10) Patent No.: US 10,647,751 B2
(45) Date of Patent: May 12, 2020

(54) PRODUCTION OF LARGE-SIZED MICRODYSTROPHINS IN AN AAV-BASED VECTOR CONFIGURATION

(71) Applicant: ROYAL HOLLOWAY & BEDFORD NEW COLLEGE, Egham Surrey (GB)

(72) Inventor: George Dickson, London (GB)

(73) Assignee: ROYAL HOLLOWAY & BEDFORD NEW COLLEGE, Egham Surrey (GB)

( * ) Notice: Subject to any disclaimer, the term of this patent is extended or adjusted under 35 U.S.C. 154(b) by 79 days.

(21) Appl. No.: 15/571,802

(22) PCT Filed: May 9, 2016

(86) PCT No.: PCT/EP2016/060350
§ 371 (c)(1),
(2) Date: Nov. 3, 2017

(87) PCT Pub. No.: WO2016/177911
PCT Pub. Date: Nov. 10, 2016

(65) Prior Publication Data
US 2018/0346533 A1     Dec. 6, 2018

(30) Foreign Application Priority Data
May 7, 2015   (GB) .................................. 1507842.1

(51) Int. Cl.
| C07K 14/47 | (2006.01) |
| A61K 48/00 | (2006.01) |
| A61P 21/00 | (2006.01) |
| C12N 15/861 | (2006.01) |
| C12N 15/86 | (2006.01) |

(52) U.S. Cl.
CPC ...... *C07K 14/4708* (2013.01); *A61K 48/0058* (2013.01); *A61K 48/0066* (2013.01); *A61P 21/00* (2018.01); *C12N 15/86* (2013.01); *C12N 15/861* (2013.01); *A61K 48/00* (2013.01); *C12N 2750/14143* (2013.01); *C12N 2799/025* (2013.01)

(58) Field of Classification Search
None
See application file for complete search history.

(56) References Cited

U.S. PATENT DOCUMENTS

| 7,892,824 B2 * | 2/2011 | Duan .................. A61K 48/005 435/320.1 |
| 2007/0042462 A1 | 2/2007 | Hildinger |

FOREIGN PATENT DOCUMENTS

WO     WO 2001/83695 A2     11/2001

OTHER PUBLICATIONS

Hakim, et al. (2014) "Systemic gene transfer reveals distinctive muscle transduction profile of tyrosine mutant AAV-1, -6, and -9 in neonatal dogs" Molecular Therapy—Methods & Clinical Development, 1: article 14002, 8 pages long.*
Heller et al., "rAAV mediated gene therapy for Duchenne muscular dystrophy," *2011 OSU Molecular Life Sciences Interdisciplinary Graduate Programs Symposium*, 2 pages (May 2, 2011) URL: http://bioserv.mps.ohio-state.edu/igpsymp/2011/posters.php?number=52, retrieved on Dec. 9, 2015.
International Search Report from parent PCT Application No. PCT/EP2016/060350, 7 pages (dated Aug. 19, 2016).
Koo et al., "Delivery of AAV2/9-microdystrophin gene incorporating Helix 1 the coiled-coli motif in the C-terminal domain of dystrophin improves muscle pathology and restores the level of α 1-syntrophin and α-dystrobrevin in skeletal muscles of *mdx*mice," *Human Gene Therapy*22(11):1379-1388 (Nov. 1, 2011).
Written Opinion from parent PCT Application No. PCT/EP2016/060350, 6 pages (dated Aug. 19, 2016).
Dong et al., "Characterization of genome integrity for oversized recombinant AAV vector," *Molecular Therapy*18(1): 87-92 (E-pub Nov. 10, 2009).
Lai et al., "Evidence for the failure of adeno-associated virus serotype 5 to package a viral genome ≥8.2 kb," *Molecular Therapy*18(1): 75-79 (E-pub Nov. 10, 2009).
Wu et al., "Effect of genome size on AAV vector packaging," *Molecular Therapy*18(1): 80-86 (E-pub Nov. 10, 2009).

* cited by examiner

*Primary Examiner* — Robert M Kelly
(74) *Attorney, Agent, or Firm* — Klarquist Sparkman, LLP

(57) ABSTRACT

An adeno-associated viral (AAV) vector containing an expression construct, wherein: the expression construct comprises a nucleic acid sequence which encodes a microdystrophin (MD); and the nucleic acid sequence encoding the MD has a size of at least 4.1 kb.

19 Claims, 13 Drawing Sheets

Specification includes a Sequence Listing.

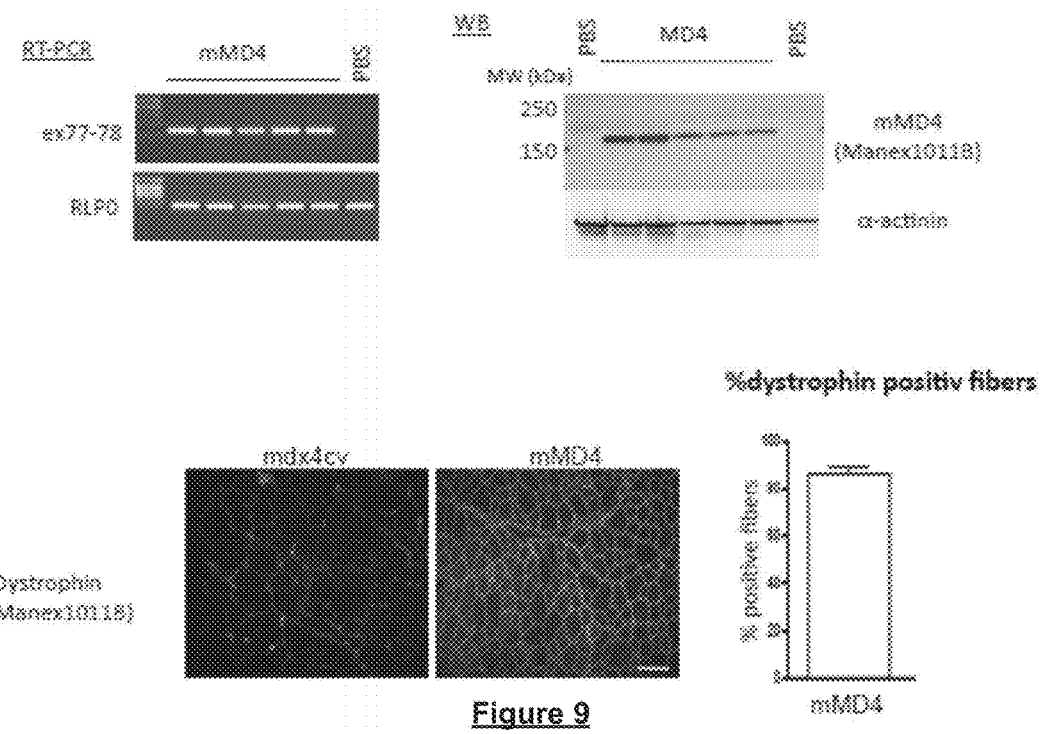
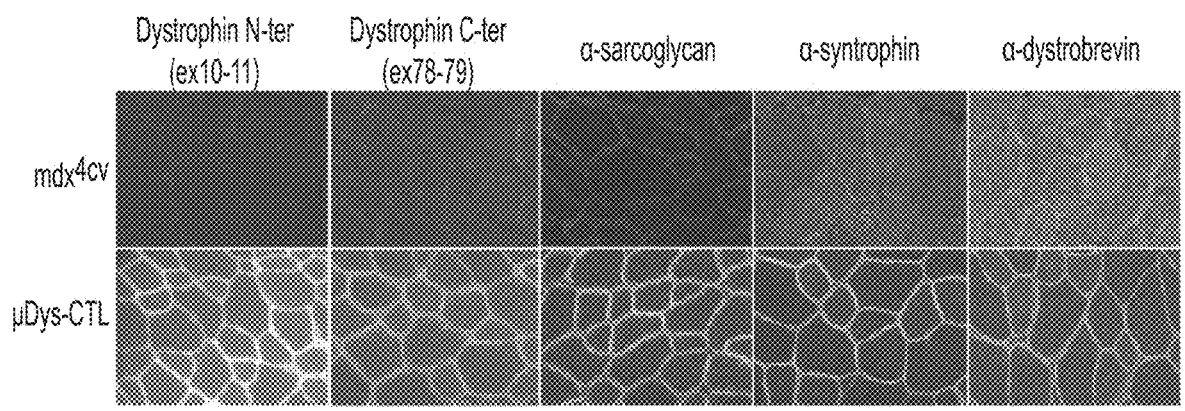
Figure 9
Figure 10A
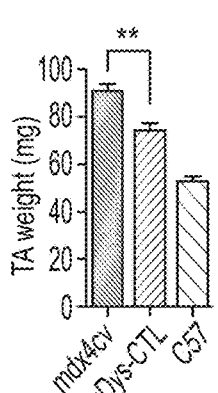
Figure 10B
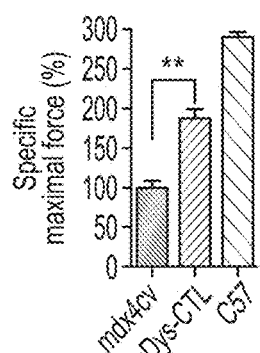
Figure 10C
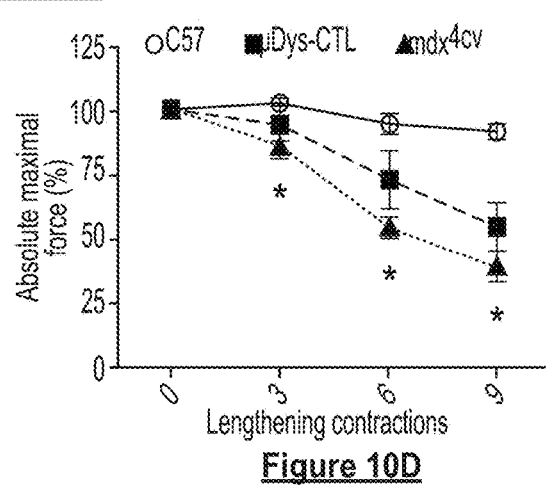
Figure 10D

|  | cMD1 | cMD2 | cMD3 | cMD4 |
|---|---|---|---|---|
| Dys+fibres/total fibres | 83.6% (2514/3008) | 0% | 36.5% (1233/3378) | 26.5% (798/3004) |

SEQUENCE LISTING

<160> NUMBER OF SEQ ID NOS: 18

<210> SEQ ID NO 1
<211> LENGTH: 1394
<212> TYPE: PRT
<213> ORGANISM: Artificial Sequence
<220> FEATURE:
<223> OTHER INFORMATION: murine MD3 (PRT)

<400> SEQUENCE: 1

Met Leu Trp Trp Glu Glu Val Glu Asp Cys Tyr Glu Arg Glu Asp Val
1               5                   10                  15

Gln Lys Lys Thr Phe Thr Lys Trp Ile Asn Ala Gln Phe Ser Lys Phe
            20                  25                  30

Gly Lys Gln His Ile Asp Asn Leu Phe Ser Asp Leu Gln Asp Gly Lys
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Lys Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Thr Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Ser Ser Trp Ser Asp Gly Leu Ala Leu Asn Ala Leu Ile His Ser His
                165                 170                 175

Arg Pro Asp Leu Phe Asp Trp Asn Ser Val Val Ser Gln His Ser Ala
            180                 185                 190

Thr Gln Arg Leu Glu His Ala Phe Asn Ile Ala Lys Cys Gln Leu Gly
        195                 200                 205

Ile Glu Lys Leu Leu Asp Pro Glu Asp Val Ala Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Thr Ser Ser Lys Val Thr Arg Glu Glu His Phe Gln Leu His His Gln
            260                 265                 270

Met His Tyr Ser Gln Gln Ile Thr Val Ser Leu Ala Gln Gly Tyr Glu
        275                 280                 285

Gln Thr Ser Ser Pro Lys Pro Arg Phe Lys Ser Tyr Ala Phe Thr
    290                 295                 300

Gln Ala Ala Tyr Val Ala Thr Ser Asp Ser Thr Gln Ser Pro Tyr Pro
305                 310                 315                 320

Ser Gln His Leu Glu Ala Pro Arg Asp Lys Ser Leu Asp Ser Ser Leu
                325                 330                 335

Met Glu Thr Glu Val Asn Leu Asp Ser Tyr Gln Thr Ala Leu Glu Glu
            340                 345                 350

Val Leu Ser Trp Leu Leu Ser Ala Glu Asp Thr Leu Arg Ala Gln Gly

-continued

```
                355                 360                 365
Glu Ile Ser Asn Asp Val Glu Val Lys Glu Gln Phe His Ala His
    370                 375                 380
Glu Gly Phe Met Met Asp Leu Thr Ser His Gln Gly Leu Val Gly Asn
385                 390                 395                 400
Val Leu Gln Leu Gly Ser Gln Leu Val Gly Lys Gly Lys Leu Ser Glu
                405                 410                 415
Asp Glu Glu Ala Glu Val Gln Glu Gln Met Asn Leu Leu Asn Ser Arg
            420                 425                 430
Trp Glu Cys Leu Arg Val Ala Ser Met Glu Lys Gln Ser Lys Leu His
            435                 440                 445
Lys Val Leu Met Asp Leu Gln Asn Gln Lys Leu Lys Glu Leu Asp Asp
    450                 455                 460
Trp Leu Thr Lys Thr Glu Glu Arg Thr Lys Met Glu Glu Pro
465                 470                 475                 480
Phe Gly Pro Asp Leu Glu Asp Leu Lys Cys Gln Val Gln Gln His Lys
                485                 490                 495
Val Leu Gln Glu Asp Leu Glu Gln Glu Gln Val Arg Val Asn Ser Leu
            500                 505                 510
Thr His Met Val Val Val Asp Glu Ser Ser Gly Asp His Ala Thr
            515                 520                 525
Ala Ala Leu Glu Glu Gln Leu Lys Val Leu Gly Asp Arg Trp Ala Asn
    530                 535                 540
Ile Cys Arg Trp Thr Glu Asp Arg Trp Ile Val Leu Gln Asp Ile Leu
545                 550                 555                 560
Leu Lys Trp Gln His Phe Thr Glu Gln Cys Leu Phe Ser Thr Trp
                565                 570                 575
Leu Ser Glu Lys Glu Asp Ala Met Lys Asn Ile Gln Thr Ser Gly Phe
            580                 585                 590
Lys Asp Gln Asn Glu Met Met Ser Ser Leu His Lys Ile Ser Thr Leu
            595                 600                 605
Lys Ile Asp Leu Glu Lys Lys Lys Pro Thr Met Glu Lys Leu Ser Ser
    610                 615                 620
Leu Asn Gln Asp Leu Leu Ser Ala Leu Lys Asn Lys Ser Val Thr Gln
625                 630                 635                 640
Lys Met Glu Ile Trp Met Glu Asn Phe Ala Gln Arg Trp Asp Asn Leu
                645                 650                 655
Thr Gln Lys Leu Glu Lys Ser Ser Ala Gln Ile Ser Gln Ala Val Thr
            660                 665                 670
Thr Thr Gln Pro Ser Leu Thr Gln Thr Thr Val Met Glu Thr Val Thr
            675                 680                 685
Met Val Thr Thr Arg Glu Gln Ile Met Val Lys His Ala Gln Glu Glu
    690                 695                 700
Leu Pro Pro Pro Pro Gln Lys Lys Arg Gln Ile Thr Val Asp Ala
705                 710                 715                 720
Leu Glu Arg Leu Gln Glu Leu Gln Glu Ala Ala Asp Glu Leu Asp Leu
                725                 730                 735
Lys Leu Arg Gln Ala Glu Val Ile Lys Gly Ser Trp Gln Pro Val Gly
            740                 745                 750
Asp Leu Leu Ile Asp Ser Leu Gln Asp His Leu Glu Lys Val Lys Ala
            755                 760                 765
Leu Arg Gly Glu Ile Ala Pro Leu Lys Glu Asn Val Asn Arg Val Asn
    770                 775                 780
```

-continued

```
Asp Leu Ala His Gln Leu Thr Thr Leu Gly Ile Gln Leu Ser Pro Tyr
785                 790                 795                 800

Asn Leu Ser Thr Leu Glu Asp Leu Asn Thr Arg Trp Arg Leu Leu Gln
            805                 810                 815

Val Ala Val Glu Asp Arg Val Arg Gln Leu His Glu Ala His Arg Asp
        820                 825                 830

Phe Gly Pro Ala Ser Gln His Phe Leu Ser Thr Ser Val Gln Gly Pro
    835                 840                 845

Trp Glu Arg Ala Ile Ser Pro Asn Lys Val Pro Tyr Tyr Ile Asn His
850                 855                 860

Glu Thr Gln Thr Thr Cys Trp Asp His Pro Lys Met Thr Glu Leu Tyr
865                 870                 875                 880

Gln Ser Leu Ala Asp Leu Asn Asn Val Arg Phe Ser Ala Tyr Arg Thr
            885                 890                 895

Ala Met Lys Leu Arg Arg Leu Gln Lys Ala Leu Cys Leu Asp Leu Leu
        900                 905                 910

Ser Leu Ser Ala Ala Cys Asp Ala Leu Asp Gln His Asn Leu Lys Gln
    915                 920                 925

Asn Asp Gln Pro Met Asp Ile Leu Gln Ile Ile Asn Cys Leu Thr Thr
930                 935                 940

Ile Tyr Asp Arg Leu Glu Gln Glu His Asn Asn Leu Val Asn Val Pro
945                 950                 955                 960

Leu Cys Val Asp Met Cys Leu Asn Trp Leu Leu Asn Val Tyr Asp Thr
            965                 970                 975

Gly Arg Thr Gly Arg Ile Arg Val Leu Ser Phe Lys Thr Gly Ile Ile
        980                 985                 990

Ser Leu Cys Lys Ala His Leu Glu Asp Lys Tyr Arg Tyr Leu Phe Lys
    995                 1000                1005

Gln Val Ala Ser Ser Thr Gly Phe Cys Asp Gln Arg Arg Leu Gly Leu
    1010                1015                1020

Leu Leu His Asp Ser Ile Gln Ile Pro Arg Gln Leu Gly Glu Val Ala
1025                1030                1035                1040

Ser Phe Gly Gly Ser Asn Ile Glu Pro Ser Val Arg Ser Cys Phe Gln
        1045                1050                1055

Phe Ala Asn Asn Lys Pro Glu Ile Glu Ala Ala Leu Phe Leu Asp Trp
        1060                1065                1070

Met Arg Leu Glu Pro Gln Ser Met Val Trp Leu Pro Val Leu His Arg
        1075                1080                1085

Val Ala Ala Ala Glu Thr Ala Lys His Gln Ala Lys Cys Asn Ile Cys
        1090                1095                1100

Lys Glu Cys Pro Ile Ile Gly Phe Arg Tyr Arg Ser Leu Lys His Phe
1105                1110                1115                1120

Asn Tyr Asp Ile Cys Gln Ser Cys Phe Phe Ser Gly Arg Val Ala Lys
            1125                1130                1135

Gly His Lys Met His Tyr Pro Met Val Glu Tyr Cys Thr Pro Thr Thr
        1140                1145                1150

Ser Gly Glu Asp Val Arg Asp Phe Ala Lys Val Leu Lys Asn Lys Phe
    1155                1160                1165

Arg Thr Lys Arg Tyr Phe Ala Lys His Pro Arg Met Gly Tyr Leu Pro
    1170                1175                1180

Val Gln Thr Val Leu Glu Gly Asp Asn Met Glu Thr Pro Val Thr Leu
1185                1190                1195                1200
```

```
Ile Asn Phe Trp Pro Val Asp Ser Ala Pro Ala Ser Ser Pro Gln Leu
             1205                1210                1215

Ser His Asp Asp Thr His Ser Arg Ile Glu His Tyr Ala Ser Arg Leu
        1220                1225                1230

Ala Glu Met Glu Asn Ser Asn Gly Ser Tyr Leu Asn Asp Ser Ile Ser
    1235                1240                1245

Pro Asn Glu Ser Ile Asp Asp Glu His Leu Leu Ile Gln His Tyr Cys
1250                1255                1260

Gln Ser Leu Asn Gln Asp Ser Pro Leu Ser Gln Pro Arg Ser Pro Ala
1265                1270                1275                1280

Gln Ile Leu Ile Ser Leu Glu Ser Glu Glu Arg Gly Glu Leu Glu Arg
             1285                1290                1295

Ile Leu Ala Asp Leu Glu Glu Glu Asn Arg Asn Leu Gln Ala Glu Tyr
        1300                1305                1310

Asp Arg Leu Lys Gln Gln His Glu His Lys Gly Leu Ser Pro Leu Pro
    1315                1320                1325

Ser Pro Pro Glu Met Met Pro Thr Ser Pro Gln Ser Pro Arg Asp Ala
    1330                1335                1340

Glu Leu Ile Ala Glu Ala Lys Leu Leu Arg Gln His Lys Gly Arg Leu
1345                1350                1355                1360

Glu Ala Arg Met Gln Ile Leu Glu Asp His Asn Lys Gln Leu Glu Ser
             1365                1370                1375

Gln Leu His Arg Leu Arg Gln Leu Leu Glu Gln Pro Gln Ala Glu Asp
        1380                1385                1390

Thr Met
```

<210> SEQ ID NO 2
<211> LENGTH: 4191
<212> TYPE: DNA
<213> ORGANISM: Artificial Sequence
<220> FEATURE:
<223> OTHER INFORMATION: murine MD3 (cDNA)

<400> SEQUENCE: 2

```
atgctgtggt gggaggaagt ggaggactgc tacgagagag aggacgtgca gaagaaaacc      60
ttcaccaagt ggatcaacgc ccagttcagc aagttcggca agcagcacat cgacaacctg     120
ttcagcgacc tgcaggacgg caagagactg ctggatctgc tggagggact gaccggccag     180
aagctgccca aggagaaggg cagcaccaga gtgcacgccc tgaacaacgt gaacaaggcc     240
ctgagagtgc tgcagaagaa caacgtggac ctggtgaata tcggcagcac cgacatcgtg     300
gacggcaacc acaagctgac cctgggcctg atctggaaca tcatcctgca ctggcaggtg     360
aagaacgtga tgaaaaccat catggccggc ctgcagcaga ccaacagcga aagatcctg     420
ctgagctggg tgaggcagag caccagaaac taccccagg tgaacgtgat caacttcacc     480
agcagctgga gcgacggcct ggccctgaac gccctgatcc acagccacag acccgacctg     540
ttcgactgga cagcgtggt gtcccagcac agcgccaccc agagactgga gcacgccttc     600
aacatcgcca gtgccagct gggcatcgag aagctgctgg accccgagga cgtggccacc     660
acctacccg acaagaaaag catcctcatg tatatcacct ctctgtttca ggtgctgccc     720
cagcaggtgt ccatcgaggc catccaggaa gtggaaatgc tgccccggac cagcagcaaa     780
gtgacccggg aggagcactt ccagctgcac caccagatgc actatagcca gcagatcacc     840
gtgtccctgg cccagggcta cgagcagacc agcagctccc ccaagccag attcaagagc     900
tacgccttca cccaggccgc ctacgtggcc acaagcgata gcacccagag cccctacccc     960
```

```
agccagcacc tggaggcccc tagagacaag agcctggaca gcagcctgat ggagacagaa    1020
gtgaacctgg acagctacca gaccgccctg gaggaagtgc tgtcttggct gctgtccgcc    1080
gaggacaccc tgagagccca gggcgagatc agcaacgacg tggaagaagt gaaggagcag    1140
ttccacgccc acgagggctt catgatggac ctgacctccc atcagggcct ggtgggcaac    1200
gtgctgcagc tgggcagcca gctcgtggga aagggcaagc tgagcgagga cgaggaggcc    1260
gaagtgcagg aacagatgaa cctgctgaac agcagatggg agtgcctgag agtggccagc    1320
atggagaagc agagcaagct gcacaaagtg ctgatggatc tgcagaacca gaagctgaag    1380
gaactggacg actggctgac caagaccgag gagcggacca agaagatgga ggaggagccc    1440
ttcggccccg acctggagga cctgaagtgc caggtgcagc agcataaggt cctgcaggag    1500
gacctggaac aggagcaggt gcgcgtgaac agcctgaccc acatggtggt cgtggtggac    1560
gagagcagcg gcgaccacgc cacagccgcc ctggaagagc agctgaaagt gctgggcgac    1620
agatgggcca atatctgccg gtggaccgag gatagatgga tcgtgctgca ggacatcctg    1680
ctgaagtggc agcacttcac cgaggagcag tgcctgttta gcacctggct gagcgagaaa    1740
gaggacgcca tgaagaacat ccagaccagc ggcttcaagg accagaacga gatgatgagc    1800
agcctgcaca agatcagcac cctgaagatc gacctggaga agaaaaagcc cacaatggag    1860
aagctgtcca gcctgaacca ggacctgctg agcgccctga gaacaagag cgtgacccag    1920 aaaatggaga tctggatgga gaatttcgca cagaggtggg acaacctgac ccagaagctg    1980
gagaagagca gcgcccagat cagccaggcc gtgaccacca cccagcccag cctgacacag    2040
accaccgtga tggagaccgt gaccatggtg accacccggg agcagatcat ggtgaagcac    2100
gcccaggagg agctgccccc tccccccct cagaagaagc ggcagatcac agtggatgcc    2160
ctggagagac tgcaggagct gcaggaagcc gccgacgagc tggatctgaa gctgagacag    2220
gccgaagtga tcaagggcag ctggcagcct gtgggcgatc tgctgatcga cagcctgcag    2280
gaccacctgg agaaagtgaa ggccctgcgg ggcgagatcg cccccctgaa ggagaacgtg    2340
aaccgcgtga cgacctggc ccatcagctg accaccctgg gcattcagct gagcccctac    2400
aacctgagca ccctggagga tctgaacacc cggtggagac tgctgcaggt ggccgtggag    2460
gatagagtga ggcagctgca cgaggcccac agagacttcg gccctgcctc ccagcacttc    2520
ctgagcacca gcgtgcaggg ccctgggag agagccatca gccccaacaa agtgccctac    2580
tacatcaacc acgagaccca gaccacctgc tgggaccacc ctaagatgac cgagctgtac    2640
cagagcctgg ccgacctgaa caatgtgcgg ttcagcgcct acagaaccgc catgaagctg    2700
cggagactgc agaaggccct gtgcctggac ctgctgtccc tgagcgccgc ctgcgacgcc    2760
ctggaccagc acaacctgaa gcagaacgac cagcccatgg atatcctgca gatcatcaac    2820
tgcctgacca ccatctacga tcggctggag caggagcaca acaacctggt gaacgtgccc    2880
ctgtgcgtgg acatgtgcct gaattggctg ctgaacgtgt acgacaccgg caggaccggc    2940
agaatcagag tgctgtcctt caagaccggc atcatcagcc tgtgcaaggc ccacctggag    3000
gataagtacc gctacctgtt caagcaggtg gccagcagca ccggcttctg cgatcagagg    3060
agactgggcc tgctgctgca cgatagcatc cagatcccta ggcagctggg cgaggtggcc    3120
agcttcggcg gcagcaacat cgagcccagc gtgcggagct gcttccagtt cgccaacaac    3180
aagcccgaga tcgaggccgc cctgttcctg gactggatgc ggctggaacc ccagagcatg    3240
gtctggctgc ccgtgctgca cagagtggct gccgccgaga ccgccaagca ccaggccaag    3300
```

| | |
|---|---|
| tgcaacatct gcaaagagtg ccccatcatc ggcttccggt acagaagcct gaagcacttc | 3360 |
| aactacgaca tctgccagag ctgctttttc agcggcagag tggccaaggg ccacaagatg | 3420 |
| cactacccca tggtggagta ctgcaccccc accacctccg gcgaggacgt gcgggacttc | 3480 |
| gccaaggtgc tgaagaacaa gttccggacc aagcggtact tgccaagca cccccggatg | 3540 |
| ggctacctgc ccgtgcagac cgtgctggaa ggcgacaaca tggaaacccc cgtgaccctg | 3600 |
| atcaacttct ggcccgtgga cagcgcccct gccagcagcc cccagctgtc ccacgacgac | 3660 |
| acccacagcc ggatcgagca ctacgccagc cggctcgccg agatggaaaa cagcaacggc | 3720 |
| agctacctga cgacagcat cagccccaac gagagcatcg acgacgagca cctgctgatc | 3780 |
| cagcactact gtcagagcct gaaccaggac agccccctga ccagcccag aagccctgcc | 3840 |
| cagatcctga tcagcctgga aagcgaggaa cggggcgagc tggaacggat cctggccgac | 3900 |
| ctggaagagg aaaaccggaa cctgcaggcc gagtacgacc ggctgaagca gcagcacgag | 3960 |
| cacaagggcc tgagccccct gcccagcccc cctgagatga tgcccacctc ccccagagc | 4020 |
| cccagggacg ccgagctgat cgccgaggcc aagctgctgc ggcagcacaa ggggcggctg | 4080 |
| gaagcccgga tgcagatcct ggaagatcac aacaagcagc tggaaagcca gctgcaccgg | 4140 |
| ctgagacagc tgctggaaca gccccaggcc gaggacacca tgtgatgatg a | 4191 |

<210> SEQ ID NO 3
<211> LENGTH: 5283
<212> TYPE: DNA
<213> ORGANISM: Artificial Sequence
<220> FEATURE:
<223> OTHER INFORMATION: AAV ITR mMD3

<400> SEQUENCE: 3

| | |
|---|---|
| aggaacccct agtgatggag ttggccactc cctctctgcg cgctcgctcg ctcactgagg | 60 |
| ccgcccgggc aaagcccggg cgtcgggcga cctttggtcg cccggcctca gtgagcgagc | 120 |
| gagcgcgcag agagggagtg gccaactcca tcactagggg ttccttgtag ttaatgatta | 180 |
| acccgccatg ctacttatct acgtagccat gctctagaca tggctcgaca gatcgagctc | 240 |
| caccgcggtg gcggccgtcc gccctcggca ccatcctcac gacacccaaa tatggcgacg | 300 |
| ggtgaggaat ggtggggagt tattttttaga gcggtgagga aggtgggcag gcagcaggtg | 360 |
| ttggcgctct aaaaataact cccgggagtt atttttagag cggaggaatg gtggacaccc | 420 |
| aaatatggcg acggttcctc acccgtcgcc atatttgggt gtccgccctc ggccggggcc | 480 |
| gcattcctgg gggccgggcg gtgctcccgc ccgcctcgat aaaaggctcc ggggccggcg | 540 |
| gcggcccacg agctacccgg aggagcggga ggcgccaagc tctagaacta gtggatcccc | 600 |
| cgggctgcag gaattcgcca ccatgctgtg gtgggaggaa gtggaggact gctacgagag | 660 |
| agaggacgtg cagaagaaaa ccttcaccaa gtggatcaac gcccagttca gcaagttcgg | 720 |
| caagcagcac atcgacaacc tgttcagcga cctgcaggac ggcaagagac tgctggatct | 780 |
| gctggagggga ctgaccggcc agaagctgcc caaggagaag gcagcacca gagtgcacgc | 840 |
| cctgaacaac gtgaacaagg ccctgagagt gctgcagaag aacaacgtgg acctggtgaa | 900 |
| tatcggcagc accgacatcg tggacggcaa ccacaagctg accctgggcc tgatctggaa | 960 |
| catcatcctg cactggcagg tgaagaacgt gatgaaaacc atcatggccg gcctgcagca | 1020 |
| gaccaacagc gagaagatcc tgctgagctg ggtgaggcag agcaccagaa actaccccca | 1080 |
| ggtgaacgtg atcaacttca ccagcagctg gagcgacggc ctggccctga acgccctgat | 1140 |
| ccacagccac agacccgacc tgttcgactg gaacagcgtg gtgtcccagc acagcgccac | 1200 |

```
ccagagactg gagcacgcct tcaacatcgc caagtgccag ctgggcatcg agaagctgct    1260
ggaccccgag gacgtggcca ccacctaccc cgacaagaaa agcatcctca tgtatatcac    1320
ctctctgttt caggtgctgc cccagcaggt gtccatcgag gccatccagg aagtggaaat    1380
gctgccccgg accagcagca aagtgacccg ggaggagcac ttccagctgc accaccagat    1440
gcactatagc cagcagatca ccgtgtccct ggcccagggc tacgagcaga ccagcagctc    1500 cccccaagccc agattcaaga gctacgcctt caccccaggcc gcctacgtgg ccacaagcga    1560
tagcacccag agcccctacc ccagccagca cctggaggcc cctagagaca gagcctgga    1620 cagcagcctg atggagacag aagtgaacct ggacagctac cagaccgccc tggaggaagt    1680
gctgtcttgg ctgctgtccg ccgaggacac cctgagagcc cagggcgaga tcagcaacga    1740
cgtggaagaa gtgaaggagc agttccacgc ccacgagggt ttcatgatgg acctgacctc    1800
ccatcagggc ctggtgggca acgtgctgca gctgggcagc cagctcgtgg aaagggcaa    1860 gctgagcgag gacgaggagg ccgaagtgca ggaacagatg aacctgctga cagcagatg    1920 ggagtgcctg agagtggcca gcatggagaa gcagagcaag ctgcacaaag tgctgatgga    1980
tctgcagaac cagaagctga aggaactgga cgactggctg accaagaccg aggagcggac    2040
caagaagatg gaggaggagc ccttcggccc cgacctggag gacctgaagt gccaggtgca    2100
gcagcataag gtcctgcagg aggacctgga acaggagcag gtgcgcgtga acagcctgac    2160
ccacatggtg gtcgtggtgg acgagagcag cggcgaccac gccacagccg ccctggaaga    2220
gcagctgaaa gtgctgggcg acagatgggc caatatctgc cggtggaccg aggatagatg    2280
gatcgtgctg caggacatcc tgctgaagtg gcagcacttc accgaggagc agtgcctgtt    2340
tagcacctgg ctgagcgaga aagaggacgc catgaagaac atccagacca gcggcttcaa    2400
ggaccagaac gagatgatga gcagcctgca caagatcagc accctgaaga tcgacctgga    2460
gaagaaaaag cccacaatgg agaagctgtc cagcctgaac caggacctgc tgagcgccct    2520
gaagaacaag agcgtgaccc cagaaaatgga gatctggatg gagaatttcg cacagaggtg    2580
ggacaacctg acccagaagc tggagaagag cagcgcccag atcagccagg ccgtgaccac    2640
cacccagccc agcctgacac agaccaccgt gatggagacc gtgaccatgg tgaccacccg    2700
ggagcagatc atggtgaagc acgcccagga ggagctgccc cctcccccc ctcagaagaa    2760 gcggcagatc acagtggatg ccctggagag actgcaggag ctgcaggaag ccgccgacga    2820
gctggatctg aagctgagac aggccgaagt gatcaagggc agctggcagc ctgtgggcga    2880
tctgctgatc gacagcctgc aggaccaccct ggagaaagtg aaggcctgc ggggcgagat    2940 cgccccctg aaggagaacg tgaaccgcgt gaacgacctg gcccatcagc tgaccaccct    3000
gggcattcag ctgagcccct acaacctgag cacccctggag gatctgaaca cccggtggag    3060
actgctgcag gtggccgtgg aggatagagt gaggcagctg cacgaggccc acagagactt    3120
cggccctgcc tccagcacct tcctgagcac cagcgtgcag ggcccctggg agagagccat    3180
cagccccaac aaagtgccct actacatcaa ccacgagacc cagaccacct gctgggacca    3240
ccctaagatg accgagctgt accagagcct ggccgacctg aacaatgtgc ggttcagcgc    3300
ctacagaacc gccatgaagc tgcggagact gcagaaggcc ctgtgcctgg acctgctgtc    3360
cctgagcgcc gcctgcgacg ccctggacca gcacaacctg aagcagaacg accagcccat    3420
ggatatcctg cagatcatca actgcctgac caccatctac gatcggctgg agcaggagca    3480
caacaacctg gtgaacgtgc ccctgtgcgt ggacatgtgc ctgaattggc tgctgaacgt    3540
```

-continued

| | |
|---|---|
| gtacgacacc ggcaggaccg gcagaatcag agtgctgtcc ttcaagaccg gcatcatcag | 3600 |
| cctgtgcaag gcccacctgg aggataagta ccgctacctg ttcaagcagg tggccagcag | 3660 |
| caccggcttc tgcgatcaga ggagactggg cctgctgctg cacgatagca tccagatccc | 3720 |
| taggcagctg ggcgaggtgg ccagcttcgg cggcagcaac atcgagccca gcgtgcggag | 3780 |
| ctgcttccag ttcgccaaca caagcccga gatcgaggcc gccctgttcc tggactggat | 3840 |
| gcggctggaa ccccagagca tggtctggct gcccgtgctg cacagagtgg ctgccgccga | 3900 |
| gaccgccaag caccaggcca gtgcaacat ctgcaaagag tgccccatca tcggcttccg | 3960 |
| gtacagaagc ctgaagcact tcaactacga catctgccag agctgctttt tcagcggcag | 4020 |
| agtggccaag ggccacaaga tgcactaccc catggtggag tactgcaccc ccaccacctc | 4080 |
| cggcgaggac gtgcgggact cgccaaggt gctgaagaac aagttccgga ccaagcggta | 4140 |
| ctttgccaag cacccccgga tgggctacct gcccgtgcag accgtgctgg aaggcgacaa | 4200 |
| catggaaacc cccgtgaccc tgatcaactt ctggcccgtg acagcgccc tgccagcag | 4260 |
| cccccagctg tcccacgacg acacccacag ccggatcgag cactacgcca gcggctcgc | 4320 |
| cgagatggaa aacagcaacg gcagctacct gaacgacagc atcagccccca acgagagcat | 4380 |
| cgacgacgag cacctgctga tccagcacta ctgtcagagc ctgaaccagg acagccccct | 4440 |
| gagccagccc agaagccctg cccagatcct gatcagcctg aaagcgagg aacggggcga | 4500 |
| gctggaacga atcctggccg acctggaaga ggaaaaccgg aacctgcagg ccgagtacga | 4560 |
| ccggctgaag cagcagcacg agcacaaggg cctgagcccc ctgcccagcc ccctgagat | 4620 |
| gatgccacc tcccccagaa gccccaggga cgccgagctg atcgccgagg ccaagctgct | 4680 |
| gcggcagcac aagggcggc tggaagcccg gatgcagatc ctggaagatc acaacaagca | 4740 |
| gctgaaagc cagctgcacc ggctgagaca gctgctggaa cagccccagg ccgaggacac | 4800 |
| catgtgatga tgagcggccg cttccctta gtgagggtta atgcttcgag cagacatgat | 4860 |
| aagatacatt gatgagtttg gacaaaccac aactagaatg cagtgaaaaa aatgctttat | 4920 |
| ttgtgaaatt tgtgatgcta ttgctttatt tgtaaccatt ataagctgca ataaacaagt | 4980 |
| taacaacaac aattgcattc attttatgtt tcaggttcag ggggagatgt gggaggtttt | 5040 |
| ttaaagcaag taaaacctct acaaatgtgg taaaatccga taaggactag agcatggcta | 5100 |
| cgtagataag tagcatggcg ggttaatcat taactacaag gaaccctag tgatggagtt | 5160 |
| ggccactccc tctctgcgcg ctcgctcgct cactgaggcc gcccgggcaa agcccgggcg | 5220 |
| tcgggcgacc tttggtcgcc cggcctcagt gagcgagcga gcgcgcagag agggagtggc | 5280 |
| caa | 5283 |

<210> SEQ ID NO 4
<211> LENGTH: 1473
<212> TYPE: PRT
<213> ORGANISM: Artificial Sequence
<220> FEATURE:
<223> OTHER INFORMATION: murine MD4 (PRT)

<400> SEQUENCE: 4

Met Leu Trp Trp Glu Glu Val Glu Asp Cys Tyr Glu Arg Glu Asp Val
1               5                   10                  15

Gln Lys Lys Thr Phe Thr Lys Trp Ile Asn Ala Gln Phe Ser Lys Phe
            20                  25                  30

Gly Lys Gln His Ile Asp Asn Leu Phe Ser Asp Leu Gln Asp Gly Lys
        35                  40                  45

-continued

```
Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
 65              70                  75                  80

Leu Arg Val Leu Gln Lys Asn Asn Val Asp Leu Val Asn Ile Gly Ser
                 85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Thr Ile Met
        115                 120                 125

Ala Gly Leu Gln Gln Thr Asn Ser Glu Lys Ile Leu Leu Ser Trp Val
130                 135                 140

Arg Gln Ser Thr Arg Asn Tyr Pro Gln Val Asn Val Ile Asn Phe Thr
145                 150                 155                 160

Ser Ser Trp Ser Asp Gly Leu Ala Leu Asn Ala Leu Ile His Ser His
                165                 170                 175

Arg Pro Asp Leu Phe Asp Trp Asn Ser Val Val Ser Gln His Ser Ala
            180                 185                 190

Thr Gln Arg Leu Glu His Ala Phe Asn Ile Ala Lys Cys Gln Leu Gly
        195                 200                 205

Ile Glu Lys Leu Leu Asp Pro Glu Asp Val Ala Thr Thr Tyr Pro Asp
210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Thr Ser Ser Lys Val Thr Arg Glu Glu His Phe Gln Leu His His Gln
            260                 265                 270

Met His Tyr Ser Gln Gln Ile Thr Val Ser Leu Ala Gln Gly Tyr Glu
        275                 280                 285

Gln Thr Ser Ser Ser Pro Lys Pro Arg Phe Lys Ser Tyr Ala Phe Thr
290                 295                 300

Gln Ala Ala Tyr Val Ala Thr Ser Asp Ser Thr Gln Ser Pro Tyr Pro
305                 310                 315                 320

Ser Gln His Leu Glu Ala Pro Arg Asp Lys Ser Leu Asp Ser Ser Leu
                325                 330                 335

Met Glu Thr Glu Val Asn Leu Asp Ser Tyr Gln Thr Ala Leu Glu Glu
            340                 345                 350

Val Leu Ser Trp Leu Leu Ser Ala Glu Asp Thr Leu Arg Ala Gln Gly
        355                 360                 365

Glu Ile Ser Asn Asp Val Glu Val Lys Glu Gln Phe His Ala His
370                 375                 380

Glu Gly Phe Met Met Asp Leu Thr Ser His Gln Gly Leu Val Gly Asn
385                 390                 395                 400

Val Leu Gln Leu Gly Ser Gln Leu Val Gly Lys Gly Lys Leu Ser Glu
                405                 410                 415

Asp Glu Glu Ala Glu Val Gln Glu Gln Met Asn Leu Leu Asn Ser Arg
            420                 425                 430

Trp Glu Cys Leu Arg Val Ala Ser Met Glu Lys Gln Ser Lys Leu His
        435                 440                 445

Lys Val Leu Met Asp Leu Gln Asn Gln Lys Leu Lys Glu Leu Asp Asp
450                 455                 460

Trp Leu Thr Lys Thr Glu Glu Arg Thr Lys Lys Met Glu Glu Glu Pro
```

```
                465                 470                 475                 480
            Phe Gly Pro Asp Leu Glu Asp Leu Lys Cys Gln Val Gln Gln His Lys
                            485                 490                 495

Val Leu Gln Glu Asp Leu Glu Gln Glu Gln Val Arg Val Asn Ser Leu
                            500                 505                 510

Thr His Met Val Val Val Asp Glu Ser Ser Gly Asp His Ala Thr
                            515                 520                 525

Ala Ala Leu Glu Glu Gln Leu Lys Val Leu Gly Asp Arg Trp Ala Asn
                    530                 535                 540

Ile Cys Arg Trp Thr Glu Asp Arg Trp Ile Val Leu Gln Asp Ile Leu
            545                 550                 555                 560

Leu Lys Trp Gln His Phe Thr Glu Glu Gln Cys Leu Phe Ser Thr Trp
                                565                 570                 575

Leu Ser Glu Lys Glu Asp Ala Met Lys Asn Ile Gln Thr Ser Gly Phe
                            580                 585                 590

Lys Asp Gln Asn Glu Met Met Ser Ser Leu His Lys Ile Ser Thr Leu
                        595                 600                 605

Lys Ile Asp Leu Glu Lys Lys Lys Pro Thr Met Glu Lys Leu Ser Ser
                    610                 615                 620

Leu Asn Gln Asp Leu Leu Ser Ala Leu Lys Asn Lys Ser Val Thr Gln
            625                 630                 635                 640

Lys Met Glu Ile Trp Met Glu Asn Phe Ala Gln Arg Trp Asp Asn Leu
                                645                 650                 655

Thr Gln Lys Leu Glu Lys Ser Ser Ala Gln Ile Ser Gln Ala Val Thr
                            660                 665                 670

Thr Thr Gln Pro Ser Leu Thr Gln Thr Thr Val Met Glu Thr Val Thr
                        675                 680                 685

Met Val Thr Thr Arg Glu Gln Ile Met Val Lys His Ala Gln Glu Glu
                    690                 695                 700

Leu Pro Pro Pro Pro Gln Lys Lys Arg Gln Ile Thr Val Asp Ala
            705                 710                 715                 720

Leu Glu Arg Leu Gln Glu Leu Gln Glu Ala Ala Asp Glu Leu Asp Leu
                                725                 730                 735

Lys Leu Arg Gln Ala Glu Val Ile Lys Gly Ser Trp Gln Pro Val Gly
                            740                 745                 750

Asp Leu Leu Ile Asp Ser Leu Gln Asp His Leu Glu Lys Val Lys Ala
                        755                 760                 765

Leu Arg Gly Glu Ile Ala Pro Leu Lys Glu Asn Val Asn Arg Val Asn
                    770                 775                 780

Asp Leu Ala His Gln Leu Thr Thr Leu Gly Ile Gln Leu Ser Pro Tyr
            785                 790                 795                 800

Asn Leu Ser Thr Leu Glu Asp Leu Asn Thr Arg Trp Arg Leu Leu Gln
                                805                 810                 815

Val Ala Val Glu Asp Arg Val Arg Gln Leu His Glu Ala His Arg Asp
                            820                 825                 830

Phe Gly Pro Ala Ser Gln His Phe Leu Ser Thr Ser Val Gln Gly Pro
                        835                 840                 845

Trp Glu Arg Ala Ile Ser Pro Asn Lys Val Pro Tyr Tyr Ile Asn His
                    850                 855                 860

Glu Thr Gln Thr Thr Cys Trp Asp His Pro Lys Met Thr Glu Leu Tyr
            865                 870                 875                 880

Gln Ser Leu Ala Asp Leu Asn Asn Val Arg Phe Ser Ala Tyr Arg Thr
                                885                 890                 895
```

-continued

```
Ala Met Lys Leu Arg Arg Leu Gln Lys Ala Leu Cys Leu Asp Leu Leu
            900                 905                 910

Ser Leu Ser Ala Ala Cys Asp Ala Leu Asp Gln His Asn Leu Lys Gln
            915                 920                 925

Asn Asp Gln Pro Met Asp Ile Leu Gln Ile Ile Asn Cys Leu Thr Thr
            930                 935                 940

Ile Tyr Asp Arg Leu Glu Gln Glu His Asn Asn Leu Val Asn Val Pro
945                 950                 955                 960

Leu Cys Val Asp Met Cys Leu Asn Trp Leu Leu Asn Val Tyr Asp Thr
                965                 970                 975

Gly Arg Thr Gly Arg Ile Arg Val Leu Ser Phe Lys Thr Gly Ile Ile
            980                 985                 990

Ser Leu Cys Lys Ala His Leu Glu Asp Lys Tyr Arg Tyr Leu Phe Lys
            995                 1000                1005

Gln Val Ala Ser Ser Thr Gly Phe Cys Asp Gln Arg Arg Leu Gly Leu
            1010                1015                1020

Leu Leu His Asp Ser Ile Gln Ile Pro Arg Gln Leu Gly Glu Val Ala
1025                1030                1035                1040

Ser Phe Gly Gly Ser Asn Ile Glu Pro Ser Val Arg Ser Cys Phe Gln
            1045                1050                1055

Phe Ala Asn Asn Lys Pro Glu Ile Glu Ala Ala Leu Phe Leu Asp Trp
            1060                1065                1070

Met Arg Leu Glu Pro Gln Ser Met Val Trp Leu Pro Val Leu His Arg
            1075                1080                1085

Val Ala Ala Glu Thr Ala Lys His Gln Ala Lys Cys Asn Ile Cys
            1090                1095                1100

Lys Glu Cys Pro Ile Ile Gly Phe Arg Tyr Arg Ser Leu Lys His Phe
1105                1110                1115                1120

Asn Tyr Asp Ile Cys Gln Ser Cys Phe Phe Ser Gly Arg Val Ala Lys
            1125                1130                1135

Gly His Lys Met His Tyr Pro Met Val Glu Tyr Cys Thr Pro Thr Thr
            1140                1145                1150

Ser Gly Glu Asp Val Arg Asp Phe Ala Lys Val Leu Lys Asn Lys Phe
            1155                1160                1165

Arg Thr Lys Arg Tyr Phe Ala Lys His Pro Arg Met Gly Tyr Leu Pro
            1170                1175                1180

Val Gln Thr Val Leu Glu Gly Asp Asn Met Glu Thr Pro Val Thr Leu
1185                1190                1195                1200

Ile Asn Phe Trp Pro Val Asp Ser Ala Pro Ala Ser Ser Pro Gln Leu
            1205                1210                1215

Ser His Asp Asp Thr His Ser Arg Ile Glu His Tyr Ala Ser Arg Leu
            1220                1225                1230

Ala Glu Met Glu Asn Ser Asn Gly Ser Tyr Leu Asn Asp Ser Ile Ser
            1235                1240                1245

Pro Asn Glu Ser Ile Asp Asp Glu His Leu Leu Ile Gln His Tyr Cys
            1250                1255                1260

Gln Ser Leu Asn Gln Asp Ser Pro Leu Ser Gln Pro Arg Ser Pro Ala
1265                1270                1275                1280

Gln Ile Leu Ile Ser Leu Glu Ser Glu Glu Arg Gly Glu Leu Glu Arg
            1285                1290                1295

Ile Leu Ala Asp Leu Glu Glu Glu Asn Arg Asn Leu Gln Ala Glu Tyr
            1300                1305                1310
```

```
Asp Arg Leu Lys Gln Gln His Glu His Lys Gly Leu Ser Pro Leu Pro
    1315                1320                1325

Ser Pro Pro Glu Met Met Pro Thr Ser Pro Gln Ser Pro Arg Asp Ala
    1330                1335                1340

Glu Leu Ile Ala Glu Ala Lys Leu Leu Arg Gln His Lys Gly Arg Leu
1345                1350                1355                1360

Glu Ala Arg Met Gln Ile Leu Glu Asp His Asn Lys Gln Leu Glu Ser
            1365                1370                1375

Gln Leu His Arg Leu Arg Gln Leu Leu Glu Gln Pro Gln Ala Glu Ala
        1380                1385                1390

Lys Val Asn Gly Thr Thr Val Ser Ser Pro Ser Thr Ser Leu Gln Arg
    1395                1400                1405

Ser Asp Ser Ser Gln Pro Met Leu Leu Arg Val Val Gly Ser Gln Thr
    1410                1415                1420

Ser Glu Ser Met Gly Glu Glu Asp Leu Leu Ser Pro Pro Gln Asp Thr
1425                1430                1435                1440

Ser Thr Gly Leu Glu Glu Val Met Glu Gln Leu Asn Asn Ser Phe Pro
            1445                1450                1455

Ser Ser Arg Gly Arg Asn Ala Pro Gly Lys Pro Met Arg Glu Asp Thr
        1460                1465                1470

Met
```

<210> SEQ ID NO 5
<211> LENGTH: 4428
<212> TYPE: DNA
<213> ORGANISM: Artificial Sequence
<220> FEATURE:
<223> OTHER INFORMATION: murine MD4 (cDNA)

<400> SEQUENCE: 5

```
atgctgtggt gggaggaagt ggaggactgc tacgagagag aggacgtgca gaagaaaacc      60
ttcaccaagt ggatcaacgc ccagttcagc aagttcggca gcagcacat cgacaacctg     120 ttcagcgacc tgcaggacgg caagagactg ctggatctgc tggagggact gaccggccag     180
aagctgccca ggagaagggg cagcaccaga gtgcacgccc tgaacaacgt gaacaaggcc     240
ctgagagtgc tgcagaagaa caacgtggac ctggtgaata tcggcagcac cgacatcgtg     300
gacggcaacc acaagctgac cctgggcctg atctggaaca tcatcctgca ctggcaggtg     360
aagaacgtga tgaaaaccat catggccggc ctgcagcaga ccaacagcga agatcctg      420 ctgagctggg tgaggcagag caccagaaac taccccagg tgaacgtgat caacttcacc     480
agcagctgga gcgacggcct ggccctgaac gccctgatcc acagccacag acccgacctg     540
ttcgactgga cagcgtggt gtcccagcac agcgccaccc agagactgga gcacgccttc     600
aacatcgcca gtgccagct gggcatcgag aagctgctgg accccgagga cgtggccacc     660
acctaccccg acaagaaaag catcctcatg tatatcacct ctctgtttca ggtgctgccc     720
cagcaggtgt ccatcgaggc catccaggaa gtggaaatgc tgccccggac cagcagcaaa     780
gtgacccggg aggagcactt ccagctgcac caccagatgc actatagcca gcagatcacc     840
gtgtccctgg cccagggcta cgagcagacc agcagctccc ccaagcccag attcaagagc     900
tacgccttca cccaggccgc ctacgtggcc acaagcgata gcacccagag ccctacccc     960 agccagcacc tggaggcccc tagagacaag agcctggaca gcagcctgat ggagacagaa    1020
gtgaacctgg acagctacca gaccgccctg gaggaagtgt gtcttggct gctgtccgcc    1080 gaggacaccc tgagagccca gggcgagatc agcaacgacg tggaagaagt gaaggagcag    1140
```

```
ttccacgccc acgagggctt catgatggac ctgacctccc atcagggcct ggtgggcaac    1200
gtgctgcagc tgggcagcca gctcgtggga aagggcaagc tgagcgagga cgaggaggcc    1260
gaagtgcagg aacagatgaa cctgctgaac agcagatggg agtgcctgag agtggccagc    1320
atggagaagc agagcaagct gcacaaagtg ctgatggatc tgcagaacca gaagctgaag    1380
gaactggacg actggctgac caagaccgag gagcggacca agaagatgga ggaggagccc    1440
ttcggccccg acctggagga cctgaagtgc caggtgcagc agcataaggt cctgcaggag    1500
gacctggaac aggagcaggt gcgcgtgaac agcctgaccc acatggtggt cgtggtggac    1560
gagagcagcg gcgaccacgc cacagccgcc ctggaagagc agctgaaagt gctgggcgac    1620
agatgggcca atatctgccg gtggaccgag gatagatgga tcgtgctgca ggacatcctg    1680
ctgaagtggc agcacttcac cgaggagcag tgcctgttta gcacctggct gagcgagaaa    1740
gaggacgcca tgaagaacat ccagaccagc ggcttcaagg accagaacga gatgatgagc    1800
agcctgcaca agatcagcac cctgaagatc gacctggaga agaaaaagcc cacaatggag    1860
aagctgtcca gcctgaacca ggacctgctg agcgccctga gaacaagag cgtgacccag    1920 aaaatggaga tctggatgga gaatttcgca cagaggtggg acaacctgac ccagaagctg    1980
gagaagagca gcgcccagat cagccaggcc gtgaccacca cccagcccag cctgacacag    2040
accaccgtga tggagaccgt gaccatggtg accacccggg agcagatcat ggtgaagcac    2100
gcccaggagg agctgcccc tccccccct cagaagaagc ggcagatcac agtggatgcc    2160
ctggagagac tgcaggagct gcaggaagcc gccgacgagc tggatctgaa gctgagacag    2220
gccgaagtga tcaagggcag ctggcagcct gtgggcgatc tgctgatcga cagcctgcag    2280
gaccacctgg agaaagtgaa ggccctgcgg ggcgagatcg cccccctgaa ggagaacgtg    2340
aaccgcgtga acgacctggc ccatcagctg accacctgg gcattcagct gagcccctac    2400
aacctgagca ccctggagga tctgaacacc cggtggagac tgctgcaggt ggccgtggag    2460
gatagagtga ggcagctgca cgaggcccac agagacttcg ccctgcctc ccagcacttc    2520 ctgagcacca cgtgcaggg cccctgggag agagccatca gccccaacaa agtgccctac    2580
tacatcaacc acgagaccca gaccacctgc tgggaccacc ctaagatgac cgagctgtac    2640
cagagcctgg ccgacctgaa caatgtgcgg ttcagcgcct acagaaccgc catgaagctg    2700
cggagactgc agaaggccct gtgcctggac ctgctgtccc tgagcgccgc ctgcgacgcc    2760
ctggaccagc acaacctgaa gcagaacgac cagcccatgg atatcctgca gatcatcaac    2820
tgcctgacca ccatctacga tcggctggag caggagcaca acaacctggt gaacgtgccc    2880
ctgtgcgtgg acatgtgcct gaattggctg ctgaacgtgt acgacaccgg caggaccggc    2940
agaatcagag tgctgtcctt caagaccggc atcatcagcc tgtgcaaggc ccacctggag    3000
gataagtacc gctacctgtt caagcaggtg gccagcagca ccggcttctg cgatcagagg    3060
agactgggcc tgctgctgca cgatagcatc cagatcccta ggcagctggg cgaggtggcc    3120
agcttcggcg gcagcaacat cgagcccagc gtgcggagct gcttccagtt cgccaacaac    3180
aagcccgaga tcgaggccgc cctgttcctg gactggatgc ggctggaacc ccagagcatg    3240
gtctggctgc ccgtgctgca cagagtggct gccgccgaga ccgccaagca ccaggccaag    3300
tgcaacatct gcaaagagtg ccccatcatc ggcttccggg tacagaagcct gaagcacttc    3360 aactacgaca tctgccagag ctgcttttc agcggcagag tggccaaggg ccacaagatg    3420
cactacccca tggtggagta ctgcaccccc accacctccg gcgaggacgt gcgggacttc    3480
```

```
gccaaggtgc tgaagaacaa gttccggacc aagcggtact ttgccaagca ccccggatg      3540 ggctacctgc ccgtgcagac cgtgctggaa ggcgacaaca tggaaacccc cgtgaccctg      3600
atcaacttct ggcccgtgga cagcgcccct gccagcagcc cccagctgtc ccacgacgac      3660
acccacagcc ggatcgagca ctacgccagc cggctcgccg agatggaaaa cagcaacggc      3720
agctacctga acgacagcat cagccccaac gagagcatcg acgacgagca cctgctgatc      3780
cagcactact gtcagagcct gaaccaggac agcccctga gccagcccag aagccctgcc       3840
cagatcctga tcagcctgga aagcgaggaa cggggcgagc tggaacggat cctggccgac      3900
ctggaagagg aaaaccggaa cctgcaggcc gagtacgacc ggctgaagca gcagcacgag      3960
cacaagggcc tgagccccct gcccagcccc cctgagatga tgcccacctc cccccagagc      4020
cccagggacg ccgagctgat cgccgaggcc aagctgctgc ggcagcacaa ggggcggctg      4080
gaagcccgga tgcagatcct ggaagatcac aacaagcagc tggaaagcca gctgcaccgg      4140
ctgagacagc tgctggaaca gccccaggcc gaagccaagg tgaacggcac caccgtgagc      4200
agccccagca ccagcctgca gcggagcgac agctctcagc caatgctcct gcgggtggtg      4260
ggctctcaga ccagcgagag catgggcgaa gaggacctgc tgtccccacc tcaagacacc      4320
agcaccggcc tggaagaagt gatggaacag ctgaacaaca gcttccccag cagccggggc      4380
agaaacgccc ccggcaagcc catgcgggag gacaccatgt gatgatga                   4428
```

<210> SEQ ID NO 6
<211> LENGTH: 5466
<212> TYPE: DNA
<213> ORGANISM: Artificial Sequence
<220> FEATURE:
<223> OTHER INFORMATION: AAV ITR mMD4

<400> SEQUENCE: 6

```
gcgcgctcgc tcgctcactg aggccgcccg ggcaaagccc gggcgtcggg cgacctttgg       60
tcgcccggcc tcagtgagcg agcgagcgcg cagagagga gtggccaact ccatcactag       120
gggttccttg tagttaatga ttaacccgcc atgctactta tctacgtagc catgctctag      180
acatggctcg acagatcgag ctccaccgcg gtggcggccg tccgccctcg caccatcct       240 cacgacaccc aaatatggcg acgggtgagg aatggtgggg agttattttt agagcggtga      300
ggaaggtggg caggcagcag gtgttggcgc tctaaaaata actcccggga gttattttta      360
gagcggagga atggtggaca cccaaatatg gcgacggttc ctcacccgtc gccatatttg      420
ggtgtccgcc ctcggccggg gccgcattcc tggggccgg gcggtgctcc cgcccgcctc       480
gataaaaggc tccggggccg gcggcggccc acgagctacc cggaggagcg ggaggcgcca      540
agctctagaa ctagtggatc ccccgggctg caggaattcg ccaccatgct gtggtgggag      600
gaagtggagg actgctacga gagagaggac gtgcagaaga aaaccttcac caagtggatc      660
aacgcccagt tcagcaagtt cggcaagcag cacatcgaca acctgttcag cgacctgcag      720
gacggcaaga gactgctgga tctgctggag ggactgaccg ccagaagct gcccaaggag       780 aagggcagca ccagagtgca cgccctgaac aacgtgaaca aggccctgag agtgctgcag      840
aagaacaacg tggacctggt gaatatcggc agcaccgaca tcgtggacgg caaccacaag      900 ctgacctgg gcctgatctg aacatcatc ctgcactggc aggtgaagaa cgtgatgaaa        960
accatcatgg ccggcctgca gcagaccaac agcgagaaga tcctgctgag ctgggtgagg      1020
cagagcacca gaaactaccc ccaggtgaac gtgatcaact tcaccagcag ctggagcgac      1080
ggcctggccc tgaacgcccct gatccacagc cacagacccg acctgttcga ctggaacagc      1140
```

-continued

```
gtggtgtccc agcacagcgc cacccagaga ctggagcacg ccttcaacat cgccaagtgc    1200
cagctgggca tcgagaagct gctggacccc gaggacgtgg ccaccaccta ccccgacaag    1260
aaaagcatcc tcatgtatat cacctctctg tttcaggtgc tgccccagca ggtgtccatc    1320
gaggccatcc aggaagtgga aatgctgccc cggaccagca gcaaagtgac ccgggaggag    1380
cacttccagc tgcaccacca gatgcactat agccagcaga tcaccgtgtc cctggcccag    1440
ggctacgagc agaccagcag ctcccccaag cccagattca agagctacgc cttcacccag    1500
gccgcctacg tggccacaag cgatagcacc cagagcccct accccagcca gcacctggag    1560
gcccctagag acaagagcct ggacagcagc ctgatggaga cagaagtgaa cctggacagc    1620
taccagaccg ccctggagga agtgctgtct tggctgctgt ccgccgagga cccctgaga     1680 gcccagggcg agatcagcaa cgacgtggaa gaagtgaagg agcagttcca cgcccacgag    1740
ggcttcatga tggacctgac ctcccatcag ggcctggtgg gcaacgtgct gcagctgggc    1800
agccagctcg tgggaaaggg caagctgagc gaggacgagg aggccgaagt gcaggaacag    1860
atgaacctgc tgaacagcag atgggagtgc ctgagagtgg ccagcatgga gaagcagagc    1920
aagctgcaca agtgctgat ggatctgcag aaccagaagc tgaaggaact ggacgactgg    1980
ctgaccaaga ccgaggagcg gaccaagaag atggaggagg agcccttcgg ccccgacctg    2040
gaggacctga agtgccaggt gcagcagcat aaggtcctgc aggaggacct ggaacaggag    2100
caggtgcgcg tgaacagcct gacccacatg gtggtcgtgg tggacgagag cagcggcgac    2160
cacgccacag ccgccctgga agagcagctg aaagtgctgg gcgacagatg ggccaatatc    2220
tgccggtgga ccgaggatag atggatcgtg ctgcaggaca tcctgctgaa gtggcagcac    2280
ttcaccgagg agcagtgcct gtttagcacc tggctgagcg agaaagagga cgccatgaag    2340
aacatccaga ccagcggctt caaggaccag aacgagatga tgagcagcct gcacaagatc    2400
agcaccctga agatcgacct ggagaagaaa aagcccacaa tggagaagct gtccagcctg    2460
aaccaggacc tgctgagcgc cctgaagaac aagagcgtga cccagaaaat ggagatctgg    2520
atggagaatt tcgcacagag gtgggacaac ctgacccaga agctggagaa gagcagcgcc    2580
cagatcagcc aggccgtgac caccacccag cccagcctga cacagaccac cgtgatggag    2640
accgtgacca tggtgaccac ccgggagcag atcatggtga agcacgccca ggaggagctg    2700
cccccctccc ccctcagaa gaagcggcag atcacagtgg atgccctgga gagactgcag    2760
gagctgcagg aagccgccga cgagctggat ctgaagctga cagggccga agtgatcaag    2820 ggcagctggc agcctgtggg cgatctgctg atcgacagcc tgcaggacca cctggagaaa    2880
gtgaaggccc tgcggggcga gatcgccccc ctgaaggaga acgtgaaccg cgtgaacgac    2940
ctggcccatc agctgaccac cctgggcatt cagctgagcc cctacaacct gagcaccctg    3000
gaggatctga caccccggtg gagactgctg caggtggccg tggaggatag agtgaggcag    3060
ctgcacgagg cccacagaga cttcggccct gcctcccagc acttcctgag caccagcgtg    3120
cagggcccct gggagagagc catcagcccc aacaaagtgc cctactacat caaccacgag    3180
acccagacca cctgctggga ccaccctaag atgaccgagc tgtaccagag cctggccgac    3240
ctgaacaatg tgcggttcag cgcctacaga accgccatga gctgcgagag actgcagaag    3300
gccctgtgcc tggacctgct gtccctgagc gccgcctgcg acgccctgga ccagcacaac    3360
ctgaagcaga acgaccagcc catggatatc ctgcagatca tcaactgcct gaccaccatc    3420
tacgatcggc tggagcagga gcacaacaac ctggtgaacg tgcccctgtg cgtggacatg    3480
```

```
tgcctgaatt ggctgctgaa cgtgtacgac accggcagga ccggcagaat cagagtgctg      3540
tccttcaaga ccggcatcat cagcctgtgc aaggcccacc tggaggataa gtaccgctac      3600
ctgttcaagc aggtggccag cagcaccggc ttctgcgatc agaggagact gggcctgctg      3660
ctgcacgata gcatccagat ccctaggcag ctgggcgagg tggccagctt cggcggcagc      3720
aacatcgagc ccagcgtgcg gagctgcttc cagttcgcca caacaagcc cgagatcgag       3780 gccgccctgt tcctggactg gatgcggctg gaacccaga gcatggtctg gctgcccgtg       3840
ctgcacagag tggctgccgc cgagaccgcc aagcaccagg ccaagtgcaa catctgcaaa     3900
gagtgcccca tcatcggctt ccggtacaga agcctgaagc acttcaacta cgacatctgc     3960
cagagctgct ttttcagcgg cagagtggcc aagggccaca agatgcacta ccccatggtg     4020
gagtactgca cccccaccac ctccggcgag gacgtgcggg acttcgccaa ggtgctgaag     4080
aacaagttcc ggaccaagcg gtactttgcc aagcaccccc ggatgggcta cctgcccgtg     4140
cagaccgtgc tggaaggcga caacatgaa accccgtga ccctgatcaa cttctggccc       4200
gtggacagcg cccctgccag cagcccccag ctgtcccacg acgacaccca cagccggatc     4260
gagcactacg ccagccggct cgccgagatg gaaaacagca acggcagcta cctgaacgac    4320
agcatcagcc caacgagag catcgacgac gagcacctgc tgatccagca ctactgtcag     4380
agcctgaacc aggacagccc cctgagccag cccagaagcc ctgcccagat cctgatcagc    4440
ctggaaagcg aggaacgggg cgagctgaa cggatcctgg ccgacctgga agaggaaaac    4500
cggaacctgc aggccgagta cgaccggctg aagcagcagc acgagcacaa gggcctgagc    4560
cccctgccca gccccctga tgatgatgcc acctccccc agagcccag ggacgccgag       4620 ctgatcgccg aggccaagct gctgcggcag cacaagggc ggctggaagc ccggatgcag     4680
atcctggaag atcacaacaa gcagctgaa agccagctgc accggctgag acagctgctg    4740
gaacagcccc aggccgaagc caaggtgaac ggcaccaccg tgagcagccc cagcaccagc   4800
ctgcagcgga gcgacagctc tcagccaatg ctcctgcggg tggtgggctc tcagaccagc    4860
gagagcatgg gcgaagagga cctgctgtcc ccacctcaag acaccagcac cggcctggaa   4920
gaagtgatgg aacagctgaa caacagcttc cccagcagcc ggggcagaaa cgcccccggc     4980
aagcccatgc gggaggacac catgtgatga tgagcggccg cttcccttta gtgagggtta      5040
atgcttcgag cagacatgat aagatacatt gatgagtttg gacaaaccac aactagaatg     5100
cagtgaaaaa aatgctttat ttgtgaaatt tgtgatgcta ttgctttatt tgtaaccatt      5160
ataagctgca ataaacaagt taacaacaac aattgcattc attttatgtt tcaggttcag     5220
ggggagatgt gggaggtttt ttaaagcaag taaaacctct acaaatgtgg taaaatccga    5280
taaggactag agcatggcta cgtagataag tagcatggcg ggttaatcat taactacaag    5340
gaacccctag tgatggagtt ggccactccc tctctgcgcg ctcgctcgct cactgaggcc    5400
gggcgaccaa aggtcgcccg acgcccgggc tttgcccggg cggcctcagt gagcgagcga    5460
gcgcgc                                                               5466
```

<210> SEQ ID NO 7
<211> LENGTH: 1393
<212> TYPE: PRT
<213> ORGANISM: Artificial Sequence
<220> FEATURE:
<223> OTHER INFORMATION: canine MD3 (PRT)

<400> SEQUENCE: 7

Met Leu Trp Trp Glu Glu Val Glu Asp Cys Tyr Glu Arg Glu Asp Val

```
1               5                   10                  15
Gln Lys Lys Thr Phe Thr Lys Trp Ile Asn Ala Gln Phe Ser Lys Phe
                 20                  25                  30

Gly Lys Gln His Ile Glu Asn Leu Phe Ser Asp Leu Gln Asp Gly Arg
                 35                  40                  45

Arg Leu Leu Asp Leu Leu Glu Gly Leu Thr Gly Gln Lys Leu Pro Lys
 50                  55                  60

Glu Lys Gly Ser Thr Arg Val His Ala Leu Asn Asn Val Asn Lys Ala
 65                  70                  75                  80

Leu Arg Val Leu Gln Lys Asn Asn Val Asp Leu Val Asp Ile Gly Ser
                 85                  90                  95

Thr Asp Ile Val Asp Gly Asn His Lys Leu Thr Leu Gly Leu Ile Trp
                100                 105                 110

Asn Ile Ile Leu His Trp Gln Val Lys Asn Val Met Lys Asn Ile Met
                115                 120                 125

Ala Gly Leu Gln Gln Thr Asn Ser Glu Lys Ile Leu Leu Ser Trp Val
                130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
                180                 185                 190

Thr Gln Arg Leu Glu His Ala Phe Asn Ile Ala Lys Tyr Gln Leu Gly
                195                 200                 205

Ile Glu Lys Leu Leu Asp Pro Glu Asp Val Ala Thr Thr Tyr Pro Asp
210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Ser Lys Val Thr Arg Glu Glu His Phe Gln Leu His His Gln Met
                260                 265                 270

His Tyr Ser Gln Gln Ile Thr Val Ser Leu Ala Gln Gly Tyr Glu Arg
                275                 280                 285

Ala Pro Ser Ser Pro Lys Pro Arg Phe Lys Ser Tyr Ala Tyr Thr Gln
290                 295                 300

Ala Ala Tyr Val Thr Thr Ser Asp Pro Thr Arg Ser Pro Leu Pro Ser
305                 310                 315                 320

Gln His Leu Glu Thr Pro Glu Asp Lys Ser Phe Gly Arg Ser Leu Thr
                325                 330                 335

Glu Thr Glu Ala Asn Leu Asp Ser Tyr Gln Thr Ala Leu Glu Glu Val
                340                 345                 350

Leu Ser Trp Leu Leu Ser Ala Glu Asp Ala Leu Gln Ala Gln Gly Glu
                355                 360                 365

Ile Ser Asn Asp Val Glu Val Lys Glu Gln Phe His Thr His Glu
                370                 375                 380

Gly Tyr Met Met Asp Leu Thr Ser His Gln Gly Arg Val Gly Asn Val
385                 390                 395                 400

Leu Gln Leu Gly Ser Gln Leu Ile Gly Thr Gly Lys Leu Ser Glu Asp
                405                 410                 415

Glu Glu Thr Glu Val Gln Glu Gln Met Asn Leu Leu Asn Ser Arg Trp
                420                 425                 430
```

```
Glu Cys Leu Arg Val Ala Ser Met Glu Lys Gln Ser Asn Leu His Lys
            435                 440                 445
Val Leu Met Asp Leu Gln Asn Gln Gln Leu Lys Glu Leu Asn Asp Trp
450                 455                 460
Leu Thr Lys Thr Glu Glu Arg Thr Arg Lys Met Glu Lys Glu Pro Leu
465                 470                 475                 480
Gly Pro Asp Ile Glu Asp Leu Lys Arg Gln Val Gln Gln His Lys Val
                485                 490                 495
Leu Gln Glu Asp Leu Glu Gln Glu Gln Val Arg Val Asn Ser Leu Thr
                500                 505                 510
His Met Val Val Val Asp Glu Ser Ser Gly Asp His Ala Thr Ala
            515                 520                 525
Ala Leu Glu Glu Gln Leu Lys Val Leu Gly Gly Arg Trp Ala Asn Ile
530                 535                 540
Cys Arg Trp Thr Glu Asp Arg Trp Val Leu Leu Gln Asp Ile Leu Leu
545                 550                 555                 560
Lys Trp Gln Arg Phe Thr Glu Glu Gln Cys Leu Phe Ser Ala Trp Leu
                565                 570                 575
Ser Glu Lys Glu Asp Ala Val Asn Lys Ile His Thr Thr Gly Phe Lys
            580                 585                 590
Asp Gln Ser Glu Val Leu Ser Asn Leu Gln Lys Leu Ala Val Leu Lys
            595                 600                 605
Thr Asp Leu Glu Lys Lys Lys Gln Thr Met Asp Lys Leu Cys Ser Leu
610                 615                 620
Asn Gln Asp Leu Leu Ser Ala Leu Lys Asn Thr Val Val Ala His Lys
625                 630                 635                 640
Met Glu Ala Trp Leu Asp Asn Ser Ala Gln Arg Trp Asp Asn Leu Val
                645                 650                 655
Gln Lys Leu Glu Lys Ser Ser Ala Gln Ile Ser Gln Ala Val Thr Thr
            660                 665                 670
Thr Gln Pro Ser Leu Thr Gln Thr Thr Val Met Glu Thr Val Thr Met
            675                 680                 685
Val Thr Thr Arg Glu His Ile Leu Val Lys His Ala Gln Glu Glu Leu
690                 695                 700
Pro Pro Pro Pro Gln Lys Lys Arg Gln Ile Ile Val Asp Ala Leu
705                 710                 715                 720
Glu Arg Leu Gln Glu Leu Gln Glu Ala Thr Asp Glu Leu Asp Leu Lys
                725                 730                 735
Leu Arg Gln Ala Glu Val Ile Lys Gly Ser Trp Gln Pro Val Gly Asp
                740                 745                 750
Leu Leu Ile Asp Ser Leu Gln Asp His Leu Glu Lys Val Lys Ala Leu
                755                 760                 765
Arg Gly Glu Thr Thr Pro Leu Lys Glu Asn Val Ser Tyr Val Asn Asp
770                 775                 780
Leu Ala Arg Gln Leu Thr Thr Leu Gly Ile Gln Leu Ser Pro Tyr Asn
785                 790                 795                 800
Leu Asn Thr Leu Glu Asp Leu Asn Thr Arg Trp Lys Leu Leu Gln Val
                805                 810                 815
Ala Ile Glu Asp Arg Ile Arg Gln Leu His Glu Ala His Arg Asp Phe
                820                 825                 830
Gly Pro Ala Ser Gln His Phe Leu Ser Thr Ser Val Gln Gly Pro Trp
                835                 840                 845
```

```
Glu Arg Ala Ile Ser Pro Asn Lys Val Pro Tyr Tyr Ile Asn His Glu
850                 855                 860
Thr Gln Thr Thr Cys Trp Asp His Pro Lys Met Thr Glu Leu Tyr Gln
865                 870                 875                 880
Ser Leu Ala Asp Leu Asn Asn Val Arg Phe Ser Ala Tyr Arg Thr Ala
                885                 890                 895
Met Lys Leu Arg Arg Leu Gln Lys Ala Leu Cys Leu Asp Leu Leu Ser
                900                 905                 910
Leu Ser Ala Ala Cys Asp Ala Leu Asp Gln His Asn Leu Lys Gln Asn
                915                 920                 925
Asp Gln Pro Met Asp Ile Leu Gln Val Ile Asn Cys Leu Thr Thr Ile
930                 935                 940
Tyr Asp Arg Leu Glu Gln Glu His Asn Asn Leu Val Asn Val Pro Leu
945                 950                 955                 960
Cys Val Asp Met Cys Leu Asn Trp Leu Leu Asn Val Tyr Asp Thr Gly
                965                 970                 975
Arg Thr Gly Arg Ile Arg Val Leu Ser Phe Lys Thr Gly Ile Ile Ser
                980                 985                 990
Leu Cys Lys Ala His Leu Glu Asp Lys Tyr Arg Tyr Leu Phe Lys Gln
                995                 1000                1005
Val Ala Ser Ser Thr Gly Phe Cys Asp Gln Arg Arg Leu Gly Leu Leu
1010                1015                1020
Leu His Asp Ser Ile Gln Ile Pro Arg Gln Leu Gly Glu Val Ala Ser
1025                1030                1035                1040
Phe Gly Gly Ser Asn Ile Glu Pro Ser Val Arg Ser Cys Phe Gln Phe
                1045                1050                1055
Ala Asn Asn Lys Pro Glu Ile Glu Ala Ala Leu Phe Leu Asp Trp Met
                1060                1065                1070
Arg Leu Glu Pro Gln Ser Met Val Trp Leu Pro Val Leu His Arg Val
                1075                1080                1085
Ala Ala Ala Glu Thr Ala Lys His Gln Ala Lys Cys Asn Ile Cys Lys
                1090                1095                1100
Glu Cys Pro Ile Ile Gly Phe Arg Tyr Arg Ser Leu Lys His Phe Asn
1105                1110                1115                1120
Tyr Asp Ile Cys Gln Ser Cys Phe Phe Ser Gly Arg Val Ala Lys Gly
                1125                1130                1135
His Lys Met His Tyr Pro Met Val Glu Tyr Cys Thr Pro Thr Thr Ser
                1140                1145                1150
Gly Glu Asp Val Arg Asp Phe Ala Lys Val Leu Lys Asn Lys Phe Arg
                1155                1160                1165
Thr Lys Arg Tyr Phe Ala Lys His Pro Arg Met Gly Tyr Leu Pro Val
                1170                1175                1180
Gln Thr Val Leu Glu Gly Asp Asn Met Glu Thr Pro Val Thr Leu Ile
1185                1190                1195                1200
Asn Phe Trp Pro Val Asp Ser Ala Pro Ala Ser Ser Pro Gln Leu Ser
                1205                1210                1215
His Asp Asp Thr His Ser Arg Ile Glu His Tyr Ala Ser Arg Leu Ala
                1220                1225                1230
Glu Met Glu Asn Ser Asn Gly Ser Tyr Leu Asn Asp Ser Ile Ser Pro
                1235                1240                1245
Asn Glu Ser Ile Asp Asp Glu His Leu Leu Ile Gln His Tyr Cys Gln
                1250                1255                1260
Ser Leu Asn Gln Asp Ser Pro Leu Ser Gln Pro Arg Ser Pro Ala Gln
```

Ile Leu Ile Ser Leu Glu Ser Glu Arg Gly Glu Leu Arg Ile
                1285                1290                1295

Leu Ala Asp Leu Glu Glu Glu Asn Arg Asn Leu Gln Ala Glu Tyr Asp
            1300                1305                1310

Arg Leu Lys Gln Gln His Glu His Lys Gly Leu Ser Pro Leu Pro Ser
        1315                1320                1325

Pro Pro Glu Met Met Pro Thr Ser Pro Gln Ser Pro Arg Asp Ala Glu
    1330                1335                1340

Leu Ile Ala Glu Ala Lys Leu Leu Arg Gln His Lys Gly Arg Leu Glu
1345                1350                1355                1360

Ala Arg Met Gln Ile Leu Glu Asp His Asn Lys Gln Leu Glu Ser Gln
            1365                1370                1375

Leu His Arg Leu Arg Gln Leu Leu Glu Gln Pro Gln Ala Glu Asp Thr
        1380                1385                1390

Met

<210> SEQ ID NO 8
<211> LENGTH: 4188
<212> TYPE: DNA
<213> ORGANISM: Artificial Sequence
<220> FEATURE:
<223> OTHER INFORMATION: canine MD3 (cDNA)

<400> SEQUENCE: 8

```
atgctgtggt gggaggaagt ggaggactgc tacgagagag aggacgtgca gaagaaaacc      60
ttcaccaagt ggatcaacgc ccagttcagc aagttcggca gcagcacat cgagaacctg     120
ttcagcgatc tgcaggatgg caggagactg ctggatctgc tggagggact gaccggccag     180
aagctgccca ggagaagggg cagcaccaga gtgcacgccc tgaacaacgt gaacaaggcc     240
ctgagagtgc tgcagaagaa caacgtggac ctggtggata tcggcagcac cgacatcgtg     300
gacggcaacc acaagctgac cctgggcctg atctggaaca tcatcctgca ctggcaggtg     360
aagaacgtga tgaagaacat catggccggc ctgcagcaga ccaacagcga aagatcctg     420
ctgagctggg tgaggcagag caccagaaac tacccccagg tgaacgtgat caacttcacc     480
acctcctgga gcgacggcct ggccctgaac gccctgatcc acagccacag acccgacctg     540
ttcgactgga cagcgtggt gtgtcagcag agcgccaccc agagactgga gcacgccttc     600
aacatcgcca gtaccagct gggcatcgag aagctgctgg accccgagga cgtggccacc     660
acctacccccg acaagaaaag catcctgatg tatattacca gcctgttcca ggtgctgccc     720
cagcaggtgt ccatcgaggc catccaggaa gtggaaatgc tgcccaggcc agcaaagtg     780
accagggagg agcacttcca gctgcaccac cagatgcact atagccagca gatcaccgtg     840
tccctggccc agggctatga gagagcccct agcagcccca gccccggtt caagagctac     900
gcctacaccc aggccgccta cgtgaccacc tccgacccca ccagaagccc cctgcccagc     960
cagcacctgg agaccctga ggataagagc ttcggcagaa gcctgaccga gaccgaggcc    1020
aacctggata ctaccagac cgccctggag gaagtgctgt cttggctgct gtccgccgag    1080
gacgccctgc aggcccaggg cgagatcagc aacgacgtgg aagaagtgaa ggagcagttc    1140
cacacccacg agggctacat gatggacctg accagccacc agggcagagt gggcaacgtg    1200
ctgcagctgg cagccagct gatcggcacc ggcaagctga cgaggacga ggagaccgaa    1260
gtgcaggaac agatgaacct gctgaacagc agatgggagt gcctgagagt ggccagcatg    1320
```

```
gagaagcaga gcaacctgca caaagtgctg atggatctgc agaaccagca gctgaaggag    1380
ctgaacgact ggctgaccaa gacagaggag cggacccgga agatggagaa ggagcccctg    1440
ggccctgaca tcgaggacct gaagaggcag gtgcagcagc ataaggtcct gcaggaggat    1500
ctggagcagg agcaggtgcg cgtgaacagc ctgacccaca tggtggtcgt ggtggacgag    1560
agcagcggcg accacgccac agccgccctg aagagcagc tgaaagtgct gggcggcaga    1620
tgggccaata tctgccggtg gaccgaggac agatgggtgc tgctgcagga catcctgctg    1680
aagtggcaga gattcaccga ggagcagtgc ctgtttagcg cctggctgag cgagaaggag    1740
gacgccgtga acaagatcca caccaccggc ttcaaggacc agagcgaagt gctgtccaac    1800
ctgcagaagc tggccgtgct gaaaaccgac ctggagaaga aaaagcagac catggacaag    1860
ctgtgcagcc tgaaccagga cctgctgagc gccctgaaga caccgtggt ggcccacaag    1920 atggaggcct ggctggataa tagcgctcag agatgggata tctggtgca gaaactggag    1980 aagagcagcg cccagatcag ccaggccgtg accaccaccc agcccagcct gacacagacc    2040
accgtgatgg agaccgtgac catggtgacc accaggagc acatcctggt gaagcacgcc    2100
caggaggagc tgcccccctcc cccccctcag aagaagcggc agatcatcgt ggatgccctg    2160
gagagactgc aggagctgca ggaagccacc gacgagctgg acctgaagct gagacaggcc    2220
gaagtgatca gggcagctg gcagcctgtg ggcgatctgc tgatcgacag cctgcaggac    2280
cacctggaga aagtgaaggc cctgcgggc gagaccaccc ccctgaagga gaacgtgtcc    2340
tacgtgaacg acctggccag acagctgacc accctgggca ttcagctgag ccccctacaac    2400 ctgaacaccc tggaggatct gaacacccgg tggaaactgc tgcaggtggc cattgaggac    2460
cggatcaggc agctgcacga ggcccacaga gacttcggcc ctgcttctca gcatttcctg    2520
agcaccagcg tgcagggccc ctgggagaga gccatcagcc caacaaagt gccctactac    2580 atcaaccacg agacccagac cacctgctgg gaccacccta agatgaccga gctgtaccag    2640
agcctggccg acctgaacaa tgtgcggttc agcgcctaca gaaccgccat gaagctgcgg    2700
agactgcaga aggccctgtg cctggacctg ctgtccctga gcgccgcctg cgacgccctg    2760
gaccagcaca acctgaagca gaacgaccag cccatggata tcctgcaggt gatcaactgc    2820
ctgaccacca tctacgatcg gctggagcag gagcacaaca acctggtgaa cgtgcccctg    2880
tgcgtggaca tgtgcctgaa ttggctgctg aacgtgtacg acaccggcag gaccggcaga    2940
atcagagtgc tgtccttcaa gaccggcatc atcagcctgt gcaaggccca cctggaggat    3000
aagtaccgct acctgttcaa gcaggtggcc agcagcaccg gcttctgcga tcagaggaga    3060
ctgggcctgc tgctgcacga tagcatccag atccctaggc agctgggcga ggtggccagc    3120
ttcggcggca gcaacatcga gcccagcgtg cggagctgct tccagttcgc caacaacaag    3180
cccgagatcg aggccgccct gttcctggac tggatgcggc tggaacccca gagcatggtc    3240
tggctgcccg tgctgcacag agtggctgcc gccgagaccg ccaagcacca ggccaagtgc    3300
aacatctgca aagagtgccc catcatcggc ttccggtaca gaagcctgaa gcacttcaac    3360
tacgacatct gccagagctg cttttttcagc ggcagagtgg ccaagggcca caagatgcac    3420 tacccccatgg tggagtactg cacccccacc acctccggcg aggacgtgcg ggacttcgcc    3480
aaggtgctga gaacaagtt ccggaccaag cggtactttg ccaagcaccc ccggatgggc    3540
tacctgcccg tgcagaccgt gctggaaggc gacaacatgg aaaccccgt gaccctgatc    3600 aacttctggc ccgtgacag cgcccctgcc agcagccccc agctgtccca cgacgacacc    3660
cacagccgga tcgagcacta cgccagccgg ctcgccgaga tggaaaacag caacggcagc    3720
```

| | |
|---|---:|
| tacctgaacg acagcatcag ccccaacgag agcatcgacg acgagcacct gctgatccag | 3780 |
| cactactgtc agagcctgaa ccaggacagc cccctgagcc agcccagaag ccctgcccag | 3840 |
| atcctgatca gcctggaaag cgaggaacgg ggcgagctgg aacggatcct ggccgacctg | 3900 |
| gaagaggaaa accggaacct gcaggccgag tacgaccggc tgaagcagca gcacgagcac | 3960 |
| aagggcctga gcccctgcc cagccccct gagatgatgc ccacctcccc ccagagcccc | 4020 |
| agggacgccg agctgatcgc cgaggccaag ctgctgcggc agcacaaggg gcggctggaa | 4080 |
| gcccggatgc agatcctgga agatcacaac aagcagctgg aaagccagct gcaccggctg | 4140 |
| agacagctgc tggaacagcc ccaggccgag gacaccatgt gatgatga | 4188 |

<210> SEQ ID NO 9
<211> LENGTH: 5239
<212> TYPE: DNA
<213> ORGANISM: Artificial Sequence
<220> FEATURE:
<223> OTHER INFORMATION: AAV ITR cMD3

<400> SEQUENCE: 9

| | |
|---|---:|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtggccaa ctccatcact | 120 |
| aggggttcct tgtagttaat gattaacccg ccatgctact tatctacgta gccatgctct | 180 |
| agacatggct cgacagatcg agctccaccg cggtggcggc cgtccgccct cggcaccatc | 240 |
| ctcacgacac ccaaatatgg cgacgggtga ggaatggtgg ggagttatttt ttagagcggt | 300 |
| gaggaaggtg ggcaggcagc aggtgttggc gctctaaaaa taactcccgg gagttatttt | 360 |
| tagagcggag gaatggtgga cacccaaata tggcgacggt tcctcacccg tcgccatatt | 420 |
| tgggtgtccg ccctcggccg gggccgcatt cctgggggcc gggcggtgct cccgcccgcc | 480 |
| tcgataaaag gctccggggc cggcggcggc ccacgagcta cccggaggag cgggaggcgc | 540 |
| caagctctag aactagtgga tcccccgggc tgcaggaatt cgccaccatg ctgtggtggg | 600 |
| aggaagtgga ggactgctac gagagagagg acgtgcagaa gaaaaccttc accaagtgga | 660 |
| tcaacgccca gttcagcaag ttcggcaagc agcacatcga gaacctgttc agcgatctgc | 720 |
| aggatggcag gagactgctg gatctgctgg agggactgac cggccagaag ctgcccaagg | 780 |
| agaagggcag caccagagtg cacgcccctga caacgtgaaa caaggccctg agagtgctgc | 840 |
| agaagaacaa cgtggacctg gtggatatcg gcagcaccga catcgtggac ggcaaccaca | 900 |
| agctgacccct gggcctgatc tggaacatca tcctgcactg gcaggtgaag aacgtgatga | 960 |
| agaacatcat ggccggcctg cagcagacca acagcgagaa gatcctgctg agctgggtga | 1020 |
| ggcagagcac cagaaactac ccccaggtga acgtgatcaa cttcaccacc tcctggagcg | 1080 |
| acggcctggc cctgaacgcc ctgatccaca gccacagacc cgacctgttc gactggaaca | 1140 |
| gcgtggtgtg tcagcagagc gccacccaga gactggagca cgccttcaac atcgccaagt | 1200 |
| accagctggg catcgagaag ctgctggacc ccgaggacgt ggccaccacc taccccgaca | 1260 |
| agaaaagcat cctgatgtat attaccagcc tgttccaggt gctgcccag caggtgtcca | 1320 |
| tcgaggccat ccaggaagtg gaaatgctgc ccaggcccag caaagtgacc agggaggagc | 1380 |
| acttccagct gcaccaccag atgcactata gccagcagat caccgtgtcc ctggccagg | 1440 |
| gctatgagag agccctagc agccccaagc ccggttcaa gagctacgcc tacacccagg | 1500 |
| ccgcctacgt gaccacctcc gaccccacca gaagcccct gcccagccag cacctggaga | 1560 |

```
cccctgagga taagagcttc ggcagaagcc tgaccgagac cgaggccaac ctggatagct    1620
accagaccgc cctggaggaa gtgctgtctt ggctgctgtc cgccgaggac gccctgcagg    1680
cccagggcga gatcagcaac gacgtggaag aagtgaagga gcagttccac acccacgagg    1740
gctacatgat ggacctgacc agccaccagg gcagagtggg caacgtgctg cagctgggca    1800
gccagctgat cggcaccggc aagctgagcg aggacgagga gaccgaagtg caggaacaga    1860
tgaacctgct gaacagcaga tgggagtgcc tgagagtggc cagcatggag aagcagagca    1920
acctgcacaa agtgctgatg gatctgcaga accagcagct gaaggagctg aacgactggc    1980
tgaccaagac agaggagcgg acccggaaga tggagaagga gcccctgggc cctgacatcg    2040
aggacctgaa gaggcaggtg cagcagcata aggtcctgca ggaggatctg gagcaggagc    2100
aggtgcgcgt gaacagcctg acccacatgg tggtcgtggt ggacgagagc agcggcgacc    2160
acgccacagc cgccctggaa gagcagctga aagtgctggg cggcagatgg gccaatatct    2220
gccggtggac cgaggacaga tgggtgctgc tgcaggacat cctgctgaag tggcagagat    2280
tcaccgagga gcagtgcctg tttagcgcct ggctgagcga aaggaggac gccgtgaaca    2340 agatccacac caccggcttc aaggaccaga gcgaagtgct gtccaacctg cagaagctgg    2400
ccgtgctgaa aaccgacctg gagaagaaaa agcagaccat ggacaagctg tgcagcctga    2460
accaggacct gctgagcgcc ctgaagaaca ccgtggtggc ccacaagatg gaggcctggc    2520
tggataatag cgctcagaga tgggataatc tggtgcagaa actggagaag agcagcgccc    2580
agatcagcca ggccgtgacc accacccagc ccagcctgac acagaccacc gtgatggaga    2640
ccgtgaccat ggtgaccacc agggagcaca tcctggtgaa gcacgccag gaggagctgc    2700 cccctccccc ccctcagaag aagcggcaga tcatcgtgga tgccctggag agactgcagg    2760
agctgcagga agccaccgac gagctggacc tgaagctgag acaggccgaa gtgatcaagg    2820
gcagctggca gcctgtgggc gatctgctga tcgacagcct gcaggaccac ctggagaaag    2880
tgaaggccct gcggggcgag accaccccc tgaaggagaa cgtgtcctac gtgaacgacc    2940
tggccagaca gctgaccacc ctgggcattc agctgagccc ctacaacctg aacaccctgg    3000
aggatctgaa cacccggtgg aaactgctgc aggtggccat tgaggaccgg atcaggcagc    3060
tgcacgaggc ccacagagac ttcggccctg cttctcagca tttcctgagc accagcgtgc    3120 agggccctg ggagagagcc atcagcccca caaagtgcc ctactacatc aaccacgaga    3180
cccagaccac ctgctgggac cacctaaga tgaccgagct gtaccagagc ctggccgacc    3240
tgaacaatgt gcggttcagc gcctacagaa ccgccatgaa gctgcggaga ctgcagaagg    3300
ccctgtgcct ggacctgctg tccctgagcg ccgcctgcga cgccctggac cagcacaacc    3360
tgaagcagaa cgaccagccc atggatatcc tgcaggtgat caactgcctg accaccatct    3420
acgatcggct ggagcaggag cacaacaacc tggtgaacgt gcccctgtgc gtggacatgt    3480
gcctgaattg gctgctgaac gtgtacgaca ccggcaggac cggcagaatc agagtgctgt    3540
ccttcaagac cggcatcatc agcctgtgca aggcccacct ggaggataag taccgctacc    3600
tgttcaagca ggtggccagc agcaccggct tctgcgatca gaggagactg ggcctgctgc    3660
tgcacgatag catccagatc cctaggcagc tgggcgaggt ggccagcttc ggcggcagca    3720
acatcgagcc cagcgtgcgg agctgcttcc agttcgccaa caacaagccc gagatcgagg    3780
ccgccctgtt cctggactgg atgcggctgg aaccccagag catggtctgg ctgcccgtgc    3840
tgcacagagt ggctgccgcc gagaccgcca agcaccaggc caagtgcaac atctgcaaag    3900
agtgccccat catcggcttc cggtacagaa gcctgaagca cttcaactac gacatctgcc    3960
```

```
agagctgctt tttcagcggc agagtggcca agggccacaa gatgcactac cccatggtgg   4020
agtactgcac ccccaccacc tccggcgagg acgtgcggga cttcgccaag gtgctgaaga   4080
acaagttccg gaccaagcgg tactttgcca agcaccccg  gatgggctac ctgcccgtgc   4140
agaccgtgct ggaaggcgac aacatggaaa cccccgtgac cctgatcaac ttctggcccg   4200
tggacagcgc ccctgccagc agccccagc  tgtcccacga cgacacccac agccggatcg   4260
agcactacgc cagccggctc gccgagatgg aaaacagcaa cggcagctac ctgaacgaca   4320
gcatcagccc caacgagagc atcgacgacg agcacctgct gatccagcac tactgtcaga   4380
gcctgaacca ggacagcccc ctgagccagc ccagaagccc tgcccagatc ctgatcagcc   4440
tggaaagcga ggaacggggc gagctggaac ggatcctggc cgacctggaa gaggaaaacc   4500
ggaacctgca ggccgagtac gaccggctga agcagcagca cgagcacaag ggcctgagcc   4560
ccctgcccag ccccctgag  atgatgccca cctccccca  gagccccagg gacgccgagc   4620
tgatcgccga ggccaagctg ctgcggcagc acaagggcg  gctggaagcc cggatgcaga   4680
tcctggaaga tcacaacaag cagctggaaa gccagctgca ccggctgaga cagctgctgg   4740
aacagcccca ggccgaggac accatgtgat gatgagcggc cgcttcccctt tagtgagggt   4800
taatgcttcg agcagacatg ataagataca ttgatgagtt tggacaaacc acaactagaa   4860
tgcagtgaaa aaaatgcttt atttgtgaaa tttgtgatgc tattgcttta tttgtaacca   4920
ttataagctg caataaacaa gttaacaaca acaattgcat tcatttatg  tttcaggttc   4980
aggggggagat gtgggaggtt ttttaaagca agtaaaacct ctacaaatgt ggtaaaatcc   5040
gataaggact agagcatggc tacgtagata agtagcatgg cgggttaatc attaactaca   5100
aggaacccct agtgatggag ttggccactc cctctctgcg cgctcgctcg ctcactgagg   5160
ccgggcgacc aaaggtcgcc cgacgcccgg gctttgcccg gcggcctcca gtgagcgagc   5220
gagcgcgcag ctggcgtaa                                                5239
```

<210> SEQ ID NO 10
<211> LENGTH: 1472
<212> TYPE: PRT
<213> ORGANISM: Artificial Sequence
<220> FEATURE:
<223> OTHER INFORMATION: canine MD4 (PRT)

<400> SEQUENCE: 10

```
Met Leu Trp Trp Glu Glu Val Glu Asp Cys Tyr Glu Arg Glu Asp Val
1               5                   10                  15

Gln Lys Lys Thr Phe Thr Lys Trp Ile Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Lys Asn Asn Val Asp Leu Val Asp Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125
```

```
Ala Gly Leu Gln Gln Thr Asn Ser Glu Lys Ile Leu Leu Ser Trp Val
130                 135                 140
Arg Gln Ser Thr Arg Asn Tyr Pro Gln Val Asn Val Ile Asn Phe Thr
145                 150                 155                 160
Thr Ser Trp Ser Asp Gly Leu Ala Leu Asn Ala Leu Ile His Ser His
                165                 170                 175
Arg Pro Asp Leu Phe Asp Trp Asn Ser Val Val Cys Gln Gln Ser Ala
            180                 185                 190
Thr Gln Arg Leu Glu His Ala Phe Asn Ile Ala Lys Tyr Gln Leu Gly
        195                 200                 205
Ile Glu Lys Leu Leu Asp Pro Glu Asp Val Ala Thr Thr Tyr Pro Asp
210                 215                 220
Lys Lys Ser Ile Leu Met Tyr Ile Thr Ser Leu Phe Gln Val Leu Pro
225                 230                 235                 240
Gln Gln Val Ser Ile Glu Ala Ile Gln Glu Val Met Leu Pro Arg
                245                 250                 255
Pro Ser Lys Val Thr Arg Glu Glu His Phe Gln Leu His His Gln Met
            260                 265                 270
His Tyr Ser Gln Gln Ile Thr Val Ser Leu Ala Gln Gly Tyr Glu Arg
        275                 280                 285
Ala Pro Ser Ser Pro Lys Pro Arg Phe Lys Ser Tyr Ala Tyr Thr Gln
290                 295                 300
Ala Ala Tyr Val Thr Thr Ser Asp Pro Thr Arg Ser Pro Leu Pro Ser
305                 310                 315                 320
Gln His Leu Glu Thr Pro Glu Asp Lys Ser Phe Gly Arg Ser Leu Thr
                325                 330                 335
Glu Thr Glu Ala Asn Leu Asp Ser Tyr Gln Thr Ala Leu Glu Glu Val
            340                 345                 350
Leu Ser Trp Leu Leu Ser Ala Glu Asp Ala Leu Gln Ala Gln Gly Glu
        355                 360                 365
Ile Ser Asn Asp Val Glu Val Lys Glu Gln Phe His Thr His Glu
370                 375                 380
Gly Tyr Met Met Asp Leu Thr Ser His Gln Gly Arg Val Gly Asn Val
385                 390                 395                 400
Leu Gln Leu Gly Ser Gln Leu Ile Gly Thr Gly Lys Leu Ser Glu Asp
                405                 410                 415
Glu Glu Thr Glu Val Gln Glu Gln Met Asn Leu Leu Asn Ser Arg Trp
            420                 425                 430
Glu Cys Leu Arg Val Ala Ser Met Glu Lys Gln Ser Asn Leu His Lys
        435                 440                 445
Val Leu Met Asp Leu Gln Asn Gln Gln Leu Lys Glu Leu Asn Asp Trp
450                 455                 460
Leu Thr Lys Thr Glu Glu Arg Thr Arg Lys Met Glu Lys Glu Pro Leu
465                 470                 475                 480
Gly Pro Asp Ile Glu Asp Leu Lys Arg Gln Val Gln Gln His Lys Val
                485                 490                 495
Leu Gln Glu Asp Leu Glu Gln Glu Gln Val Arg Val Asn Ser Leu Thr
            500                 505                 510
His Met Val Val Val Asp Glu Ser Ser Gly Asp His Ala Thr Ala
        515                 520                 525
Ala Leu Glu Glu Gln Leu Lys Val Leu Gly Gly Arg Trp Ala Asn Ile
530                 535                 540
Cys Arg Trp Thr Glu Asp Arg Trp Val Leu Leu Gln Asp Ile Leu Leu
```

-continued

```
           545                 550                 555                 560
        Lys Trp Gln Arg Phe Thr Glu Glu Gln Cys Leu Phe Ser Ala Trp Leu
                            565                 570                 575

Ser Glu Lys Glu Asp Ala Val Asn Lys Ile His Thr Thr Gly Phe Lys
                        580                 585                 590

Asp Gln Ser Glu Val Leu Ser Asn Leu Gln Lys Leu Ala Val Leu Lys
                    595                 600                 605

Thr Asp Leu Glu Lys Lys Gln Thr Met Asp Lys Leu Cys Ser Leu
                610                 615                 620

Asn Gln Asp Leu Leu Ser Ala Leu Lys Asn Thr Val Ala His Lys
        625                 630                 635                 640

Met Glu Ala Trp Leu Asp Asn Ser Ala Gln Arg Trp Asp Asn Leu Val
                            645                 650                 655

Gln Lys Leu Glu Lys Ser Ser Ala Gln Ile Ser Gln Ala Val Thr Thr
                        660                 665                 670

Thr Gln Pro Ser Leu Thr Gln Thr Thr Val Met Glu Thr Val Thr Met
                    675                 680                 685

Val Thr Thr Arg Glu His Ile Leu Val Lys His Ala Gln Glu Glu Leu
                690                 695                 700

Pro Pro Pro Pro Gln Lys Lys Arg Gln Ile Ile Val Asp Ala Leu
        705                 710                 715                 720

Glu Arg Leu Gln Glu Leu Gln Glu Ala Thr Asp Glu Leu Asp Leu Lys
                            725                 730                 735

Leu Arg Gln Ala Glu Val Ile Lys Gly Ser Trp Gln Pro Val Gly Asp
                        740                 745                 750

Leu Leu Ile Asp Ser Leu Gln Asp His Leu Glu Lys Val Lys Ala Leu
                    755                 760                 765

Arg Gly Glu Thr Thr Pro Leu Lys Glu Asn Val Ser Tyr Val Asn Asp
                770                 775                 780

Leu Ala Arg Gln Leu Thr Thr Leu Gly Ile Gln Leu Ser Pro Tyr Asn
        785                 790                 795                 800

Leu Asn Thr Leu Glu Asp Leu Asn Thr Arg Trp Lys Leu Leu Gln Val
                            805                 810                 815

Ala Ile Glu Asp Arg Ile Arg Gln Leu His Glu Ala His Arg Asp Phe
                        820                 825                 830

Gly Pro Ala Ser Gln His Phe Leu Ser Thr Ser Val Gln Gly Pro Trp
                    835                 840                 845

Glu Arg Ala Ile Ser Pro Asn Lys Val Pro Tyr Tyr Ile Asn His Glu
                850                 855                 860

Thr Gln Thr Thr Cys Trp Asp His Pro Lys Met Thr Glu Leu Tyr Gln
        865                 870                 875                 880

Ser Leu Ala Asp Leu Asn Asn Val Arg Phe Ser Ala Tyr Arg Thr Ala
                            885                 890                 895

Met Lys Leu Arg Arg Leu Gln Lys Ala Leu Cys Leu Asp Leu Leu Ser
                        900                 905                 910

Leu Ser Ala Ala Cys Asp Ala Leu Asp Gln His Asn Leu Lys Gln Asn
                    915                 920                 925

Asp Gln Pro Met Asp Ile Leu Gln Val Ile Asn Cys Leu Thr Thr Ile
                930                 935                 940

Tyr Asp Arg Leu Glu Gln Glu His Asn Asn Leu Val Asn Val Pro Leu
        945                 950                 955                 960

Cys Val Asp Met Cys Leu Asn Trp Leu Leu Asn Val Tyr Asp Thr Gly
                            965                 970                 975
```

```
Arg Thr Gly Arg Ile Arg Val Leu Ser Phe Lys Thr Gly Ile Ile Ser
            980                 985                 990

Leu Cys Lys Ala His Leu Glu Asp Lys Tyr Arg Tyr Leu Phe Lys Gln
        995                1000                1005

Val Ala Ser Ser Thr Gly Phe Cys Asp Gln Arg Arg Leu Gly Leu Leu
   1010                1015                1020

Leu His Asp Ser Ile Gln Ile Pro Arg Gln Leu Gly Glu Val Ala Ser
1025                1030                1035                1040

Phe Gly Gly Ser Asn Ile Glu Pro Ser Val Arg Ser Cys Phe Gln Phe
                1045                1050                1055

Ala Asn Asn Lys Pro Glu Ile Glu Ala Ala Leu Phe Leu Asp Trp Met
            1060                1065                1070

Arg Leu Glu Pro Gln Ser Met Val Trp Leu Pro Val Leu His Arg Val
        1075                1080                1085

Ala Ala Ala Glu Thr Ala Lys His Gln Ala Lys Cys Asn Ile Cys Lys
   1090                1095                1100

Glu Cys Pro Ile Ile Gly Phe Arg Tyr Arg Ser Leu Lys His Phe Asn
1105                1110                1115                1120

Tyr Asp Ile Cys Gln Ser Cys Phe Phe Ser Gly Arg Val Ala Lys Gly
                1125                1130                1135

His Lys Met His Tyr Pro Met Val Glu Tyr Cys Thr Pro Thr Thr Ser
            1140                1145                1150

Gly Glu Asp Val Arg Asp Phe Ala Lys Val Leu Lys Asn Lys Phe Arg
        1155                1160                1165

Thr Lys Arg Tyr Phe Ala Lys His Pro Arg Met Gly Tyr Leu Pro Val
   1170                1175                1180

Gln Thr Val Leu Glu Gly Asp Asn Met Glu Thr Pro Val Thr Leu Ile
1185                1190                1195                1200

Asn Phe Trp Pro Val Asp Ser Ala Pro Ala Ser Ser Pro Gln Leu Ser
                1205                1210                1215

His Asp Asp Thr His Ser Arg Ile Glu His Tyr Ala Ser Arg Leu Ala
            1220                1225                1230

Glu Met Glu Asn Ser Asn Gly Ser Tyr Leu Asn Asp Ser Ile Ser Pro
        1235                1240                1245

Asn Glu Ser Ile Asp Asp Glu His Leu Leu Ile Gln His Tyr Cys Gln
   1250                1255                1260

Ser Leu Asn Gln Asp Ser Pro Leu Ser Gln Pro Arg Ser Pro Ala Gln
1265                1270                1275                1280

Ile Leu Ile Ser Leu Glu Ser Glu Glu Arg Gly Glu Leu Glu Arg Ile
                1285                1290                1295

Leu Ala Asp Leu Glu Glu Glu Asn Arg Asn Leu Gln Ala Glu Tyr Asp
            1300                1305                1310

Arg Leu Lys Gln Gln His Glu His Lys Gly Leu Ser Pro Leu Pro Ser
        1315                1320                1325

Pro Pro Glu Met Met Pro Thr Ser Pro Gln Ser Pro Arg Asp Ala Glu
   1330                1335                1340

Leu Ile Ala Glu Ala Lys Leu Leu Arg Gln His Lys Gly Arg Leu Glu
1345                1350                1355                1360

Ala Arg Met Gln Ile Leu Glu Asp His Asn Lys Gln Leu Glu Ser Gln
                1365                1370                1375

Leu His Arg Leu Arg Gln Leu Leu Glu Gln Pro Gln Ala Glu Ala Lys
            1380                1385                1390
```

```
Val Asn Gly Thr Thr Val Ser Ser Pro Ser Thr Ser Leu Gln Arg Ser
         1395                1400                1405

Asp Ser Ser Gln Pro Met Leu Leu Arg Val Val Gly Ser Gln Thr Ser
    1410                1415                1420

Glu Ser Met Gly Glu Glu Asp Leu Leu Ser Pro Pro Gln Asp Thr Ser
1425                1430                1435                1440

Thr Gly Leu Glu Glu Val Met Glu Gln Leu Asn His Ser Phe Pro Ser
            1445                1450                1455

Ser Arg Gly Arg Asn Thr Pro Gly Lys Pro Met Arg Glu Asp Thr Met
        1460                1465                1470

<210> SEQ ID NO 11
<211> LENGTH: 4425
<212> TYPE: DNA
<213> ORGANISM: Artificial Sequence
<220> FEATURE:
<223> OTHER INFORMATION: canine MD4 (cDNA)

<400> SEQUENCE: 11
```

| | | | | | |
|---|---|---|---|---|---|
| atgctgtggt | gggaggaagt | ggaggactgc | tacgagagag | aggacgtgca | gaagaaaacc | 60 |
| ttcaccaagt | ggatcaacgc | ccagttcagc | aagttcggca | agcagcacat | cgagaacctg | 120 |
| ttcagcgatc | tgcaggatgg | caggagactg | ctggatctgc | tggagggact | gaccggccag | 180 |
| aagctgccca | ggagaagggg | cagcaccaga | gtgcacgccc | tgaacaacgt | gaacaaggcc | 240 |
| ctgagagtgc | tgcagaagaa | caacgtggac | ctggtggata | tcggcagcac | cgacatcgtg | 300 |
| gacggcaacc | acaagctgac | cctgggcctg | atctggaaca | tcatcctgca | ctggcaggtg | 360 |
| aagaacgtga | tgaagaacat | catggccggc | tgcagcagca | ccaacagcga | agatcctg | 420 |
| ctgagctggg | tgaggcagag | caccagaaac | taccccagg | tgaacgtgat | caacttcacc | 480 |
| acctcctgga | gcgacggcct | ggccctgaac | gccctgatcc | acagccacag | acccgacctg | 540 |
| ttcgactgga | cagcgtggt | gtgtcagcag | agcgccaccc | agagactgga | gcacgccttc | 600 |
| aacatcgcca | gtaccagct | gggcatcgag | aagctgctgg | accccgagga | cgtggccacc | 660 |
| acctaccccg | acaagaaaag | catcctgatg | tatattacca | gcctgttcca | ggtgctgccc | 720 |
| cagcaggtgt | ccatcgaggc | catccaggaa | gtggaaatgc | tgcccaggcc | cagcaaagtg | 780 |
| accagggagg | agcacttcca | gctgcaccac | cagatgcact | atagccagca | gatcaccgtg | 840 |
| tccctggccc | agggctatga | gagagcccct | agcagcccca | gcccggtt | caagagctac | 900 |
| gcctacaccc | aggccgccta | cgtgaccacc | tccgacccca | ccagaagccc | cctgcccagc | 960 |
| cagcacctgg | agaccctga | ggataagagc | ttcggcagaa | gcctgaccga | gaccgaggcc | 1020 |
| aacctggata | gctaccagac | cgccctggag | gaagtgctgt | cttggctgct | gtccgccgag | 1080 |
| gacgccctgc | aggcccaggg | cgagatcagc | aacgacgtgg | aagaagtgaa | ggagcagttc | 1140 |
| cacacccacg | agggctacat | gatggacctg | accagccacc | agggcagagt | gggcaacgtg | 1200 |
| ctgcagctgg | cagccagct | gatcggcacc | ggcaagctga | gcgaggacga | ggagaccgaa | 1260 |
| gtgcaggaac | agatgaacct | gctgaacagc | agatgggagt | gcctgagagt | ggccagcatg | 1320 |
| gagaagcaga | gcaacctgca | caaagtgctg | atggatctgc | agaaccagca | gctgaaggag | 1380 |
| ctgaacgact | ggctgaccaa | gacagaggag | cggacccga | agatggagaa | ggagcccctg | 1440 |
| ggccctgaca | tcgaggacct | gaagaggcag | gtgcagcagc | ataaggtcct | gcaggaggat | 1500 |
| ctggagcagg | agcaggtgcg | cgtgaacagc | ctgacccaca | tggtggtcgt | ggtgacgag | 1560 |
| agcagcggcg | accacgccac | agccgccctg | gaagagcagc | tgaaagtgct | gggcggcaga | 1620 |

```
tgggccaata tctgccggtg gaccgaggac agatgggtgc tgctgcagga catcctgctg  1680
aagtggcaga gattcaccga ggagcagtgc ctgtttagcg cctggctgag cgagaaggag  1740
gacgccgtga acaagatcca caccaccggc ttcaaggacc agagcgaagt gctgtccaac  1800
ctgcagaagc tggccgtgct gaaaaccgac tggagaaga aaaagcagac catggacaag  1860
ctgtgcagcc tgaaccagga cctgctgagc gccctgaaga caccgtggt ggcccacaag  1920 atggaggcct ggctggataa tagcgctcag agatgggata tctggtgca gaaactggag  1980 aagagcagcg cccagatcag ccaggccgtg accaccaccc agcccagcct gacacagacc  2040
accgtgatgg agaccgtgac catggtgacc accagggagc acatcctggt gaagcacgcc  2100
caggaggagc tgccccctcc ccccccctcag aagaagcggc agatcatcgt ggatgccctg  2160
gagagactgc aggagctgca ggaagccacc gacgagctgg acctgaagct gagacaggcc  2220
gaagtgatca agggcagctg gcagcctgtg ggcgatctgc tgatcgacag cctgcaggac  2280
cacctgagag aagtgaaggc cctgcggggc gagaccaccc ccctgaagga gaacgtgtcc  2340
tacgtgaacg acctggccag acagctgacc accctgggca ttcagctgag ccctacaac  2400 ctgaacaccc tggaggatct gaacacccgg tggaaactgc tgcaggtggc cattgaggac  2460
cggatcaggc agctgcacga ggcccacaga gacttcggcc ctgcttctca gcatttcctg  2520
agcaccagcg tgcagggccc ctgggagaga gccatcagcc ccaacaaagt gccctactac  2580
atcaaccacg agacccagac cacctgctgg gaccacccta agatgaccga gctgtaccag  2640
agcctggccg acctgaacaa tgtgcggttc agcgcctaca gaaccgccat gaagctgcgg  2700
agactgcaga aggccctgtg cctggacctg ctgtccctga gcgccgcctg cgacgccctg  2760
gaccagcaca acctgaagca gaacgaccag cccatggata tcctgcaggt gatcaactgc  2820
ctgaccacca tctacgatcg gctggagcag gagcacaaca acctggtgaa cgtgcccctg  2880
tgcgtggaca tgtgcctgaa ttggctgctg aacgtgacg acaccggcag gaccggcaga  2940
atcagagtgc tgtccttcaa gaccggcatc atcagcctgt gcaaggccca cctggaggat  3000
aagtaccgct acctgttcaa gcaggtggcc agcagcaccg gcttctgcga tcagaggaga  3060
ctgggcctgc tgctgcacga tagcatccag atccctaggc agctgggcga ggtggccagc  3120
ttcggcggca gcaacatcga gcccagcgtg cggagctgct tccagttcgc caacaacaag  3180
cccgagatcg aggccgccct gttcctggac tggatgcggc tggaacccca gagcatggtc  3240
tggctgcccg tgctgcacag agtggctgcc gccgagaccg ccaagcacca ggccaagtgc  3300
aacatctgca aagagtgccc catcatcggc ttccggtaca gaagcctgaa gcacttcaac  3360
tacgacatct gccagagctg ctttttcagc ggcagagtgg ccaagggcca caagatgcac  3420 tacccccatgg tggagtactg cacccccacc acctccggcg aggacgtgcg ggacttcgcc  3480
aaggtgctga agaacaagtt ccggaccaag cggtactttg ccaagcaccc ccggatgggc  3540
tacctgcccg tgcagaccgt gctggaaggc gacaacatgg aaacccccgt gaccctgatc  3600
aacttctggc ccgtggacag cgcccctgcc agcagccccc agctgtccca cgacgacacc  3660
cacagccgga tcgagcacta cgccagccgg ctcgccgaga tggaaaacag caacggcagc  3720
tacctgaacg acagcatcag ccccaacgag agcatcgacg acgagcacct gctgatccag  3780
cactactgtc agagcctgaa ccaggacagc cccctgagcc agcccagaag ccctgcccag  3840
atcctgatca gcctggaaag cgaggaacgg ggcgagctgg aacggatcct ggccgacctg  3900
gaagaggaaa accggaacct gcaggccgag tacgaccggc tgaagcagca gcacgagcac  3960
aagggcctga gccccctgcc cagccccccct gagatgatgc ccacctcccc ccagagcccc  4020
```

```
agggacgccg agctgatcgc cgaggccaag ctgctgcggc agcacaaggg gcggctggaa    4080
gcccggatgc agatcctgga agatcacaac aagcagctgg aaagccagct gcaccggctg    4140
agacagctgc tggaacagcc ccaggccgaa gccaaggtga acggcaccac cgtgagcagc    4200
cccagcacca gcctgcagcg gagcgacagc tctcagccaa tgctcctgcg ggtggtgggc    4260
tctcagacca gcgagagcat gggcgaagag gacctgctgt ccccacctca agacaccagc    4320
accggcctgg aagaagtgat ggaacagctg aaccacagct tccccagcag ccggggcaga    4380 aacaccccg gcaagcccat gcgggaggac accatgtgat gatga    4425
```

<210> SEQ ID NO 12
<211> LENGTH: 5463
<212> TYPE: DNA
<213> ORGANISM: Artificial Sequence
<220> FEATURE:
<223> OTHER INFORMATION: AAV ITR cMD4

<400> SEQUENCE: 12

```
gcgcgctcgc tcgctcactg aggccgcccg ggcaaagccc gggcgtcggg cgacctttgg      60
tcgcccggcc tcagtgagcg agcgagcgcg cagagaggga gtggccaact ccatcactag     120
gggttccttg tagttaatga ttaacccgcc atgctactta tctacgtagc catgctctag     180
acatggctcg acagatcgag ctccaccgcg gtggcggccg tccgccctcg gcaccatcct     240
cacgacaccc aaatatggcg acgggtgagg aatggtgggg agttattttt agagcggtga     300
ggaaggtggg caggcagcag gtgttggcgc tctaaaaata actcccggga gttattttta     360
gagcggagga atggtggaca cccaaatatg gcgacggttc ctcacccgtc gccatatttg     420
ggtgtccgcc ctcggccggg gccgcattcc tgggggccgg gcgtgctcc cgcccgcctc      480 gataaaaggc tccggggccg gcggcggccc acagctacc ggaggagcg ggaggcgcca      540 agctctagaa ctagtggatc ccccgggctg caggaattcg ccaccatgct gtggtgggag    600
gaagtggagg actgctacga gagagaggac gtgcagaaga aaaccttcac caagtggatc    660
aacgcccagt tcagcaagtt cggcaagcag cacatcgaga acctgttcag cgatctgcag    720
gatggcagga gactgctgga tctgctggag ggactgaccg ccagaagct gcccaaggag    780 aagggcagca ccagagtgca cgccctgaac aacgtgaaca aggccctgag agtgctgcag    840
aagaacaacg tggacctggt ggatatcggc agcaccgaca tcgtgacgg caaccacaag    900 ctgaccctgg gcctgatctg gaacatcatc ctgcactggc aggtgaagaa cgtgatgaag    960
aacatcatgg ccgcctgca gcagaccaac agcgagaaga tcctgctgag ctgggtgagg    1020
cagagcacca gaaactaccc ccaggtgaac gtgatcaact tcaccacctc ctggagcgac    1080
ggcctggccc tgaacgccct gatccacagc cacagaccg acctgttcga ctggaacagc    1140
gtggtgtgtc agcagagcgc caccagaga ctggagcacg ccttcaacat cgccaagtac    1200
cagctgggca tcgagaagct gctggacccc gaggacgtgg ccaccaccta ccccgacaag    1260
aaaagcatcc tgatgtatat taccagcctg ttccaggtgc tgcccagca ggtgtccatc    1320 gaggccatcc aggaagtgga aatgctgccc aggcccagca agtgaccag ggaggagcac    1380 ttccagctgc accaccagat gcactatagc agcagatca ccgtgtccct ggcccagggc    1440
tatgagagag cccctagcag ccccaagccc cggttcaaga gctacgccta cacccaggcc    1500
gcctacgtga ccacctccga ccccaccaga agccccctgc ccagccagca cctggagacc    1560
cctgaggata agagcttcgg cagaagcctg accgagaccg aggccaacct ggatagctac    1620
```

```
cagaccgccc tggaggaagt gctgtcttgg ctgctgtccg ccgaggacgc cctgcaggcc    1680
cagggcgaga tcagcaacga cgtggaagaa gtgaaggagc agttccacac ccacgagggc    1740
tacatgatgg acctgaccag ccaccagggc agagtgggca acgtgctgca gctgggcagc    1800
cagctgatcg gcaccggcaa gctgagcgag gacgaggaga ccgaagtgca ggaacagatg    1860
aacctgctga cagcagatg ggagtgcctg agagtggcca gcatggagaa gcagagcaac    1920
ctgcacaaag tgctgatgga tctgcagaac cagcagctga aggagctgaa cgactggctg    1980
accaagacag aggagcggac ccggaagatg gagaaggagc ccctgggccc tgacatcgag    2040
gacctgaaga ggcaggtgca gcagcataag gtcctgcagg aggatctgga gcaggagcag    2100
gtgcgcgtga acagcctgac ccacatggtg gtcgtggtgg acgagagcag cggcgaccac    2160
gccacagccg ccctggaaga gcagctgaaa gtgctgggcg cagatgggc caatatctgc    2220 cggtggaccg aggacagatg ggtgctgctg caggacatcc tgctgaagtg gcagagattc    2280
accgaggagc agtgcctgtt tagcgcctgg ctgagcgaga aggaggacgc cgtgaacaag    2340
atccacacca ccggcttcaa ggaccagagc gaagtgctgt ccaacctgca gaagctggcc    2400
gtgctgaaaa ccgacctgga gaagaaaaag cagaccatgg acaagctgtg cagcctgaac    2460
caggacctgc tgagcgccct gaagaacacc gtggtggccc acaagatgga ggcctggctg    2520
gataatagcg ctcagagatg ggataatctg gtgcagaaac tggagaagag cagcgcccag    2580
atcagccagg ccgtgaccac cacccagccc agcctgacac agaccaccgt gatggagacc    2640
gtgaccatgg tgaccaccag ggagcacatc ctggtgaagc acgcccagga ggagctgccc    2700
cctccccccc ctcagaagaa gcggcagatc atcgtggatg ccctggagag actgcaggag    2760
ctgcaggaag ccaccgacga gctggacctg aagctgagac aggccgaagt gatcaagggc    2820
agctggcagc ctgtgggcga tctgctgatc gacagcctgc aggaccacct ggagaaagtg    2880
aaggccctgc ggggcgagac cacccccctg aaggagaacg tgtcctacgt gaacgacctg    2940
gccagacagc tgaccaccct gggcattcag ctgagcccct acaacctgaa caccctggag    3000
gatctgaaca cccggtggaa actgctgcag gtggccattg aggaccggat caggcagctg    3060
cacgaggccc acagagactt cggccctgct tctcagcatt tcctgagcac cagcgtgcag    3120 ggccctggg agagagccat cagccccaac aaagtgccct actacatcaa ccacgagacc    3180
cagaccacct gctgggacca ccctaagatg accgagctgt accagagcct ggccgacctg    3240
aacaatgtgc ggttcagcgc ctacagaacc gccatgaagc tgcggagact gcagaaggcc    3300
ctgtgcctgg acctgctgtc cctgagcgcc gcctgcgacg ccctggacca gcacaacctg    3360
aagcagaacg accagcccat ggatatcctg caggtgatca actgcctgac caccatctac    3420
gatcggctgg agcaggagca caacaacctg gtgaacgtgc ccctgtgcgt ggacatgtgc    3480
ctgaattggc tgctgaacgt gtacgacacc ggcaggaccg gcagaatcag agtgctgtcc    3540
ttcaagaccg gcatcatcag cctgtgcaag gcccacctgg aggataagta ccgctacctg    3600
ttcaagcagg tggccagcag caccggcttc tgcgatcaga ggagactggg cctgctgctg    3660
cacgatagca tccagatccc taggcagctg ggcgaggtgg ccagcttcgg cggcagcaac    3720
atcgagccca gcgtgcggag ctgcttccag ttcgccaaca acaagcccga gatcgaggcc    3780
gccctgttcc tggactggat gcggctggaa ccccagcagc tggtctggct gcccgtgctg    3840
cacagagtgg ctgccgccga gaccgccaag caccaggcca gtgcaacat ctgcaaagag    3900 tgccccatca tcggcttccg gtacagaagc ctgaagcact tcaactacga catctgccag    3960
agctgctttt tcagcggcag agtggccaag ggccacaaga tgcactaccc catggtggag    4020
```

```
tactgcaccc ccaccacctc cggcgaggac gtgcgggact tcgccaaggt gctgaagaac    4080
aagttccgga ccaagcggta ctttgccaag caccccgga tgggctacct gcccgtgcag    4140
accgtgctgg aaggcgacaa catggaaacc cccgtgaccc tgatcaactt ctggcccgtg    4200
gacagcgccc ctgccagcag ccccagctg tcccacgacg acaccacag ccggatcgag    4260 cactacgcca gccggctcgc cgagatggaa acagcaacg gcagctacct gaacgacagc    4320
atcagcccca cgagagcat cgacgacgag cacctgctga tccagcacta ctgtcagagc    4380
ctgaaccagg acagccccct gagccagccc agaagccctg cccagatcct gatcagcctg    4440
gaaagcgagg aacggggcga gctggaacgg atcctggccg acctggaaga ggaaaaccgg    4500
aacctgcagg ccgagtacga ccggctgaag cagcagcacg agcacaaggg cctgagcccc    4560
ctgcccagcc ccctgagat gatgcccacc tcccccaga gccccaggga cgccgagctg    4620
atcgccgagg ccaagctgct gcggcagcac aaggggcggc tggaagcccg gatgcagatc    4680
ctggaagatc acaacaagca gctggaaagc cagctgcacc ggctgagaca gctgctggaa    4740 cagcccagg ccgaagccaa ggtgaacggc accaccgtga gcagccccag caccagcctg    4800
cagcggagcg acagctctca gccaatgctc ctgcgggtgg tgggctctca gaccagcgag    4860
agcatgggcg aagaggacct gctgtcccca cctcaagaca ccagcaccgg cctggaagaa    4920
gtgatggaac agctgaacca cagcttcccc agcagccggg gcagaaacac ccccggcaag    4980
cccatgcggg aggacaccat gtgatgatga gcggccgctt ccctttagtg agggttaatg    5040
cttcgagcag acatgataag atacattgat gagtttggac aaaccacaac tagaatgcag    5100
tgaaaaaaat gctttatttg tgaaatttgt gatgctattg ctttatttgt aaccattata    5160
agctgcaata acaagttaa caacaacaat tgcattcatt ttatgtttca ggttcagggg    5220
gagatgtggg aggttttta aagcaagtaa aacctctaca aatgtggtaa aatccgataa    5280
ggactagagc atggctacgt agataagtag catggcgggt taatcattaa ctacaaggaa    5340
cccctagtga tggagttggc cactccctct ctgcgcgctc gctcgctcac tgaggccggg    5400
cgaccaaagg tcgcccgacg cccgggcttt gcccgggcgg cctcagtgag cgagcgagcg    5460
cgc                                                                  5463
```

<210> SEQ ID NO 13
<211> LENGTH: 1392
<212> TYPE: PRT
<213> ORGANISM: Artificial Sequence
<220> FEATURE:
<223> OTHER INFORMATION: human MD3 (PRT)

<400> SEQUENCE: 13

```
Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
                20                  25                  30

Gly Lys Gln His Ile Glu Asn Leu Phe Ser Asp Leu Gln Asp Gly Arg
            35                  40                  45

Arg Leu Leu Asp Leu Leu Glu Gly Leu Thr Gly Gln Lys Leu Pro Lys
        50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95
```

```
Thr Asp Ile Val Asp Gly Asn His Lys Leu Thr Leu Gly Leu Ile Trp
            100                 105                 110
Asn Ile Ile Leu His Trp Gln Val Lys Asn Val Met Lys Asn Ile Met
        115                 120                 125
Ala Gly Leu Gln Gln Thr Asn Ser Glu Lys Ile Leu Leu Ser Trp Val
    130                 135                 140
Arg Gln Ser Thr Arg Asn Tyr Pro Gln Val Asn Val Ile Asn Phe Thr
145                 150                 155                 160
Thr Ser Trp Ser Asp Gly Leu Ala Leu Asn Ala Leu Ile His Ser His
                165                 170                 175
Arg Pro Asp Leu Phe Asp Trp Asn Ser Val Val Cys Gln Gln Ser Ala
            180                 185                 190
Thr Gln Arg Leu Glu His Ala Phe Asn Ile Ala Arg Tyr Gln Leu Gly
        195                 200                 205
Ile Glu Lys Leu Leu Asp Pro Glu Asp Val Asp Thr Thr Tyr Pro Asp
    210                 215                 220
Lys Lys Ser Ile Leu Met Tyr Ile Thr Ser Leu Phe Gln Val Leu Pro
225                 230                 235                 240
Gln Gln Val Ser Ile Glu Ala Ile Gln Glu Val Glu Met Leu Pro Arg
                245                 250                 255
Pro Pro Lys Val Thr Lys Glu Glu His Phe Gln Leu His His Gln Met
            260                 265                 270
His Tyr Ser Gln Gln Ile Thr Val Ser Leu Ala Gln Gly Tyr Glu Arg
        275                 280                 285
Thr Ser Ser Pro Lys Pro Arg Phe Lys Ser Tyr Ala Tyr Thr Gln Ala
    290                 295                 300
Ala Tyr Val Thr Thr Ser Asp Pro Thr Arg Ser Pro Phe Pro Ser Gln
305                 310                 315                 320
His Leu Glu Ala Pro Glu Asp Lys Ser Phe Gly Ser Ser Leu Met Glu
                325                 330                 335
Ser Glu Val Asn Leu Asp Arg Tyr Gln Thr Ala Leu Glu Glu Val Leu
            340                 345                 350
Ser Trp Leu Leu Ser Ala Glu Asp Thr Leu Gln Ala Gln Gly Glu Ile
        355                 360                 365
Ser Asn Asp Val Glu Val Val Lys Asp Gln Phe His Thr His Glu Gly
    370                 375                 380
Tyr Met Met Asp Leu Thr Ala His Gln Gly Arg Val Gly Asn Ile Leu
385                 390                 395                 400
Gln Leu Gly Ser Lys Leu Ile Gly Thr Gly Lys Leu Ser Glu Asp Glu
                405                 410                 415
Glu Thr Glu Val Gln Glu Gln Met Asn Leu Leu Asn Ser Arg Trp Glu
            420                 425                 430
Cys Leu Arg Val Ala Ser Met Glu Lys Gln Ser Asn Leu His Arg Val
        435                 440                 445
Leu Met Asp Leu Gln Asn Gln Lys Leu Lys Glu Leu Asn Asp Trp Leu
    450                 455                 460
Thr Lys Thr Glu Glu Arg Thr Arg Lys Met Glu Glu Pro Leu Gly
465                 470                 475                 480
Pro Asp Leu Glu Asp Leu Lys Arg Gln Val Gln Gln His Lys Val Leu
                485                 490                 495
Gln Glu Asp Leu Glu Gln Glu Gln Val Arg Val Asn Ser Leu Thr His
            500                 505                 510
Met Val Val Val Val Asp Glu Ser Ser Gly Asp His Ala Thr Ala Ala
```

```
            515                 520                 525
Leu Glu Glu Gln Leu Lys Val Leu Gly Asp Arg Trp Ala Asn Ile Cys
530                 535                 540

Arg Trp Thr Glu Asp Arg Trp Val Leu Leu Gln Asp Ile Leu Leu Lys
545                 550                 555                 560

Trp Gln Arg Leu Thr Glu Gln Cys Leu Phe Ser Ala Trp Leu Ser
                    565                 570                 575

Glu Lys Glu Asp Ala Val Asn Lys Ile His Thr Thr Gly Phe Lys Asp
                580                 585                 590

Gln Asn Glu Met Leu Ser Ser Leu Gln Lys Leu Ala Val Leu Lys Ala
                    595                 600                 605

Asp Leu Glu Lys Lys Lys Gln Ser Met Gly Lys Leu Tyr Ser Leu Lys
610                 615                 620

Gln Asp Leu Leu Ser Thr Leu Lys Asn Lys Ser Val Thr Gln Lys Thr
625                 630                 635                 640

Glu Ala Trp Leu Asp Asn Phe Ala Arg Cys Trp Asp Asn Leu Val Gln
                    645                 650                 655

Lys Leu Glu Lys Ser Thr Ala Gln Ile Ser Gln Ala Val Thr Thr Thr
                660                 665                 670

Gln Pro Ser Leu Thr Gln Thr Thr Val Met Glu Thr Val Thr Thr Val
            675                 680                 685

Thr Thr Arg Glu Gln Ile Leu Val Lys His Ala Gln Glu Glu Leu Pro
690                 695                 700

Pro Pro Pro Pro Gln Lys Lys Arg Gln Ile Thr Val Asp Thr Leu Glu
705                 710                 715                 720

Arg Leu Gln Glu Leu Gln Glu Ala Thr Asp Glu Leu Asp Leu Lys Leu
                    725                 730                 735

Arg Gln Ala Glu Val Ile Lys Gly Ser Trp Gln Pro Val Gly Asp Leu
                740                 745                 750

Leu Ile Asp Ser Leu Gln Asp His Leu Glu Lys Val Lys Ala Leu Arg
            755                 760                 765

Gly Glu Ile Ala Pro Leu Lys Glu Asn Val Ser His Val Asn Asp Leu
770                 775                 780

Ala Arg Gln Leu Thr Thr Leu Gly Ile Gln Leu Ser Pro Tyr Asn Leu
785                 790                 795                 800

Ser Thr Leu Glu Asp Leu Asn Thr Arg Trp Lys Leu Leu Gln Val Ala
                    805                 810                 815

Val Glu Asp Arg Val Arg Gln Leu His Glu Ala His Arg Asp Phe Gly
                820                 825                 830

Pro Ala Ser Gln His Phe Leu Ser Thr Ser Val Gln Gly Pro Trp Glu
            835                 840                 845

Arg Ala Ile Ser Pro Asn Lys Val Pro Tyr Tyr Ile Asn His Glu Thr
850                 855                 860

Gln Thr Thr Cys Trp Asp His Pro Lys Met Thr Glu Leu Tyr Gln Ser
865                 870                 875                 880

Leu Ala Asp Leu Asn Asn Val Arg Phe Ser Ala Tyr Arg Thr Ala Met
                    885                 890                 895

Lys Leu Arg Arg Leu Gln Lys Ala Leu Cys Leu Asp Leu Leu Ser Leu
                900                 905                 910

Ser Ala Ala Cys Asp Ala Leu Asp Gln His Asn Leu Lys Gln Asn Asp
            915                 920                 925

Gln Pro Met Asp Ile Leu Gln Ile Ile Asn Cys Leu Thr Thr Ile Tyr
930                 935                 940
```

```
Asp Arg Leu Glu Gln Glu His Asn Asn Leu Val Asn Val Pro Leu Cys
945                 950                 955                 960

Val Asp Met Cys Leu Asn Trp Leu Leu Asn Val Tyr Asp Thr Gly Arg
            965                 970                 975

Thr Gly Arg Ile Arg Val Leu Ser Phe Lys Thr Gly Ile Ile Ser Leu
        980                 985                 990

Cys Lys Ala His Leu Glu Asp Lys Tyr Arg Tyr Leu Phe Lys Gln Val
    995                 1000                1005

Ala Ser Ser Thr Gly Phe Cys Asp Gln Arg Arg Leu Gly Leu Leu Leu
1010                1015                1020

His Asp Ser Ile Gln Ile Pro Arg Gln Leu Gly Glu Val Ala Ser Phe
1025                1030                1035                1040

Gly Gly Ser Asn Ile Glu Pro Ser Val Arg Ser Cys Phe Gln Phe Ala
                1045                1050                1055

Asn Asn Lys Pro Glu Ile Glu Ala Ala Leu Phe Leu Asp Trp Met Arg
                1060                1065                1070

Leu Glu Pro Gln Ser Met Val Trp Leu Pro Val Leu His Arg Val Ala
            1075                1080                1085

Ala Ala Glu Thr Ala Lys His Gln Ala Lys Cys Asn Ile Cys Lys Glu
1090                1095                1100

Cys Pro Ile Ile Gly Phe Arg Tyr Arg Ser Leu Lys His Phe Asn Tyr
1105                1110                1115                1120

Asp Ile Cys Gln Ser Cys Phe Phe Ser Gly Arg Val Ala Lys Gly His
                1125                1130                1135

Lys Met His Tyr Pro Met Val Glu Tyr Cys Thr Pro Thr Thr Ser Gly
                1140                1145                1150

Glu Asp Val Arg Asp Phe Ala Lys Val Leu Lys Asn Lys Phe Arg Thr
            1155                1160                1165

Lys Arg Tyr Phe Ala Lys His Pro Arg Met Gly Tyr Leu Pro Val Gln
        1170                1175                1180

Thr Val Leu Glu Gly Asp Asn Met Glu Thr Pro Val Thr Leu Ile Asn
1185                1190                1195                1200

Phe Trp Pro Val Asp Ser Ala Pro Ala Ser Ser Pro Gln Leu Ser His
                1205                1210                1215

Asp Asp Thr His Ser Arg Ile Glu His Tyr Ala Ser Arg Leu Ala Glu
                1220                1225                1230

Met Glu Asn Ser Asn Gly Ser Tyr Leu Asn Asp Ser Ile Ser Pro Asn
            1235                1240                1245

Glu Ser Ile Asp Asp Glu His Leu Leu Ile Gln His Tyr Cys Gln Ser
            1250                1255                1260

Leu Asn Gln Asp Ser Pro Leu Ser Gln Pro Arg Ser Pro Ala Gln Ile
1265                1270                1275                1280

Leu Ile Ser Leu Glu Ser Glu Glu Arg Gly Glu Leu Glu Arg Ile Leu
                1285                1290                1295

Ala Asp Leu Glu Glu Glu Asn Arg Asn Leu Gln Ala Glu Tyr Asp Arg
                1300                1305                1310

Leu Lys Gln Gln His Glu His Lys Gly Leu Ser Pro Leu Pro Ser Pro
            1315                1320                1325

Pro Glu Met Met Pro Thr Ser Pro Gln Ser Pro Arg Asp Ala Glu Leu
            1330                1335                1340

Ile Ala Glu Ala Lys Leu Leu Arg Gln His Lys Gly Arg Leu Glu Ala
1345                1350                1355                1360
```

Arg Met Gln Ile Leu Glu Asp His Asn Lys Gln Leu Glu Ser Gln Leu
            1365                1370                1375

His Arg Leu Arg Gln Leu Leu Glu Gln Pro Gln Ala Glu Asp Thr Met
        1380                1385                1390

<210> SEQ ID NO 14
<211> LENGTH: 4185
<212> TYPE: DNA
<213> ORGANISM: Artificial Sequence
<220> FEATURE:
<223> OTHER INFORMATION: human MD3 (cDNA)

<400> SEQUENCE: 14

| | | |
|---|---|---|
| atgctgtggt gggaggaagt ggaggactgc tacgagagag aggacgtgca gaagaaaacc | 60 | |
| ttcaccaagt gggtgaacgc ccagttcagc aagttcggca agcagcacat cgagaacctg | 120 | |
| ttcagcgacc tgcaggatgg caggagactg ctggatctgc tggagggact gaccggccag | 180 | |
| aagctgccca aggagaaggg cagcaccaga gtgcacgccc tgaacaacgt gaacaaggcc | 240 | |
| ctgagagtgc tgcagaacaa caacgtggac ctggtgaata tcggcagcac cgacatcgtg | 300 | |
| gacggcaacc acaagctgac cctgggcctg atctggaaca tcatcctgca ctggcaggtg | 360 | |
| aagaacgtga tgaagaacat catggccggc ctgcagcaga ccaacagcga agatcctg | 420 | |
| ctgagctggg tgaggcagag caccagaaac taccccagg tgaacgtgat caacttcacc | 480 | |
| acctcctgga gcgacggcct ggccctgaac gccctgatcc acagccacag acccgacctg | 540 | |
| ttcgactgga acagcgtggt gtgtcagcag agcgccaccc agagactgga gcacgccttc | 600 | |
| aacatcgcca gataccagct gggcatcgag aagctgctgg accccgagga cgtggacacc | 660 | |
| acctaccccg acaagaaaag catcctgatg tatattacct ctctgtttca ggtgctgccc | 720 | |
| cagcaggtgt ccatcgaggc catccaggaa gtggaaatgc tgcccaggcc ccccaaagtg | 780 | |
| accaaggagg agcacttcca gctgcaccac cagatgcact atagccagca gatcaccgtg | 840 | |
| tccctggccc agggctatga gaaaccagc agccccaagc ccagattcaa gagctacgcc | 900 | |
| tacacccagg ccgcctacgt gaccaccct gaccccacca gaagcccctt ccccagccag | 960 | |
| cacctggagg cccccgagga caagagcttc ggcagcagcc tgatggagag cgaagtgaac | 1020 | |
| ctggacagat accagaccgc cctggaggaa gtgctgtctt ggctgctgtc cgccgaggac | 1080 | |
| accctgcagg cccagggcga gatcagcaac gacgtggaag tggtgaagga ccagttccac | 1140 | |
| acccacgagg gctacatgat ggatctgacc gcccaccagg cagagtggg caatatcctg | 1200 | |
| cagctgggca gcaagctgat cggcaccggc aagctgagcg aggacgagga gaccgaagtg | 1260 | |
| caggagcaga tgaacctgct gaacagcaga tgggagtgcc tgagagtggc cagcatggag | 1320 | |
| aagcagagca acctgcaccg cgtgctgatg gacctgcaga accagaagct gaaggagctg | 1380 | |
| aacgactggc tgaccaagac cgaggagcgg accagaaaga tggaggagga gcccctgggc | 1440 | |
| cccgacctgg aggacctgaa gagacaggtg cagcagcaca agtgctgca ggaggacctg | 1500 | |
| gaacaggagc aggtgcgcgt gaacagcctg acccacatgg tggtcgtggt ggacgagagc | 1560 | |
| agcggcgacc acgccacagc cgccctggaa gagcagctga agtgctgggc gacagatgg | 1620 | |
| gccaacatct gccggtggac cgaggacaga tgggtgctgc tgcaggacat cctgctgaag | 1680 | |
| tggcagagac tgacagagga gcagtgcctg tttagcgcct ggctgagcga aggaggac | 1740 | |
| gccgtgaaca gatccacac caccggcttc aaggaccaga cgagatgct gagcagcctg | 1800 | |
| cagaagctgg ccgtgctgaa ggccgatctg gagaagaaaa agcagagcat gggcaagctg | 1860 | |
| tactccctga gcaggacct gctgtccacc ctgaagaaca gagcgtgac ccagaaaacc | 1920 | |

```
gaggcctggc tggacaattt cgcccggtgc tgggacaatc tggtgcagaa actggagaag   1980
agcaccgccc agatcagcca ggccgtgacc accacccagc ccagcctgac acagaccacc   2040
gtgatggaga ccgtgaccac agtgaccacc agggagcaga tcctggtgaa gcacgcccag   2100
gaggagctgc cccctccccc ccctcagaag aagcggcaga tcacagtgga cacccctggag  2160
agactgcagg agctgcagga agccaccgac gagctggacc tgaagctgag acaggccgaa   2220
gtgatcaagg gcagctggca gcctgtgggc gatctgctga tcgacagcct gcaggaccac   2280
ctggagaaag tgaaggccct gcggggcgag atcgcccccc tgaaggagaa tgtgagccac   2340
gtgaacgacc tggccagaca gctgaccacc ctgggcatcc agctgagccc ctacaatctg   2400
agcaccctgg aagatctgaa cacccggtgg aaactgctgc aggtggccgt ggaggataga   2460
gtgaggcagc tgcacgaggc ccacagagac ttcggccctg cctcccagca cttcctgagc   2520
accagcgtgc agggcccctg ggagagagcc atctccccca caaagtgcc ctactacatc    2580
aaccacgaga cccagaccac ctgctgggac caccctaaga tgaccgagct gtaccagagc   2640
ctggccgacc tgaacaatgt gcggttcagc gcctacagaa ccgccatgaa gctgcggaga   2700
ctgcagaagg ccctgtgtcct ggacctgctg agcctgagcg ccgcctgcga cgccctggac  2760
cagcacaacc tgaagcagaa cgaccagccc atggacattc tgcagatcat caactgcctg   2820
accaccatct acgatcggct ggagcaggag cacaacaacc tggtgaacgt gcccctgtgc   2880
gtggacatgt gcctgaattg gctgctgaac gtgtacgaca ccggcaggac cggcagaatc   2940
agagtgctgt ccttcaagac cggcatcatc agcctgtgca aggcccacct ggaggataag   3000
taccgctacc tgttcaagca ggtggccagc agcaccggct tctgcgatca gaggagactg   3060
ggcctgctgc tgcacgatag catccagatc cctaggcagc tgggcgaggt ggccagcttc   3120
ggcggcagca acatcgagcc cagcgtgcgg agctgcttcc agttcgccaa caacaagccc   3180
gagatcgagg ccgccctgtt cctggactgg atgcggctgg aaccccagag catggtctgg   3240
ctgcccgtgc tgcacagagt ggctgccgcc gagaccgcca agcaccaggc caagtgcaac   3300
atctgcaaag agtgccccat catcggcttc cggtacagaa gcctgaagca cttcaactac   3360
gacatctgcc agagctgctt tttcagcggc agagtggcca agggccacaa gatgcactac   3420
cccatggtgg agtactgcac ccccaccacc tccggcgagg acgtgcggga cttcgccaag   3480
gtgctgaaga acaagttccg gaccaagcgg tactttgcca agcaccccg gatgggctac   3540
ctgcccgtgc agaccgtgct ggaaggcgac aacatggaaa ccccgtgac cctgatcaac    3600
ttctggcccg tggacagcgc ccctgccagc agccccagc tgtcccacga cgacacccac    3660
agccggatcg agcactacgc cagccggctc gccgagatgg aaaacagcaa cggcagctac   3720
ctgaacgaca gcatcagccc caacgagagc atcgacgacg agcacctgct gatccagcac   3780
tactgtcaga gcctgaacca ggacagcccc ctgagccagc ccagaagccc tgcccagatc   3840
ctgatcagca tggaaagcga ggaacggggc gagctgaac ggatcctggc cgacctggaa    3900
gaggaaaacc ggaacctgca ggccgagtac gaccggctga agcagcagca cgagcacaag   3960
ggcctgagcc ccctgcccag cccccctgag atgatgccca cctcccccca gagcccagg    4020
gacgccgagc tgatcgccga ggccaagctg ctgcggcagc acaagggcg gctggaagcc    4080
cggatgcaga tcctggaaga tcacaacaag cagctggaaa gccagctgca ccggctgaga   4140
cagctgctgg aacagcccca ggccgaggac accatgtgat gatga                   4185
```

<210> SEQ ID NO 15

<211> LENGTH: 5223
<212> TYPE: DNA
<213> ORGANISM: Artificial Sequence
<220> FEATURE:
<223> OTHER INFORMATION: AAV ITR hMD3

<400> SEQUENCE: 15

```
gcgcgctcgc tcgctcactg aggccgcccg ggcaaagccc gggcgtcggg cgacctttgg      60
tcgcccggcc tcagtgagcg agcgagcgcg cagagaggga gtggccaact ccatcactag     120
gggttccttg tagttaatga ttaacccgcc atgctactta tctacgtagc catgctctag     180
acatggctcg acagatcgag ctccaccgcg gtggcggccg tccgccctcg gcaccatcct     240
cacgacaccc aaatatggcg acgggtgagg aatggtgggg agttattttt agagcggtga     300
ggaaggtggg caggcagcag gtgttggcgc tctaaaaata actcccggga gttattttta     360
gagcggagga atggtggaca cccaaatatg gcgacggttc ctcacccgtc gccatatttg     420
ggtgtccgcc ctcggccggg gccgcattcc tggggccgg gcggtgctcc cgcccgcctc      480
gataaaaggc tccggggccg gcggcggccc acgagctacc ggaggagcg ggaggcgcca      540
agctctagaa ctagtggatc ccccgggctg caggaattcg ccaccatgct gtggtgggag     600
gaagtggagg actgctacga gagagaggac gtgcagaaga aaaccttcac caagtgggtg     660
aacgcccagt tcagcaagtt cggcaagcag cacatcgaga acctgttcag cgacctgcag     720
gatggcagga gactgctgga tctgctggag ggactgaccg ccagaagct gcccaaggag      780
aagggcagca ccagagtgca cgccctgaac aacgtgaaca aggccctgag agtgctgcag     840
aacaacaacg tggacctggt gaatatcggc agcaccgaca tcgtggacgg caaccacaag     900
ctgaccctgg gcctgatctg aacatcatc ctgcactggc aggtgaagaa cgtgatgaag      960
aacatcatgg ccggcctgca gcagaccaac agcgagaaga tcctgctgag ctgggtgagg    1020
cagagcacca gaaactaccc ccaggtgaac gtgatcaact tcaccacctc ctggagcgac    1080
ggcctggccc tgaacgccct gatccacagc cacagacccg acctgttcga ctggaacagc    1140
gtggtgtgtc agcagagcgc cacccagaga ctggagcacg ccttcaacat cgccagatac    1200
cagctgggca tcgagaagct gctggacccc gaggacgtgg acaccaccta ccccgacaag    1260
aaaagcatcc tgatgtatat tacctctctg tttcaggtgc tgccccagca ggtgtccatc    1320
gaggccatcc aggaagtgga aatgctgccc aggccccca aagtgaccaa ggaggagcac     1380
ttccagctgc accaccagat gcactatagc cagcagatca ccgtgtccct ggcccagggc    1440
tatgagagaa ccagcagccc caagcccaga ttcaagagct acgcctacac ccaggccgcc    1500
tacgtgacca cctccgaccc caccagaagc cccttcccca gccagcacct ggaggccccc    1560
gaggacaaga gcttcggcag cagcctgatg gagagcgaag tgaacctgga cagataccag    1620
accgccctgg aggaagtgct gtcttggctg ctgtccgccg gacacccct gcaggcccag    1680
ggcgagatca gcaacgacgt ggaagtggtg aaggaccagt ccacaccca cgagggctac    1740
atgatggatc tgaccgccca ccagggcaga gtgggcaata tcctgcagct gggcagcaag    1800
ctgatcggca ccggcaagct gagcgaggac gaggagaccg aagtgcagga gcagatgaac    1860
ctgctgaaca gcagatggga gtgcctgaga gtggccagca tggagaagca gagcaacctg    1920
caccgcgtgc tgatggacct gcagaaccag aagctgaagg agctgaacga ctggctgacc    1980
aagaccgagg agcggaccag aaagatggag gaggagcccc tgggccccga cctggaggac    2040
ctgaagagac aggtgcagca gcacaaagtg ctgcaggagg acctggaaca ggagcaggtg    2100
cgcgtgaaca gcctgaccca catggtggtc gtggtggacg agagcagcgg cgaccacgcc    2160
```

```
acagccgccc tggaagagca gctgaaagtg ctgggcgaca gatgggccaa catctgccgg    2220
tggaccgagg acagatgggt gctgctgcag gacatcctgc tgaagtggca gagactgaca    2280
gaggagcagt gcctgtttag cgcctggctg agcgagaagg aggacgccgt gaacaagatc    2340
cacaccaccg gcttcaagga ccagaacgag atgctgagca gcctgcagaa gctggccgtg    2400
ctgaaggccg atctggagaa gaaaaagcag agcatgggca agctgtactc cctgaagcag    2460
gacctgctgt ccaccctgaa gaacaagagc gtgacccaga aaaccgaggc ctggctggac    2520
aatttcgccc ggtgctggga caatctggtg cagaaactgg agaagagcac cgcccagatc    2580
agccaggccg tgaccaccac ccagcccagc ctgacacaga ccaccgtgat ggagaccgtg    2640
accacagtga ccaccaggga gcagatcctg gtgaagcacg cccaggagga gctgccccct    2700
cccccccctc agaagaagcg gcagatcaca gtggacaccc tggagagact gcaggagctg    2760
caggaagcca ccgacgagct ggacctgaag ctgagacagg ccgaagtgat caagggcagc    2820
tggcagcctg tgggcgatct gctgatcgac agcctgcagg accacctgga gaaagtgaag    2880
gccctgcggg gcgagatcgc ccccctgaag gagaatgtga gccacgtgaa cgacctggcc    2940
agacagctga ccaccctggg catccagctg agccccctaca atctgagcac cctggaagat    3000
ctgaacaccc ggtggaaact gctgcaggtg gccgtggagg atagagtgag gcagctgcac    3060
gaggcccaca gagacttcgg ccctgcctcc cagcacttcc tgagcaccag cgtgcagggc    3120
ccctgggaga gagccatctc ccccaacaaa gtgccctact acatcaacca cgagacccag    3180
accacctgct gggaccaccc taagatgacc gagctgtacc agagcctggc cgacctgaac    3240
aatgtgcggt tcagcgccta cagaaccgcc atgaagctgc ggagactgca gaaggccctg    3300
tgcctggacc tgctgagcct gagcgccgcc tgcgacgccc tggaccagca caacctgaag    3360
cagaacgacc agcccatgga cattctgcag atcatcaact gcctgaccac catctacgat    3420
cggctggagc aggagcacaa caacctggtg aacgtgcccc tgtgcgtgga catgtgcctg    3480
aattggctgc tgaacgtgta cgacaccggc aggaccggca gaatcagagt gctgtccttc    3540
aagaccggca tcatcagcct gtgcaaggcc cacctggagg ataagtaccg ctacctgttc    3600
aagcaggtgg ccagcagcac cggcttctgc gatcagagga gactgggcct gctgctgcac    3660
gatagcatcc agatccctag gcagctgggc gaggtggcca gcttcggcgg cagcaacatc    3720
gagcccagcg tgcggagctg cttccagttc gccaacaaca gcccgagat cgaggccgcc    3780 ctgttcctgg actggatgcg gctggaaccc cagagcatgg tctggctgcc cgtgctgcac    3840
agagtggctg ccgccgagac cgccaagcac caggccaagt gcaacatctg caaagagtgc    3900
cccatcatcg gcttccggta cagaagcctg aagcacttca actacgacat ctgccagagc    3960 tgcttttca gcgcagagt ggccaagggc cacaagatgc actacccat ggtggagtac    4020 tgcaccccca ccacctccgg cgaggacgtg cgggacttcg ccaaggtgct gaagaacaag    4080
ttccggacca gcggtactt tgccaagcac ccccggatgg gctacctgcc cgtgcagacc    4140
gtgctggaag gcgacaacat ggaaccccc gtgaccctga tcaacttctg gccgtggac    4200 agcgcccctg ccagcagccc ccagctgtcc cacgacgaca cccacagccg gatcgagcac    4260
tacgccagcc ggctcgccga gatggaaaac agcaacggca gctacctgaa cgacagcatc    4320
agccccaacg agagcatcga cgacgagcac ctgctgatcc agcactactg tcagagcctg    4380
aaccaggaca gccccctgag ccagcccaga agccctgccc agatcctgat cagcctggaa    4440
agcgaggaac ggggcgagct ggaacggatc ctggccgacc tggaagagga aaaccggaac    4500
```

-continued

```
ctgcaggccg agtacgaccg gctgaagcag cagcacgagc acaagggcct gagcccctg    4560 cccagcccc ctgagatgat gcccacctcc ccccagagcc caggacgc cgagctgatc      4620 gccgaggcca agctgctgcg gcagcacaag gggcggctgg aagcccggat gcagatcctg  4680
gaagatcaca acaagcagct ggaaagccag ctgcaccggc tgagacagct gctggaacag  4740
ccccaggccg aggacaccat gtgatgatga gcggccgctt cccctttagtg agggttaatg 4800 cttcgagcag acatgataag atacattgat gagtttggac aaaccacaac tagaatgcag  4860
tgaaaaaaat gctttatttg tgaaatttgt gatgctattg ctttatttgt aaccattata  4920
agctgcaata aacaagttaa caacaacaat tgcattcatt ttatgtttca ggttcagggg  4980
gagatgtggg aggtttttta aagcaagtaa aacctctaca aatgtggtaa aatccgataa  5040
ggactagagc atggctacgt agataagtag catggcgggt taatcattaa ctacaaggaa  5100
cccctagtga tggagttggc cactccctct ctgcgcgctc gctcgctcac tgaggccggg  5160
cgaccaaagg tcgcccgacg cccgggcttt gcccgggcgg cctcagtgag cgagcgagcg  5220
cgc                                                                5223
```

<210> SEQ ID NO 16
<211> LENGTH: 1471
<212> TYPE: PRT
<213> ORGANISM: Artificial Sequence
<220> FEATURE:
<223> OTHER INFORMATION: human MD4 (PRT)

<400> SEQUENCE: 16

```
Met Leu Trp Trp Glu Glu Val Glu Asp Cys Tyr Glu Arg Glu Asp Val
1               5                  10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
```

```
            225                 230                 235                 240
Gln Gln Val Ser Ile Glu Ala Ile Gln Glu Val Glu Met Leu Pro Arg
                245                 250                 255
Pro Pro Lys Val Thr Lys Glu Glu His Phe Gln Leu His His Gln Met
                260                 265                 270
His Tyr Ser Gln Gln Ile Thr Val Ser Leu Ala Gln Gly Tyr Glu Arg
                275                 280                 285
Thr Ser Ser Pro Lys Pro Arg Phe Lys Ser Tyr Ala Tyr Thr Gln Ala
                290                 295                 300
Ala Tyr Val Thr Thr Ser Asp Pro Thr Arg Ser Pro Phe Pro Ser Gln
305                 310                 315                 320
His Leu Glu Ala Pro Glu Asp Lys Ser Phe Gly Ser Ser Leu Met Glu
                325                 330                 335
Ser Glu Val Asn Leu Asp Arg Tyr Gln Thr Ala Leu Glu Glu Val Leu
                340                 345                 350
Ser Trp Leu Leu Ser Ala Glu Asp Thr Leu Gln Ala Gln Gly Glu Ile
                355                 360                 365
Ser Asn Asp Val Glu Val Val Lys Asp Gln Phe His Thr His Glu Gly
                370                 375                 380
Tyr Met Met Asp Leu Thr Ala His Gln Gly Arg Val Gly Asn Ile Leu
385                 390                 395                 400
Gln Leu Gly Ser Lys Leu Ile Gly Thr Gly Lys Leu Ser Glu Asp Glu
                405                 410                 415
Glu Thr Glu Val Gln Glu Gln Met Asn Leu Leu Asn Ser Arg Trp Glu
                420                 425                 430
Cys Leu Arg Val Ala Ser Met Glu Lys Gln Ser Asn Leu His Arg Val
                435                 440                 445
Leu Met Asp Leu Gln Asn Gln Lys Leu Lys Glu Leu Asn Asp Trp Leu
                450                 455                 460
Thr Lys Thr Glu Glu Arg Thr Arg Lys Met Glu Glu Pro Leu Gly
465                 470                 475                 480
Pro Asp Leu Glu Asp Leu Lys Arg Gln Val Gln Gln His Lys Val Leu
                485                 490                 495
Gln Glu Asp Leu Glu Gln Glu Gln Val Arg Val Asn Ser Leu Thr His
                500                 505                 510
Met Val Val Val Asp Glu Ser Ser Gly Asp His Ala Thr Ala Ala
                515                 520                 525
Leu Glu Glu Gln Leu Lys Val Leu Gly Asp Arg Trp Ala Asn Ile Cys
                530                 535                 540
Arg Trp Thr Glu Asp Arg Trp Val Leu Leu Gln Asp Ile Leu Leu Lys
545                 550                 555                 560
Trp Gln Arg Leu Thr Glu Glu Gln Cys Leu Phe Ser Ala Trp Leu Ser
                565                 570                 575
Glu Lys Glu Asp Ala Val Asn Lys Ile His Thr Thr Gly Phe Lys Asp
                580                 585                 590
Gln Asn Glu Met Leu Ser Ser Leu Gln Lys Leu Ala Val Leu Lys Ala
                595                 600                 605
Asp Leu Glu Lys Lys Lys Gln Ser Met Gly Lys Leu Tyr Ser Leu Lys
                610                 615                 620
Gln Asp Leu Leu Ser Thr Leu Lys Asn Lys Ser Val Thr Gln Lys Thr
625                 630                 635                 640
Glu Ala Trp Leu Asp Asn Phe Ala Arg Cys Trp Asp Asn Leu Val Gln
                645                 650                 655
```

-continued

Lys Leu Glu Lys Ser Thr Ala Gln Ile Ser Gln Ala Val Thr Thr Thr
                660                 665                 670

Gln Pro Ser Leu Thr Gln Thr Thr Val Met Glu Thr Val Thr Thr Val
            675                 680                 685

Thr Thr Arg Glu Gln Ile Leu Val Lys His Ala Gln Glu Leu Pro
        690                 695                 700

Pro Pro Pro Pro Gln Lys Lys Arg Gln Ile Thr Val Asp Thr Leu Glu
705                 710                 715                 720

Arg Leu Gln Glu Leu Gln Glu Ala Thr Asp Glu Leu Asp Leu Lys Leu
                725                 730                 735

Arg Gln Ala Glu Val Ile Lys Gly Ser Trp Gln Pro Val Gly Asp Leu
            740                 745                 750

Leu Ile Asp Ser Leu Gln Asp His Leu Glu Lys Val Lys Ala Leu Arg
        755                 760                 765

Gly Glu Ile Ala Pro Leu Lys Glu Asn Val Ser His Val Asn Asp Leu
    770                 775                 780

Ala Arg Gln Leu Thr Thr Leu Gly Ile Gln Leu Ser Pro Tyr Asn Leu
785                 790                 795                 800

Ser Thr Leu Glu Asp Leu Asn Thr Arg Trp Lys Leu Leu Gln Val Ala
                805                 810                 815

Val Glu Asp Arg Val Arg Gln Leu His Glu Ala His Arg Asp Phe Gly
            820                 825                 830

Pro Ala Ser Gln His Phe Leu Ser Thr Ser Val Gln Gly Pro Trp Glu
        835                 840                 845

Arg Ala Ile Ser Pro Asn Lys Val Pro Tyr Tyr Ile Asn His Glu Thr
    850                 855                 860

Gln Thr Thr Cys Trp Asp His Pro Lys Met Thr Glu Leu Tyr Gln Ser
865                 870                 875                 880

Leu Ala Asp Leu Asn Asn Val Arg Phe Ser Ala Tyr Arg Thr Ala Met
                885                 890                 895

Lys Leu Arg Arg Leu Gln Lys Ala Leu Cys Leu Asp Leu Leu Ser Leu
            900                 905                 910

Ser Ala Ala Cys Asp Ala Leu Asp Gln His Asn Leu Lys Gln Asn Asp
        915                 920                 925

Gln Pro Met Asp Ile Leu Gln Ile Ile Asn Cys Leu Thr Thr Ile Tyr
    930                 935                 940

Asp Arg Leu Glu Gln Glu His Asn Asn Leu Val Asn Val Pro Leu Cys
945                 950                 955                 960

Val Asp Met Cys Leu Asn Trp Leu Leu Asn Val Tyr Asp Thr Gly Arg
                965                 970                 975

Thr Gly Arg Ile Arg Val Leu Ser Phe Lys Thr Gly Ile Ile Ser Leu
            980                 985                 990

Cys Lys Ala His Leu Glu Asp Lys Tyr Arg Tyr Leu Phe Lys Gln Val
        995                 1000                1005

Ala Ser Ser Thr Gly Phe Cys Asp Gln Arg Arg Leu Gly Leu Leu Leu
    1010                1015                1020

His Asp Ser Ile Gln Ile Pro Arg Gln Leu Gly Glu Val Ala Ser Phe
1025                1030                1035                1040

Gly Gly Ser Asn Ile Glu Pro Ser Val Arg Ser Cys Phe Gln Phe Ala
                1045                1050                1055

Asn Asn Lys Pro Glu Ile Glu Ala Ala Leu Phe Leu Asp Trp Met Arg
            1060                1065                1070

Leu Glu Pro Gln Ser Met Val Trp Leu Pro Val Leu His Arg Val Ala
        1075                1080                1085

Ala Ala Glu Thr Ala Lys His Gln Ala Lys Cys Asn Ile Cys Lys Glu
    1090                1095                1100

Cys Pro Ile Ile Gly Phe Arg Tyr Arg Ser Leu Lys His Phe Asn Tyr
1105                1110                1115                1120

Asp Ile Cys Gln Ser Cys Phe Phe Ser Gly Arg Val Ala Lys Gly His
                1125                1130                1135

Lys Met His Tyr Pro Met Val Glu Tyr Cys Thr Pro Thr Thr Ser Gly
        1140                1145                1150

Glu Asp Val Arg Asp Phe Ala Lys Val Leu Lys Asn Lys Phe Arg Thr
    1155                1160                1165

Lys Arg Tyr Phe Ala Lys His Pro Arg Met Gly Tyr Leu Pro Val Gln
1170                1175                1180

Thr Val Leu Glu Gly Asp Asn Met Glu Thr Pro Val Thr Leu Ile Asn
1185                1190                1195                1200

Phe Trp Pro Val Asp Ser Ala Pro Ala Ser Ser Pro Gln Leu Ser His
                1205                1210                1215

Asp Asp Thr His Ser Arg Ile Glu His Tyr Ala Ser Arg Leu Ala Glu
        1220                1225                1230

Met Glu Asn Ser Asn Gly Ser Tyr Leu Asn Asp Ser Ile Ser Pro Asn
    1235                1240                1245

Glu Ser Ile Asp Asp Glu His Leu Leu Ile Gln His Tyr Cys Gln Ser
1250                1255                1260

Leu Asn Gln Asp Ser Pro Leu Ser Gln Pro Arg Ser Pro Ala Gln Ile
1265                1270                1275                1280

Leu Ile Ser Leu Glu Ser Glu Glu Arg Gly Glu Leu Glu Arg Ile Leu
                1285                1290                1295

Ala Asp Leu Glu Glu Glu Asn Arg Asn Leu Gln Ala Glu Tyr Asp Arg
        1300                1305                1310

Leu Lys Gln Gln His Glu His Lys Gly Leu Ser Pro Leu Pro Ser Pro
    1315                1320                1325

Pro Glu Met Met Pro Thr Ser Pro Gln Ser Pro Arg Asp Ala Glu Leu
1330                1335                1340

Ile Ala Glu Ala Lys Leu Leu Arg Gln His Lys Gly Arg Leu Glu Ala
1345                1350                1355                1360

Arg Met Gln Ile Leu Glu Asp His Asn Lys Gln Leu Glu Ser Gln Leu
                1365                1370                1375

His Arg Leu Arg Gln Leu Leu Glu Gln Pro Gln Ala Glu Ala Lys Val
        1380                1385                1390

Asn Gly Thr Thr Val Ser Ser Pro Ser Thr Ser Leu Gln Arg Ser Asp
    1395                1400                1405

Ser Ser Gln Pro Met Leu Leu Arg Val Val Gly Ser Gln Thr Ser Asp
1410                1415                1420

Ser Met Gly Glu Glu Asp Leu Leu Ser Pro Pro Gln Asp Thr Ser Thr
1425                1430                1435                1440

Gly Leu Glu Glu Val Met Glu Gln Leu Asn Asn Ser Phe Pro Ser Ser
                1445                1450                1455

Arg Gly Arg Asn Thr Pro Gly Lys Pro Met Arg Glu Asp Thr Met
        1460                1465                1470

<210> SEQ ID NO 17
<211> LENGTH: 4422
<212> TYPE: DNA

<213> ORGANISM: Artificial Sequence
<220> FEATURE:
<223> OTHER INFORMATION: human MD4 (cDNA)

<400> SEQUENCE: 17

| | | | | | |
|---|---|---|---|---|---|
| atgctgtggt | gggaggaagt | ggaggactgc | tacgagagag | aggacgtgca | gaagaaaacc | 60 |
| ttcaccaagt | gggtgaacgc | ccagttcagc | aagttcggca | agcagcacat | cgagaacctg | 120 |
| ttcagcgacc | tgcaggatgg | caggagactg | ctggatctgc | tggagggact | gaccggccag | 180 |
| aagctgccca | aggagaaggg | cagcaccaga | gtgcacgccc | tgaacaacgt | gaacaaggcc | 240 |
| ctgagagtgc | tgcagaacaa | caacgtggac | ctggtgaata | tcggcagcac | cgacatcgtg | 300 |
| gacggcaacc | acaagctgac | cctgggcctg | atctggaaca | tcatcctgca | ctggcaggtg | 360 |
| aagaacgtga | tgaagaacat | catggccggc | ctgcagcaga | ccaacagcga | aagatcctg | 420 |
| ctgagctggg | tgaggcagag | caccagaaac | tacccccagg | tgaacgtgat | caacttcacc | 480 |
| acctcctgga | gcgacggcct | ggccctgaac | gccctgatcc | acagccacag | acccgacctg | 540 |
| ttcgactgga | acagcgtggt | gtgtcagcag | agcgccaccc | agagactgga | gcacgccttc | 600 |
| aacatcgcca | gataccagct | gggcatcgag | aagctgctgg | accccgagga | cgtggacacc | 660 |
| acctaccccg | acaagaaaag | catcctgatg | tatattacct | ctctgtttca | ggtgctgccc | 720 |
| cagcaggtgt | ccatcgaggc | catccaggaa | gtggaaatgc | tgcccaggcc | ccccaaagtg | 780 |
| accaaggagg | agcacttcca | gctgcaccac | cagatgcact | atagccagca | gatcaccgtg | 840 |
| tccctggccc | agggctatga | gagaaccagc | agccccaagc | ccagattcaa | gagctacgcc | 900 |
| tacacccagg | ccgcctacgt | gaccacctcc | gaccccacca | gaagcccctt | ccccagccag | 960 |
| cacctggagg | cccccgagga | caagagcttc | ggcagcagcc | tgatggagag | cgaagtgaac | 1020 |
| ctggacagat | accagaccgc | cctggaggaa | gtgctgtctt | ggctgctgtc | cgccgaggac | 1080 |
| accctgcagg | cccagggcga | gatcagcaac | gacgtggaag | tggtgaagga | ccagttccac | 1140 |
| acccacgagg | gctacatgat | ggatctgacc | gccaccagg | gcagagtggg | caatatcctg | 1200 |
| cagctgggca | gcaagctgat | cggcaccggc | aagctgagcg | aggacgagga | gaccgaagtg | 1260 |
| caggagcaga | tgaacctgct | gaacagcaga | tgggagtgcc | tgagagtggc | cagcatggag | 1320 |
| aagcagagca | acctgcaccg | cgtgctgatg | gacctgcaga | accagaagct | gaaggagctg | 1380 |
| aacgactggc | tgaccaagac | cgaggagcgg | accagaaaga | tggaggagga | gcccctgggc | 1440 |
| cccgacctgg | aggacctgaa | gagacaggtg | cagcagcaca | aagtgctgca | ggaggacctg | 1500 |
| gaacaggagc | aggtgcgcgt | gaacagcctg | acccacatgg | tggtcgtggt | ggacgagagc | 1560 |
| agcggcgacc | acgccacagc | cgccctggaa | gagcagctga | agtgctggg | cgacagatgg | 1620 |
| gccaacatct | gccggtggac | cgaggacaga | tgggtgctgc | tgcaggacat | cctgctgaag | 1680 |
| tggcagagac | tgacagagga | gcagtgcctg | tttagcgcct | ggctgagcga | aaggaggac | 1740 |
| gccgtgaaca | agatccacac | caccggcttc | aaggaccaga | cgagatgct | gagcagcctg | 1800 |
| cagaagctgg | ccgtgctgaa | ggccgatctg | agaagaaaa | agcagagcat | gggcaagctg | 1860 |
| tactccctga | gcaggacct | gctgtccacc | ctgaagaaca | agagcgtgac | ccagaaaacc | 1920 |
| gaggcctggc | tggacaattt | cgcccggtgc | tgggacaatc | tggtgcagaa | actggagaag | 1980 |
| agcaccgccc | agatcagcca | ggccgtgacc | accacccagc | ccagcctgac | acagaccacc | 2040 |
| gtgatggaga | ccgtgaccac | agtgaccacc | agggagcaga | tcctggtgaa | gcacgcccag | 2100 |
| gaggagctgc | cccctccccc | ccctcagaag | aagcggcaga | tcacagtgga | caccctggag | 2160 |
| agactgcagg | agctgcagga | agccaccgac | gagctggacc | tgaagctgag | acaggccgaa | 2220 |

```
gtgatcaagg gcagctggca gcctgtgggc gatctgctga tcgacagcct gcaggaccac    2280
ctggagaaag tgaaggccct gcggggcgag atcgccccc  tgaaggagaa tgtgagccac    2340
gtgaacgacc tggccagaca gctgaccacc ctgggcatcc agctgagccc ctacaatctg    2400
agcaccctgg aagatctgaa cacccggtgg aaactgctgc aggtggccgt ggaggataga    2460
gtgaggcagc tgcacgaggc ccacagagac ttcggccctg cctcccagca cttcctgagc    2520
accagcgtga agggcccctg ggagagagcc atctccccca caaagtgcc  ctactacatc    2580 aaccacgaga cccagaccac ctgctgggac cacctaaga  tgaccgagct gtaccagagc    2640
ctggccgacc tgaacaatgt gcggttcagc gcctacagaa ccgccatgaa gctgcggaga    2700
ctgcagaagg ccctgtgcct ggacctgctg agcctgagcg ccgcctgcga cgccctggac    2760
cagcacaacc tgaagcagaa cgaccagccc atggacattc tgcagatcat caactgcctg    2820
accaccatct acgatcggct ggagcaggag cacaacaacc tggtgaacgt gcccctgtgc    2880
gtggacatgt gcctgaattg ctgctgaac  gtgtacgaca ccggcaggac cggcagaatc    2940
agagtgctgt ccttcaagac cggcatcatc agcctgtgca aggcccacct ggaggataag    3000
taccgctacc tgttcaagca ggtggccagc agcaccggct tctgcgatca ggagagactg    3060
ggcctgctgc tgcacgatag catccagatc cctaggcagc tgggcgaggt ggccagcttc    3120
ggcggcagca acatcgagcc cagcgtgcgg agctgcttcc agttcgccaa caacaagccc    3180
gagatcgagg ccgccctgtt cctggactgg atgcggctgg aaccccagag catggtctgg    3240
ctgcccgtgc tgcacagagt ggctgccgcc gagaccgcca agcaccaggc caagtgcaac    3300
atctgcaaag agtgccccat catcggcttc cggtacagaa gcctgaagca cttcaactac    3360
gacatctgcc agagctgctt tttcagcggc agagtggcca agggcacaa  gatgcactac    3420 cccatggtgg agtactgcac ccccaccacc tccggcgagg acgtgcggga cttcgccaag    3480
gtgctgaaga caagttccg  gaccaagcgg tactttgcca agcaccccg  gatgggctac    3540 ctgcccgtgc agaccgtgct ggaaggcgac aacatggaaa ccccccgtgac cctgatcaac    3600 ttctggcccg tggacagcgc ccctgccagc agcccccagc tgtcccacga cgacacccac    3660
agccggatcg agcactacgc cagccggctc gccgagatgg aaaacagcaa cggcagctac    3720
ctgaacgaca gcatcagccc caacgagagc atcgacgacg agcacctgct gatccagcac    3780
tactgtcaga gcctgaacca ggacagcccc ctgagccagc ccagaagccc tgcccagatc    3840
ctgatcagcc tggaaagcga ggaacggggc gagctggaac ggatcctggc cgacctggaa    3900 gaggaaaaacc ggaacctgca ggccgagtac accggctga  agcagcagca cgagcacaag    3960
ggcctgagcc ccctgcccag cccccctgag atgatgccca cctcccccca gagccccagg    4020
gacgccgagc tgatcgccga ggccaagctg ctgcggcagc acaaggggcg gctggaagcc    4080
cggatgcaga tcctggaaga tcacaacaag cagctggaaa gccagctgca ccggctgaga    4140
cagctgctgg aacagcccca ggccgaagcc aaggtgaacg gcaccaccgt gagcagcccc    4200
agcaccagcc tgcagcggag cgacagctct cagccaatgc tcctgcgggt ggtgggctct    4260
cagaccagcg acagcatggg cgaagaggac ctgctgtccc cacctcaaga caccagcacc    4320
ggcctggaag aagtgatgga acagctgaac aacagcttcc ccagcagccg gggcagaaac    4380
acccccggca agcccatgcg ggaggacacc atgtgatgat ga                       4422

<210> SEQ ID NO 18
<211> LENGTH: 5460
<212> TYPE: DNA
```

<213> ORGANISM: Artificial Sequence
<220> FEATURE:
<223> OTHER INFORMATION: AAV ITR hMD4

<400> SEQUENCE: 18

```
gcgcgctcgc tcgctcactg aggccgcccg ggcaaagccc gggcgtcggg cgacctttgg      60
tcgcccggcc tcagtgagcg agcgagcgcg cagagaggga gtggccaact ccatcactag     120
gggttccttg tagttaatga ttaacccgcc atgctactta tctacgtagc catgctctag     180
acatggctcg acagatcgag ctccaccgcg gtggcggccg tccgccctcg gcaccatcct     240
cacgacaccc aaatatgcg acgggtgagg aatggtgggg agttattttt agagcggtga     300
ggaaggtggg caggcagcag gtgttggcgc tctaaaaata actcccggga gttattttta     360
gagcggagga atggtggaca cccaaatatg gcgacggttc ctcacccgtc gccatatttg     420
ggtgtccgcc ctcggccggg gccgcattcc tgggggccgg gcggtgctcc cgcccgcctc     480
gataaaaggc tccggggccg gcggcggcc acgagctacc cggaggagcg ggaggcgcca     540
agctctagaa ctagtggatc ccccgggctg caggaattcg ccaccatgct gtggtgggag     600
gaagtggagg actgctacga gagagaggac gtgcagaaga aaaccttcac caagtgggtg     660
aacgcccagt tcagcaagtt cggcaagcag cacatcgaga acctgttcag cgacctgcag     720
gatggcagga gactgctgga tctgctggag ggactgaccg ccagaagct gcccaaggag     780
aagggcagca ccagagtgca cgccctgaac aacgtgaaca aggccctgag agtgctgcag     840
aacaacaacg tggacctggt gaatatcggc agcaccgaca tcgtggacgg caaccacaag     900
ctgacctgg gcctgatctg gaacatcatc ctgcactggc aggtgaagaa cgtgatgaag     960
aacatcatgg ccggcctgca gcagaccaac agcgagaaga tcctgctgag ctgggtgagg    1020
cagagcacca gaaactaccc ccaggtgaac gtgatcaact tcaccacctc ctggagcgac    1080
ggcctggccc tgaacgccct gatccacagc cacagacccg acctgttcga ctggaacagc    1140
gtggtgtgtc agcagagcgc cacccagaga ctggagcacg ccttcaacat cgccagatac    1200
cagctgggca tcgagaagct gctggacccc gaggacgtgg acaccaccta ccccgacaag    1260
aaaagcatcc tgatgtatat tacctctctg tttcaggtgc tgcccagca ggtgtccatc    1320
gaggccatcc aggaagtgga aatgctgccc aggccccca aagtgaccaa ggaggagcac    1380
ttccagctgc accaccagat gcactatagc cagcagatca ccgtgtccct ggcccagggc    1440
tatgagagaa ccagcagccc caagcccaga ttcaagagct acgcctacac ccaggccgcc    1500
tacgtgacca cctccgaccc caccagaagc cccttcccca gccagcacct ggaggccccc    1560
gaggacaaga gcttcggcag cagcctgatg gagagcgaag tgaacctgga cagataccag    1620
accgccctgg aggaagtgct gtcttggctg ctgtccgccg gagaccccct gcaggccag    1680
ggcgagatca gcaacgacgt ggaagtggtg aaggaccagt ccacaccca cgagggctac    1740
atgatggatc tgaccgccca ccagggcaga gtgggcaata tcctgcagct gggcagcaag    1800
ctgatcggca ccgcaagct gagcgaggac gaggagaccc aagtgcagga gcagatgaac    1860
ctgctgaaca gcagatggga gtgcctgaga gtggccagca tggagaagca gagcaacctg    1920
caccgcgtgc tgatggacct gcagaaccag aagctgaagg agctgaacga ctggctgacc    1980
aagaccgagg agcggaccag aaagatggag gaggagcccc tgggccccga cctggaggac    2040
ctgaagagac aggtgcagca gcacaaagtg ctgcaggagg acctggaaca ggagcaggtg    2100
cgcgtgaaca gcctgaccca catggtggtc gtggtggacg agagcagcgg cgaccacgcc    2160
acagccgccc tggaagagca gctgaaagtg ctgggcgaca gatgggccaa catctgccgg    2220
```

```
tggaccgagg acagatgggt gctgctgcag acatcctgc tgaagtggca gagactgaca    2280
gaggagcagt gcctgtttag cgcctggctg agcgagaagg aggacgccgt gaacaagatc    2340
cacaccaccg gcttcaagga ccagaacgag atgctgagca gcctgcagaa gctggccgtg    2400
ctgaaggccg atctggagaa gaaaaagcag agcatgggca gctgtactc cctgaagcag    2460 gacctgctgt ccaccctgaa gaacaagagc gtgacccaga aaccgaggc ctggctggac    2520 aatttcgccc ggtgctggga caatctggtg cagaaactgg agaagagcac cgcccagatc    2580
agccaggccg tgaccaccac ccagcccagc ctgacacaga ccaccgtgat ggagaccgtg    2640
accacagtga ccaccaggga gcagatcctg gtgaagcacg cccaggagga gctgcccct    2700 cccccctc agaagaagcg gcagatcaca gtggacaccc tggagagact gcaggagctg    2760
caggaagcca ccgacgagct ggacctgaag ctgagacagg ccgaagtgat caagggcagc    2820
tggcagcctg tgggcgatct gctgatcgac agcctgcagg accacctgga gaaagtgaag    2880
gccctgcggg gcgagatcgc cccctgaag gagaatgtga ccacgtgaa cgacctggcc    2940 agacagctga ccaccctggg catccagctg agccctaca atctgagcac cctggaagat    3000
ctgaacaccc ggtggaaact gctgcaggtg ccgtggagg atagagtgag gcagctgcac    3060
gaggcccaca gagacttcgg ccctgcctcc cagcacttcc tgagcaccag cgtgcagggc    3120
ccctgggaga gagccatctc ccccaacaaa gtgccctact acatcaacca cgagacccag    3180
accacctgct gggaccaccc taagatgacc gagctgtacc agagcctggc cgacctgaac    3240
aatgtgcggt tcagcgccta cagaaccgcc atgaagctgc ggagactgca gaaggccctg    3300
tgcctggacc tgctgagcct gagcgccgcc tgcgacgccc tggaccagca aacctgaag    3360 cagaacgacc agcccatgga cattctgcag atcatcaact gcctgaccac catctacgat    3420
cggctggagc aggagcacaa caacctggtg aacgtgcccc tgtgcgtgga catgtgcctg    3480
aattggctgc tgaacgtgta cgacaccggc aggaccggca gaatcagagt gctgtccttc    3540
aagaccggca tcatcagcct gtgcaaggcc cacctggagg ataagtaccg ctacctgttc    3600
aagcaggtgg ccagcagcac cggcttctgc gatcagagga gactgggcct gctgctgcac    3660
gatagcatcc agatccctag gcagctgggc gaggtggcca gcttcggcgg cagcaacatc    3720
gagcccagcg tgcggagctg cttccagttc gccaacaaca gcccgagat cgaggccgcc    3780 ctgttcctgg actggatgcg gctggaaccc cagagcatgg tctggctgcc cgtgctgcac    3840
agagtggctg ccgccgagac cgccaagcac caggccaagt gcaacatctg caaagagtgc    3900
cccatcatcg gcttccggta cagaagcctg aagcacttca actacgacat ctgccagagc    3960 tgcttttca gcggcagagt ggccaagggc cacaagatgc actacccat ggtggagtac    4020 tgcaccccca ccacctccgg cgaggacgtg cgggacttcg ccaaggtgct gaagaacaag    4080
ttccggacca gcggtactt tgccaagcac ccccggatgg gctacctgcc cgtgcagacc    4140
gtgctggaag cgacaacat ggaaccccc gtgaccctga tcaacttctg gcccgtggac    4200
agcgcccctg ccagcagccc ccagctgtcc cacgacgaca cccacagccg gatcgagcac    4260
tacgccagcc ggctcgccga gatggaaaac agcaacggca gctacctgaa cgacagcatc    4320
agccccaacg agagcatcga cgacgagcac ctgctgatcc agcactactg tcagagcctg    4380
aaccaggaca gccccctgag ccagcccaga agccctgccc agatcctgat cagcctggaa    4440
agcgaggaac ggggcgagct ggaacggatc ctggccgacc tggaagagga aaccggaac    4500 ctgcaggccg agtacgaccg gctgaagcag cagcacgagc acaagggcct gagccccctg    4560
```

```
cccagccccc ctgagatgat gcccacctcc ccccagagcc ccagggacgc cgagctgatc    4620
gccgaggcca agctgctgcg gcagcacaag gggcggctgg aagcccggat gcagatcctg    4680
gaagatcaca acaagcagct ggaaagccag ctgcaccggc tgagacagct gctggaacag    4740
ccccaggccg aagccaaggt gaacggcacc accgtgagca gccccagcac cagcctgcag    4800
cggagcgaca gctctcagcc aatgctcctg cgggtggtgg gctctcagac cagcgacagc    4860
atgggcgaag aggacctgct gtccccacct caagacacca gcaccggcct ggaagaagtg    4920
atggaacagc tgaacaacag cttccccagc agccggggca gaaacacccc cggcaagccc    4980
atgcgggagc acaccatgtg atgatgagcg gccgcttccc tttagtgagg gttaatgctt    5040
cgagcagaca tgataagata cattgatgag tttggacaaa ccacaactag aatgcagtga    5100
aaaaaatgct ttatttgtga aatttgtgat gctattgctt tatttgtaac cattataagc    5160
tgcaataaac aagttaacaa caacaattgc attcatttta tgtttcaggt tcagggggag    5220
atgtgggagg tttttttaaag caagtaaaac ctctacaaat gtggtaaaat ccgataagga    5280
ctagagcatg gctacgtaga taagtagcat ggcgggttaa tcattaacta caaggaaccc    5340
ctagtgatgg agttggccac tccctctctg cgcgctcgct cgctcactga ggccgggcga    5400
ccaaaggtcg cccgacgccc gggctttgcc cgggcggcct cagtgagcga gcgagcgcgc    5460
```

PRODUCTION OF LARGE-SIZED MICRODYSTROPHINS IN AN AAV-BASED VECTOR CONFIGURATION

CROSS REFERENCE TO RELATED APPLICATION

This is a § 371 U.S. national stage of International Application No. PCT/EP2016/060350, filed May 9, 2016, which was published in English under PCT Article 21(2), which claims the benefit of Great Britain Application No. 1507842.1, filed on May 7, 2015.

The present invention relates to gene therapy vectors which are useful in the treatment or prevention of dystrophic diseases, especially Duchenne muscular dystrophy (DMD) or Becker muscular dystrophy (BMD).

The present application reports that packaging of an oversized DNA sequence encoding a microdystrophin does not affect the production of the AAV serotype 8 or 9. This allows the production of large microdystrophins encompassing further active domains, e.g. rod (R) and CT domains.

BACKGROUND OF THE INVENTION

Duchenne muscular dystrophy (DMD) is the most frequent progressive muscle degenerative disease, affecting approximately one in 3,500 to 5000 male births. DMD is caused by deletions or mutations in the gene encoding dystrophin, located on the X chromosome. Dystrophin is required for the assembly of the dystrophin-glycoprotein complex, and provides a mechanical and functional link between the cytoskeleton of the muscle fiber and the extracellular matrix. The absence of functional dystrophin causes fiber degeneration, inflammation, necrosis and replacement of muscle with scar and fat tissue, resulting in progressive muscle weakness and premature death due to respiratory and cardiac failure between the second and fourth decade of life (Moser, H., Hum Genet, 1984. 66(1): 17-40).

A milder form of the disease called Becker muscular dystrophy (BMD) is distinguished from DMD by delayed onset, later dependence on wheelchair support, and longer life span. BMD is caused by mutations maintaining the reading frame and the most critical parts of the gene, leading to a truncated but still functional dystrophin protein (Muntoni F et al, Lancet Neurol, 2003. 2(12): 731-40).

There is no cure nor effective treatment available for DMD (Rodino-Klapac, L. R. et al., Curr Neurol Neurosci Rep, 2013. 13(3): 332) or BMD. Conventional therapies are limited to supportive care, which partially alleviates signs and symptoms, but does not directly target the disease mechanism nor reverse the phenotype.

There currently are several therapeutic strategies being developed for DMD including in vivo gene therapy, cell transplantation therapy, pharmacologic rescue of DMD nonsense mutations and exon skipping strategies to repair the dystrophin gene reading frame. All of these strategies have problems to overcome, including targeting different muscle groups, optimization of delivery, long-term expression of the transgene, and potential immune response (Jarmin et al., Expert Opin Biol Ther, 2014. 14(2): 209-30).

Different gene transfer approaches for DMD aim to compensate for dystrophin loss-of-function and offer the potential to treat all patients using a single medication. In order to prevent muscle degeneration, around 30% of normal levels of dystrophin proteins are likely to be required.

The dystrophin gene is the largest known gene in the human genome, spanning over 2.5 Mb or some 2% of the entire X chromosome in humans. It consists of 79 exons gene locus (full length cDNA: 11.1 kb), which encodes for a 3685 amino acids, 427 kD dystrophin protein. Dystrophin protein is defined by four structural regions (FIG. 1). These are the actin binding domain at the $NH_2$ terminus (exons 1 to 8), central rod domain (24 spectrin-like repeats R1-24 and 4 Hinge regions H1-4; exons 9 to 62), cysteine-rich (CR) domain (exons 63 to 69), and carboxy-terminal (CT) domain (exons 70 to 79).

This size is too large to fit inside known gene therapy vector systems, especially in Adeno-Associated Virus (AAV) vector which is one of the promising candidates with efficient gene transfer into various muscle groups depending on tropism of AAV serotypes. AAV vector has a potential to show long term gene transduction in both dividing (myofibres and cardiomyocytes) and non-dividing (mature myotubes) muscle cells.

Indeed, a major limitation of AAV is its cargo capacity which is thought to be limited to around 5 kb, the size of parental viral genome (Wu Z. et al., Mol Ther., 2010, 18(1): 80-86; Lai Y. et al., Mol Ther., 2010, 18(1): 75-79; Wang Y. et al., Hum Gene Ther Methods, 2012, 23(4): 225-33). Larger vector genomes resulted in truncated packaged genomes, heterogeneous population of genome with broad size distribution, and lower expression efficiency (Wu Z. et al., Mol Ther., 2010, 18(1): 80-86). The use of proteasome inhibitors has been suggested to improve the transduction profile of AAV encapsidating genomes larger than wild-type size (Grieger and Samulski, J. Virol. 2005, 79(15): 9933-44).

However, packaging of a 5.4 kb DNA sequence has been reported for a cardiac sarcomeric protein produced with AAV6 or AAV9 vectors in cardiac tissue (Mearini et al., Nature Communications, 2014. 5:5515).

To overcome the DNA packaging limitation of AAV (<5 kb), several research groups have attempted to engineer synthetic microdystrophins (MD, also known as "minidystrophin"), i.e. truncated but functional proteins. A series of microdystrophins have been designed to encode truncated dystrophins, optimized to contain the more clinically important regions of the protein. Such regions have generally been thought to lie within dystrophin's N-terminal and cysteine-rich domains.

Microdystrophin, which contains the first 3 and the last of the 24 spectrin-like repeats without the C-terminal domain (ΔR4-R23/ΔCT), named MD1, displayed highly functional activity to restore dystrophin and co-localise with syntrophin and dystrobrevin, but it failed to recruit nNOS at the sarcolemma in mdx mouse model (Yue, et al., Mol Ther, 2006. 14(1): 79-87).

Recent trials with AAV2/8 vector encoding a sequence optimized canine MD1 micro-dystrophin, with expression driven by a muscle-specific spc512 promoter (AAV8-spc512-cMD1) in the dystrophic CXMDj dog (Koo et al., J Gene Med, 2011. 13(9): 497-506) have proved encouraging. Isolated limb perfusion studies in 3-month-old animals using modest single administration vector doses ($5 \times 10^{12}$/kg) demonstrate up to 95% Dystrophin positive fibres in the treated limbs at the 6-week post-treatment and significant normalisation of clinical scores in treated canine subjects.

However, the relevance of the deleted regions, especially of the CT domains of dystrophin, in muscle function remains controversial.

Therefore, there is a need in the art for developing partially deleted but highly functional dystrophin genes, which can be successfully packaged inside AAV vectors.

BRIEF SUMMARY OF THE INVENTION

The present invention aims at alleviating or curing the devastating Duchenne muscular dystrophy (DMD) as well as Becker muscular dystrophy (BMD) by expressing a shorter but functional dystrophin polypeptide called microdystrophin.

The present invention reports the unexpected finding to package in AAV vectors sequences of more than 5 kb (above the acknowledged limitation) encoding larger active microdystrophins. This offers new therapeutic tools, i.e. newly engineered microdystrophins encapsidated in AAV capsids for treating dystrophic diseases.

While the success of said approach, i.e. packaging of an oversized DNA sequence, can depend on the nature of the DNA sequence as well as on the target tissue, the present application is the first report in relation with the production of large and active microdystrophins in the muscles tissue.

SEQUENCE LISTING

The Sequence Listing is submitted as an ASCII text file 8050-99873-01_Sequence_Listing.txt, Oct. 24, 2019, 148 KB], which is incorporated by reference herein.

DETAILED DESCRIPTION OF SEVERAL EMBODIMENTS

Definitions

The articles "a" and "an" are used herein to refer to one or to more than one (i.e., to at least one) of the grammatical object of the article. By way of example, "an element" means one element or more than one element.

"About" or "approximately" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or a RNA or a cDNA may also include introns to the extent that the nucleotide sequence encoding the protein may in some version contain an intron(s).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

"Identical" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous or identical at that position. The percent of homology/identity between two sequences is a function of the number of matching positions shared by the two sequences divided by the number of positions compared X 100. For example, if 6 of 10 of the positions in two sequences are matched then the two sequences are 60% identical. Generally, a comparison is made when two sequences are aligned to give maximum homology/identity.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell preferentially if the cell is a cell of the tissue type corresponding to the promoter.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" or "ameliorated" if the severity of a symptom of the disease or disorder, the frequency with which such a symptom is experienced by a patient, or both, is reduced. This also includes halting progression of the disease or disorder. A disease or disorder is "cured" if the severity of a symptom of the disease or disorder, the frequency with which such a symptom is experienced by a patient, or both, is eliminated.

A "therapeutic" treatment is a treatment administered to a subject who exhibits signs of pathology, for the purpose of diminishing or eliminating those signs.

As used herein, "treating a disease or disorder" means reducing the frequency or severity of at least one sign or symptom of a disease or disorder experienced by a subject. Disease and disorder are used interchangeably herein in the context of treatment.

An "effective amount" of a compound is that amount of compound which is sufficient to provide a beneficial effect to the subject to which the compound is administered. The phrase "therapeutically effective amount", as used herein, refers to an amount that is sufficient or effective to prevent or treat (delay or prevent the onset of, prevent the progression of, inhibit, decrease or reverse) a disease or condition, including alleviating symptoms of such diseases. An "effective amount" of a delivery vehicle is that amount sufficient to effectively bind or deliver a compound.

DETAILED DESCRIPTION OF THE INVENTION

The AAV vector according to the invention is typically made of 2 components:

The encapsidated recombinant nucleic acid sequence which defines the expression cassette (construct) that provides the therapeutic benefit(s) once expressed in the target cell/tissue; and The viral capsid which allows proper gene transfer and to a certain extent, tissue tropism.

In one embodiment, the present invention relates to an adeno-associated viral (AAV) vector containing an expression construct, wherein:

the expression construct comprises a nucleic acid sequence which encodes a microdystrophin (MD); and
the nucleic acid sequence encoding the MD has a size of at least 4.1 kb.

According to one aspect, the adeno-associated viral (AAV) vector of the invention comprises an expression construct, also named "expression cassette" or "insert". In the frame of the present application, said "insert" is advantageously defined as the nucleic acid sequence located between the 5' and 3' ITR ("Inverted Terminal Repeat") sequences of the AAV genome, including said ITR sequences.

According to common knowledge in the art, the size of the insert should not exceed the wild-type AAV genome length. For example, AAV2 contains 2 ITR sequences of 145 bp each and has a genome of 4682 pb (including the ITR sequences).

According to one embodiment, the expression construct comprises a nucleic acid sequence which encodes a microdystrophin (MD), advantageously a functional microdystrophin.

In the frame of the present application, microdystrophin means a peptide or protein which is shorter than the native or wild type dystrophin. In the context of the invention, the terms "microdystrophin" and "minidystrophin" have the same meaning. In the rest of the application, the term "microdystrophin" will be used, as well as the abbreviations "MD" or "µDys".

The structure of dystrophin is well documented (see FIG. 1) and active fragments thereof have been disclosed (Athanasopoulos et al., Gene Ther 2004 Suppl 1:S109-21). As would be understood in the art, an active fragment is a portion or portions of a full length sequence that retain at least some of the biological functions of the full length sequence.

A "functional" microdystrophin means that the corresponding peptide or protein is able to perform at least some of the functions of the wild-type dystrophin protein and is able to alleviate, at least partially, one or more of the symptoms associated with the absence of a native dystrophin, especially fiber degeneration, inflammation, necrosis, replacement of muscle with scar and fat tissue, muscle weakness, respiratory and cardiac failure, as well as premature death.

According to the invention, it is preferred that the microdystrophin displays (to a greater or lesser extent) at least one of the properties disclosed in relation with the microdystrophins of the prior art, especially MD1 (Yue, et al., Mol Ther, 2006. 14(1): 79-87) and MD2 (Koo et al., Hum Gene Ther, 2011. 22: 1379-1388).

Among others, preferred properties are:
 Binding with at least one DAP ("dystrophin associated proteins"), especially with syntrophin, dystrobrevin, nNOS and/or PAR-1b proteins;
 Recruitment of the DAP complex at the sarcolemma;
 Rescue of the microtubule network;
 Muscle protection from damage;
 Restoration of muscle structure and function. Of particular interest are the skeletal muscles, but also the cardiac muscle and the diaphragm;
 More generally, amelioration of muscular function, gait, cardiac function, respiratory function, survival, quality and/or expectancy of life.

As known in the art, said properties can be tested in vitro on human DMD myoblasts, ex vivo on muscle fibres isolated from e.g. mouse model, or in vivo based on animal models or even on patients suffering from DMD or BMD. Animal models are e.g. the mdx mouse (Foster H. et al., Mol Ther, 2008. 16(11): p. 1825-32), the mdx$^{4cv}$ mouse (Decrouy et al., Gen Ther, 1997. 4(5): 401-8), the CXMDj dog (Koo et al., J Gene Med, 2011. 13(9): 497-506) or the GRMD dog (Le Guiner et al., Mol Ther., 2014. 22(11): 1923-35). The mouse model is commonly used to test new constructs encoding microdystrophins. However, this model has drawbacks because the mouse displays a less severe form of the disease, without immune reactions. The other animal model is the dog which is considered more reliable to predict the therapeutic potential of a gene therapy product in humans.

As mentioned above, the full length dystrophin is characterized by different domains:

A N-terminal domain which binds to actin;
4 hinge domains (H1 to H4);
24 spectrin-like repeats or rod domains (R1 to 24);
A cysteine-rich (CR) domain;
A C-terminal (CT) domain.

According to one embodiment, the microdystrophin has at least one domain lacking, advantageously at least one spectrin-like-repeat.

According to a particular embodiment, the microdystrophin of the invention is derived from functional microdystrophins of the prior art (FIG. 1), in particular:
 The MD1 (ΔR4-R23/ΔCT) protein of around 1200 amino acids (aa), comprising 4 spectrin-like repeats, i.e. spectrin-like repeats 1, 2, 3 and 24. More precisely, this sequence comprises deletions of rod domains 4-23 and exons 71-78 of the CT domain of dystrophin, and contains the last three amino acids of exon 79 of dystrophin followed by three stop codons;
 The MD2 protein of around 1340 aa: MD1 having helix 1 of the coiled-coil motif in the C-terminal domain of dystrophin.

Advantageously, the microdystrophins according to the invention contains further CT domains.

Of particular interest are microdystrophin having a further extended C-terminal domain, i.e. a partial or full-length CT domain. Indeed, the C-terminal region of dystrophin may have an important function in the full assembly of the DAP complex, including members of syntrophin and dystrobrevin protein families, which have been implicated in signalling:
 Amino acids 457-497 of dystrobrevin bind to the first set of heptad repeats of dystrophin (amino acids 3,501-3,541);
 The α1-syntrophin, and β1-syntrophin binding site is delineated to exon 73-74, and exon 74-75 of dystrophin, respectively. Syntrophin (α, β1, and β2) interacts with several proteins including nNOS, voltage-gated sodium channels, stress-activated protein kinase-3, and a microtubule-associated serine/threonine kinase. Interaction between α1-syntrophin, nNOS and plasma membrane $Ca^{2+}$/calmodulin-dependent ATPase was also found;
 The dystrobrevin family (α and β) binds both syntrophin and the coiled coil motifs of the CT domain of dystrophin. Dystrobrevin has a signalling function and contributes to the structural stability of dystrophin containing glycoprotein complex (DGC). Dp71, one of the C-terminal dystrophin isoforms predominantly localises to the nucleus, which implies the potential function of the C-terminal dystrophin in the nucleus.

Advantageously, such microdystrophins comprise the coiled-coil region helix 1 and 2 (encoded by exons 70 to 75) or the entire CT domain (encoded by exons 70 to 79). According to a specific embodiment, they are derived from MD1 and comprise 4 spectrin-like repeats, i.e. spectrin-like repeats 1, 2, 3 and 24 (ΔR4-R23), and a C-terminal domain as defined above.

As illustrated in FIG. 1, specific examples are the microdystrophins:
 MD3 which amino acid sequences are shown in SEQ ID NO: 1 (1394 aa), SEQ ID NO: 7 (1393 aa) or SEQ ID NO: 13 (1392 aa); and
 MD4 which amino acid sequences are shown in SEQ ID NO: 4 (1473 aa), SEQ ID NO: 10 (1472 aa) or SEQ ID NO: 16 (1471 aa),
respectively.

According to a preferred embodiment, the microdystrophin to be produced with the claimed AAV vector contains at least 1350 amino acids (aa), advantageously at least 1400 aa, 1450 aa, 1500 aa, or 1550 aa. According to another embodiment, the microdystrophin to be produced with the claimed AAV vector contains no more than 1800 amino acids (aa), advantageously no more than 1750 aa, 1700 aa, 1650 aa, or 1600 aa.

According to one embodiment, the microdystrophin to be produced with the claimed AAV vector is "substantially identical", that is, is about 60% identical, more preferably about 70% identical, even more preferably about 80% identical, more preferably about 90%, 91%, 92%, 93%, 94%, 95%, 96%, 97%, 98% or even more preferably about 99% identical to the microdystrophins disclosed therein, especially those of sequence SEQ ID NO: 1, SEQ ID NO: 7, SEQ ID NO: 13, SEQ ID NO: 4, SEQ ID NO: 10 or SEQ ID NO: 16.

The present invention also concerns nucleic acid sequences encoding such a microdystrophin.

In one embodiment, the nucleic acid sequence comprised in the expression construct and encoding the microdystrophin (MD), also named ORF for "open reading frame", is a cDNA. However, e.g. single- or double-stranded DNA or RNA can be used.

In the frame of the invention, nucleic acid sequences encoding microdystrophin (MD) are shorter than the wild-type dystrophin cDNA.

According to one specific embodiment of the present invention, the size of the nucleic acid sequence encoding the microdystrophin (ORF) exceeds 4 kb (4000 bp). According to one preferred embodiment, the nucleic acid sequence encoding the MD has a size of at least 4050 pb (4.05 kb), preferably 4100 bp (4.1 kb) or even more preferably of at least 4150, 4200, 4250, 4300, 4350, 4400, 4450, 4500, 4550, 4600, 4650, 4700, 4750, 4800, 4850, 4900, 4950, or 5000 bp.

According to a specific embodiment, the AAV vector according to the invention is not used in combination with a proteasome inhibitor. Alternatively, the AAV vector according to the invention is used in combination with a proteasome inhibitor. In the frame of the application, the wording "used in combination" is similar to "combined" or "associated" and means that both (the AAV vector and the proteasome inhibitor) can be formulated in the same composition, or formulated in two distinct compositions for simultaneous, separate or sequential administration. Proteasome inhibitors are molecules (chemical compounds, peptides, proteins, antibodies, nucleic acids . . . ) able to block the action of proteasomes, protease complexes which are responsible for degrading proteins. Examples include: Lactacystin, Bortezomib, Disulfiram, Epigallocatechin-3-gallate, Carfilzomib, Celastrol, ONX0912, CEP-18770, MLN9708, Marizomib, Epoxomicin, LLnL (N-acetyl-$_L$-leucinyl-$_L$-leucinyl-nor-leucinal) and MG132.

The nucleic acid sequence encoding the microdystrophin is advantageously of human origin but can also be a canine, a rat, a murine or a non-human primate sequence. In one embodiment, the nucleic acid sequence originates from the organism it will be administered to (e.g. a human sequence in humans).

Basically, the nucleic acid sequence encoding the microdystrophin (MD) is an open reading frame beginning with a start codon and ending with a stop codon. However and according to a specific embodiment, said sequence can be modified in different ways.

According to one preferred embodiment, the nucleic acid sequence encoding said microdystrophin is optimized for use in a given subject, advantageously in humans. Preferably, the sequence is modified as follows:

The sequence is modified to include a consensus Kozak sequence before AUG start codon within mRNA, to improve initiation of translation.

The sequence is optimized based on transfer RNA frequencies in the subject (preferably human) and GC content is increased to promote RNA stability. As a result and in a specific case, codon optimization for humans advantageously leads to 63% of codons being modified and the GC content increased to over 60%. This of course depends on the original (before optimization) microdystrophin sequence and the target host.

In relation with the microdystrophins disclosed above, said nucleic acid sequence is advantageously chosen in the group consisting of: SEQ ID NO: 2 (mMD3), SEQ ID NO: 5 (mMD4), SEQ ID NO: 8 (cMD3), SEQ ID NO: 11 (cMD4), SEQ ID NO: 14 (hMD3), SEQ ID NO: 17 (hMD4), or a sequence substantially identical thereto.

According to one embodiment, the nucleotide sequence of an isolated nucleic acid encoding a peptide of the invention is "substantially identical", that is, is about 60% identical, more preferably about 70% identical, even more preferably about 80% identical, more preferably about 90%, 91%, 92%, 93%, 94%, 95%, 96%, 97%, 98% or even more preferably about 99% identical to said sequences.

As mentioned above, the expression construct comprises the nucleic acid sequence encoding the transgene of interest, in the present case a microdystrophin (MD), the 2 ITR sequences but also all the sequences required for a proper expression of said MD.

According to another embodiment, the AAV vector of the invention contains an expression construct (including the 2 ITR sequences) which has a size exceeding 5 kb or even 5.1 kb.

According to a preferred embodiment, the expression construct has a size of at least 5100 pb (5.1 kb), preferably 5150 bp, or even more preferably of at least 5200, 5250, 5300, 5350, 5400, 5450, 5500, 5550, 5600, 5650, 5700, 5750, 5800, 5850, 5900, 5950, or 6000 bp. According to a specific case, this embodiment is in the absence of any proteasome inhibitor.

According to another embodiment, the expression construct has a size of less than 7000 bp (7 kb), preferably of less than 6500 pb, or even more preferably of less than 6450, 6400, 6350, 6300, 6250, 6200, 6150, 6100, 6050, or even 6000 bp. According to a specific case, this embodiment is in the absence of any proteasome inhibitor.

Advantageously, the size of the expression construct is between 5.1 and 6 kb, advantageously between 5.2 and 5.8 kb, more advantageously between 5.15 and 5.75 kb. Without being bound to any theory, a controlled size of the invert prevents the so called fragmentation.

In one embodiment, the expression construct further comprises regulatory sequences, especially a promoter sequence. Such promoters can be natural or synthetic (artificial) promoters, inducible or constitutive.

In one embodiment, the promoter is an ubiquitous promoter or having a low tissue-specificity. As an example, the expression vector can harbor the phosphoglycerate kinase 1 (PGK), EF1, β-actin, CMV promoter.

In a preferred embodiment, the promoter sequence is chosen in order to adequately govern the expression of the nucleic acid sequence placed under its control, in terms of expression level, but also of tissue specificity.

In one embodiment, the expression vector comprises a muscle specific promoter. Such a promoter allows a robust expression in the skeletal muscles, and possibly in the cardiac muscle as well as in the diaphragm. Examples of suitable promoters known by the skilled person are e.g. the desmin promoter, the muscle creatine kinase (MCK) promoter, truncated creatine kinase promoters such as e.g. CK6, CK7 or CK8 promoter, and the Syn promoter. Another promoter is the synthetic promoter C5-12 (spC5-12) of 334 bp size as shown for example in sequence SEQ ID NO: 3 (nucleotides 253 to 586), or derivatives thereof, which allow a robust expression in skeletal and cardiac muscles.

Advantageously, the nucleic acid sequence encoding the MD is placed under the control of a muscle-specific promoter. In other words, the expression construct further comprises a muscle-specific promoter which is operably linked to the nucleic acid sequence encoding the MD.

A non-exhaustive list of other possible regulatory sequences to be inserted in the expression construct encoding the microdystrophin is:
- a polyadenylation signal, e.g. the polyA of the gene of interest, the polyA of SV40 or of beta hemoglobin (HBB2), advantageously in 3' of the sequence encoding the microdystrophin; The poly A of SV40 is for example disclosed in sequence SEQ ID NO: 3 (nucleotides 4852 to 5091);
- sequences for transcript stabilization, e.g. intron 1 of hemoglobin (HBB2);
- enhancer sequences;
- miRNA target sequences, which can inhibit the expression of the sequence encoding the microdystrophin in non target tissues, in which said expression is not desired, for example where it can be toxic. Preferably, the corresponding miRNA is not present in the skeletal muscles, and possibly not in the diaphragm nor in the heart. Of particular interest are molecules or sequences which prevent expression in the cells of the hematopoietic (immune) system and the liver.

As previously mentioned and for recombinant AAV production, the nucleic acid sequence encoding the microdystrophin is inserted between the ITR («Inverted Terminal Repeat») sequences of an AAV vector, advantageously of serotype 2 (http://www.biotechniques.com/multimedia/archive/00232/BTN_A_000114170_O_2326 25a.pdf)). Typical ITR sequences correspond to:
- nucleotides 1 to 145 of sequence SEQ ID NO: 3 (5'ITR sequence);
- nucleotides 5138 to 5283 of sequence SEQ ID NO: 3 (3'ITR sequence).

In relation with the large-sized microdystrophins disclosed therein, the gene therapy product i.e. the AAV vector advantageously comprises or consists of a sequence selected from the group consisting of: SEQ ID NO: 3 (mMD3), SEQ ID NO: 6 (mMD4), SEQ ID NO: 9 (cMD3), SEQ ID NO: 12 (cMD4), SEQ ID NO: 15 (hMD3) and SEQ ID NO: 18 (hMD4).

As mentioned above, the invention also encompasses "substantially identical" sequences, that is, displaying about 60% identity, more preferably about 70% identity, even more preferably about 80% identity, more preferably about 90%, 91%, 92%, 93%, 94%, 95%, 96%, 97%, 98% or even more preferably about 99% identical to said sequences.

For cloning purposes and production of viral particles, the expression construct can be inserted in a plasmid suitable for selection, replication and production of the cloned MD.

According to the invention, the viral vector containing the expression construct is an adeno-associated viral (AAV) vector.

Adeno-associated viral (AAV) vectors have become powerful gene delivery tools for the treatment of various disorders. AAV vectors possess a number of features that render them ideally suited for gene therapy, including a lack of pathogenicity, moderate immunogenicity, and the ability to transduce postmitotic cells and tissues in a stable and efficient manner. Expression of a particular gene contained within an AAV vector can be specifically targeted to one or more types of cells by choosing the appropriate combination of AAV serotype, promoter, and delivery method.

In one embodiment, the encoding sequence is contained within an AAV vector. More than 100 naturally occurring serotypes of AAV are known. Many natural variants in the AAV capsid exist, allowing identification and use of an AAV with properties specifically suited for dystrophic pathologies. AAV viruses may be engineered using conventional molecular biology techniques, making it possible to optimize these particles for cell specific delivery of nucleic acid sequences, for minimizing immunogenicity, for tuning stability and particle lifetime, for efficient degradation, for accurate delivery to the nucleus.

As mentioned above, the use of AAVs is a common mode of exogenous delivery of DNA as it is relatively non-toxic, provides efficient gene transfer, and can be easily optimized for specific purposes. Among the serotypes of AAVs isolated from human or non-human primates (NHP) and well characterized, human serotype 2 is the first AAV that was developed as a gene transfer vector. Other currently used AAV serotypes include AAV1, AAV3, AAV4, AAV5, AAV6, AAV7, AAV8, AAV9, AAV10, AAV11 and AAV12. In addition, non-natural engineered variants and chimeric AAV can also be useful.

Desirable AAV fragments for assembly into vectors include the cap proteins, including the vp1, vp2, vp3 and hypervariable regions, the rep proteins, including rep 78, rep 68, rep 52, and rep 40, and the sequences encoding these proteins. These fragments may be readily utilized in a variety of vector systems and host cells.

Such fragments may be used alone, in combination with other AAV serotype sequences or fragments, or in combination with elements from other AAV or non-AAV viral sequences. As used herein, artificial AAV serotypes include, without limitation, AAV with a non-naturally occurring capsid protein. Such an artificial capsid may be generated by any suitable technique, using a selected AAV sequence (e.g., a fragment of a vp1 capsid protein) in combination with heterologous sequences which may be obtained from a different selected AAV serotype, non-contiguous portions of the same AAV serotype, from a non-AAV viral source, or from a non-viral source. An artificial AAV serotype may be, without limitation, a chimeric AAV capsid, a recombinant AAV capsid, or a "humanized" AAV capsid. Thus exemplary AAVs, or artificial AAVs, include AAV2/8 (U.S. Pat. No. 7,282,199), AAV2/5 (available from the National Institutes of Health), AAV2/9 (WO2005/033321), AAV2/6 (U.S. Pat. No. 6,156,303), and AAVrh8 (WO2003/042397), among others. In one embodiment, the vectors useful in the compositions and methods described herein contain, at a minimum, sequences encoding a selected AAV serotype capsid, e.g., an AAV8 capsid, or a fragment thereof. In another embodiment, useful vectors contain, at a minimum, sequences encoding a selected AAV serotype rep protein, e.g., AAV8 rep protein, or a fragment thereof. Optionally, such vectors may contain both AAV cap and rep proteins. In vectors in which both AAV rep and cap are provided, the AAV rep and AAV cap sequences can both be of one serotype origin, e.g., all AAV8 origin. Alternatively, vectors may be used in which the rep sequences are from an AAV serotype, which differs from that which is providing the cap sequences. In one embodiment, the rep and cap sequences are expressed from separate sources (e.g., separate vectors, or a host cell and a vector). In another embodiment, these rep sequences are fused in frame to cap sequences of a different AAV serotype to form a chimeric AAV vector, such as AAV2/8 (U.S. Pat. No. 7,282,199).

According to one embodiment, the composition comprises an AAV of serotype 2, 5, 8 or 9. Advantageously, the claimed vector is an AAV8 or AAV9 vector, especially an AAV2/8 or AAV2/9 vector. More advantageously, the claimed vector is an AAV8 vector or an AAV2/8 vector.

In the AAV vectors used in the present invention, the AAV genome may be either a single stranded (ss) nucleic acid or a double stranded (ds), self complementary (sc) nucleic acid.

As known in the art, recombinant viral particles can be obtained, e.g. by tri-transfection of 293 HEK cells, by the herpes simplex virus system and by the baculovirus system. Advantageously, the viral particles are obtained by tri-transfection of 293 HEK cells.

The vector titers are usually expressed as viral genomes per ml (vg/ml). In a surprising manner and despite the large size of the MD disclosed in the present invention, viral titers above $1.10^{11}$, preferably above $5.10^{11}$, $1.10^{12}$, $5.10^{12}$ and even more preferably above $1.10^{13}$ vg/ml can be obtained.

According to another aspect, the present invention concerns a composition, advantageously a therapeutic composition or medicament, comprising the AAV vector as disclosed above and possibly other active molecules (other gene therapy products, chemical molecules, peptides, proteins, . . . ), dedicated to the treatment of the same disease or another disease.

According to a specific embodiment, the composition does not comprise any proteasome inhibitor. Alternatively, said composition further comprises a proteasome inhibitor.

The present invention then provides pharmaceutical compositions comprising a nucleic acid of the invention, or the vector of the invention. Such compositions comprise a therapeutically effective amount of the therapeutic (the nucleic acid or vector of the invention), and a pharmaceutically acceptable carrier. In a specific embodiment, the term "pharmaceutically acceptable" means approved by a regulatory agency of the Federal or a state government or listed in the U.S. or European Pharmacopeia or other generally recognized pharmacopeia for use in animals, and humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents. These compositions can take the form of solutions, suspensions, emulsions, sustained-release formulations and the like. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the subject.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to release pain at the site of the injection.

In one embodiment, the composition according to the invention is suitable for administration in humans. The composition is preferably in a liquid form, advantageously a saline composition, more advantageously a phosphate buffered saline (PBS) composition or a Ringer-Lactate solution.

The amount of the therapeutic (i.e. a nucleic acid or a vector) of the invention which will be effective in the treatment of dystrophic diseases can be determined by standard clinical techniques. In addition, in vivo and/or in vitro assays may optionally be employed to help predict optimal dosage ranges. The precise dose to be employed in the formulation will also depend on the route of administration, the weight and the seriousness of the disease, and should be decided according to the judgment of the practitioner and each patient's circumstances.

The above-disclosed AAV vector or composition can be used as a medicament, especially as a gene therapy product, to be administered to a subject in need thereof. According to another aspect, the present invention concerns the use of the above-disclosed AAV vector or composition for the preparation of a medicament.

Suitable administration should allow the delivery of a therapeutically effective amount of the gene therapy product to the target tissues, especially skeletal muscles and possibly diaphragm and heart. In the context of the invention, when the gene therapy product is a viral vector comprising a nucleic acid sequence encoding a microdystrophin, the therapeutic dose is defined as the quantity of viral particles (vg for viral genomes) containing the microdystrophin sequence, administered per kilogram (kg) of the subject.

Available routes of administration are topical (local), enteral (system-wide effect, but delivered through the gastrointestinal (GI) tract), or parenteral (systemic action, but delivered by routes other than the GI tract). Preferred route of administration of the compositions disclosed herein is parenteral and includes intramuscular administration (i.e. into the muscle) and systemic administration (i.e. into the circulating system). In this context, the term "injection" (or "perfusion" or "infusion") encompasses intravascular, in particular intravenous (IV), and intramuscular (IM) administration. Injections are usually performed using syringes or catheters.

In one embodiment, systemic delivery of the composition comprises administering the composition near a local treatment site, i.e. in a vein or artery nearby a weakened muscle. In certain embodiments, the invention comprises the local delivery of the composition, which produces systemic effects. This route of administration, usually called "regional (loco-regional) infusion", "administration by isolated limb perfusion" or "high-pressure transvenous limb perfusion" has been successfully used as a gene delivery method in muscular dystrophy (Zheng Fan et al. (2012, Molecular Therapy 20(2), 456-461).

According to one aspect, the composition is administered to an isolated limb (loco-regional) by infusion or perfusion. In other words, the invention comprises the regional delivery of the composition in a leg and/or arm by an intravascular route of administration, i.e. a vein (transveneous) or an artery, under pressure. This is usually achieved by using a tourniquet to temporarily arrest blood circulation while allowing a regional diffusion of the infused product, as e.g. disclosed by Toromanoff et al. (2008, Molecular Therapy 16(7):1291-99), Arruda et al. (2010, Blood 115(23):4678-88) and Zheng Fan et al. (2012, Molecular Therapy 20(2), 456-461).

In one embodiment, the composition is injected in a limb of the subject. In one embodiment, the subject is a mammal, preferably a human, a dog or a nonhuman primate. When the subject is a human, the limb can be the arm or the leg. According to one embodiment, the composition is administered in the lower part of the body of the subject, e.g. below the knee, or in the upper part of the body of the subject, e.g., below the elbow.

In one embodiment, the composition is administered to a peripheral vein, e.g. the cephalic vein. The volume of the composition to be infused can be in a range that varies between about 5 and 40% of the limb volume. The typical dose can vary between 5 and 30 ml/kg of body weight. In one embodiment, the pressure to be applied (tourniquet pressure or maximum line pressure) is below 100 000 Pa, advantageously below 50 000 Pa. In a preferred embodiment, the pressure applied is around 300 torr (40 000 Pa).

In one embodiment, the blood circulation of the limb is stopped using a tourniquet that is tightened for several minutes to more than one hour, typically between about 1 and 80 minutes, for example about 30 minutes. In a preferred embodiment, the tourniquet was applied before, during and after the administration, for example about 10 minutes prior to, about 20 minutes during and about 15 min after the infusion. More generally, the pressure is applied for several minutes, typically between about 1 and 80 minutes, for example about 30 minutes. In a preferred embodiment, the pressure is applied before, during and after the administration, for example about 10 minutes prior to, about 20 minutes during and about 15 minutes after the infusion.

In one embodiment, the average flow rate is comprised between 5 and 150 ml/min, advantageously between 5 and 80 ml/min, for example 10 ml/min. Of course, the flow rate also determines the time period during which the blood circulation is stopped and the pressure applied.

A preferred method of administration according to the invention is systemic administration. Systemic injection opens the way to an injection of the whole body, in order to reach the entire muscles of the body of the subject including the heart and the diaphragm and then a real treatment of these systemic and still incurable diseases. In certain embodiments, systemic delivery comprises delivery of the composition to the subject such that composition is accessible throughout the body of the subject.

According to a preferred embodiment, systemic administration occurs via injection of the composition in a blood vessel, i.e. intravascular (intravenous or intra-arterial) administration. According to one embodiment, the composition is administered by intravenous injection, through a peripheral vein. Alternatively, systemic administration occurs via intramuscular injection.

According to one embodiment, the composition is administered by intravenous injection, through a peripheral vein.

The systemic administration is typically performed in the following conditions:
 a flow rate of between 1 to 10 ml/min, advantageously between 1 to 5 ml/min, e.g. 3 ml/min;
 the total injected volume can vary between 1 and 10 ml, preferably 5 ml of vector preparation per kg of the subject. The injected volume should not represent more than 10% of total blood volume, preferably around 6%.

When systemically delivered, the composition is preferably administered with a dose less than or equal to $10^{15}$ vg/kg or even $10^{14}$ vg/kg, advantageously between $10^{12}$ vg/kg and $10^{14}$ vg/kg, more advantageously between $5.10^{12}$ vg/kg and $10^{14}$ vg/kg, e.g. 1, 2, 3, 4, 5, 6, 7, 8 or $9.10^{13}$ vg/kg. A lower dose of e.g. 1, 2, 3, 4, 5, 6, 7, 8 or $9.10^{12}$ vg/kg can also be contemplated in order to avoid potential toxicity and/or immune reactions. As known by the skilled person, a dose as low as possible given a satisfying result in term of efficiency is preferred.

In a specific embodiment, the treatment comprises a single administration of the composition.

In one embodiment, the presence of the AAV vector and/or the expression of the microdystrophin, as well as the associated therapeutic benefits, are observed for up to 1 month, or 3 months or 6 months or even 1 year, 2 years, 5 years, 10 years, or even more the whole life of the subject.

According to the invention, the subject is preferably a human, but can also be a mouse, a rat, a nonhuman primate or a dog.

"Dystrophic disease" means a disease linked to a defect in the dystrophin gene. This defect can be deletions or mutations leading to low level of expression or absence of expression, introduction of a premature stop codon in the open reading frame, or the production of an inactive protein. Preferred dystrophic diseases are Duchenne and Becker muscular dystrophy (DMD/BMD) caused by mutations of the dystrophin gene. Said mutations can result in the absence or a low level of dystrophin expression, or in the production of a partially or fully inactive, possibly truncated, protein.

Subjects that could benefit from the compositions of the invention include all patients diagnosed with a muscular dystrophy or at risk of developing such a muscular dystrophy. A subject to be treated can then be selected based on the identification of mutations or deletions in the dystrophin gene by any method known to the one skilled in the art, including for example sequencing of the dystrophin gene, and/or through the evaluation of the dystrophin level of expression or activity by any method known to the one skilled in the art. Therefore, said subjects include both subjects already exhibiting symptoms of a dystrophic disease and subjects at risk of developing said disease. In one embodiment, said subjects include subjects already exhibiting symptoms of a dystrophic disease. In another embodiment, said subjects are ambulatory patients and early non-ambulant patients.

According to one embodiment, the invention concerns an AAV vector as disclosed above or a composition comprising said AAV vector for use in the treatment of a dystrophic disease. According to another embodiment, the invention concerns the use of an AAV vector as disclosed above or a composition comprising said AAV vector for the preparation of a medicament for the treatment of a dystrophic disease.

In other words, the present invention provides a method for treating a dystrophic disease in a subject, comprising administrating to the subject an AAV vector as disclosed above or a composition comprising said AAV vector.

According to a specific embodiment, the claimed treatment is not combined with a treatment with a proteasome inhibitor. Alternatively, the subject is treated with a proteasome inhibitor in a simultaneous, separate or sequential manner.

Such AAV vectors and compositions comprising said vectors are notably intended for gene therapy, particularly for the treatment of subjects suffering from Duchenne muscular dystrophy (DMD) or Becker muscular dystrophy (BMD). A first target of is to provide a safe (not toxic) treatment. A further aim is to provide an efficient treatment which allows to postpone, slow down or prevent the development of the disease, and possibly to ameliorate the phenotype of the patient which can be easily monitored at the clinical level. In a subject, AAV vectors and compositions according to the invention can be used:

for ameliorating muscular function. Of particular interest are the skeletal muscles, but also the cardiac muscle and the diaphragm;
for ameliorating gait;
for ameliorating cardiac function;
for ameliorating respiratory function;
for prolonging survival, more generally to ameliorate the quality and the expectancy of life.

In conclusion, the present invention reports the possibility to use AAV vectors, especially of serotype 8 and 9, for packaging nucleic acid sequences encoding large-sized microdystrophins. As a result, it is possible to design new microdystrophins having further domains potentially relevant for improved activity.

As illustrated in the examples below and in an unexpected manner, it is possible to obtain:

an acceptable level of viral particles compatible with in vivo applications;
an acceptable level of "intact" (not deleted) and active microdystrophins.

Therefore, AAV vectors encoding large-sized microdystrophins are potential gene therapy products with the following characteristics:

A product which can be systemically (e.g. by intramuscular injection, intravascular injection, especially intravenous injection, or by loco-regional administration) administered, at a reasonable dose (i.e. a proper gene transfer in the target tissues) and possibly by a unique injection;
A product which has acceptable toxicity at that dose, and especially does not induce an adverse immune response against the dystrophin protein;
A product having a satisfying tropism, i.e. a wide spread gene transfer on large territories of skeletal muscles, but also diaphragm and myocardium;
A product able to ameliorate the dystrophic disease in humans.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

The disclosures of each and every patent, patent application, and publication cited herein are hereby incorporated herein by reference in their entirety.

Without further description, it is believed that one of ordinary skill in the art can, using the preceding description and the following illustrative examples, make and utilize the compounds of the present invention and practice the claimed methods.

EXPERIMENTAL EXAMPLES

The invention is further described in detail by reference to the following experimental examples and the attached figures. These examples are provided for purposes of illustration only, and are not intended to be limiting.

C2C12 myoblast cultures were transfected with pAAV-mMD1, -mMD2, -mMD3, and -mMD4 plasmids (tracks 1-4) or with no DNA (track 5 and 6). After 2 days, RNA was isolated and analysed by RT-PCR using primers (panel A), while RNA was analysed by PCR using same primers (panel B). Lane 7 in panel B shows a positive control samples amplifying from pAAVmMD1 plasmids. PCR products were analysed by 1% agarose gel electrophoresis and visualised by ethidium bromide staining.

Figure 4:
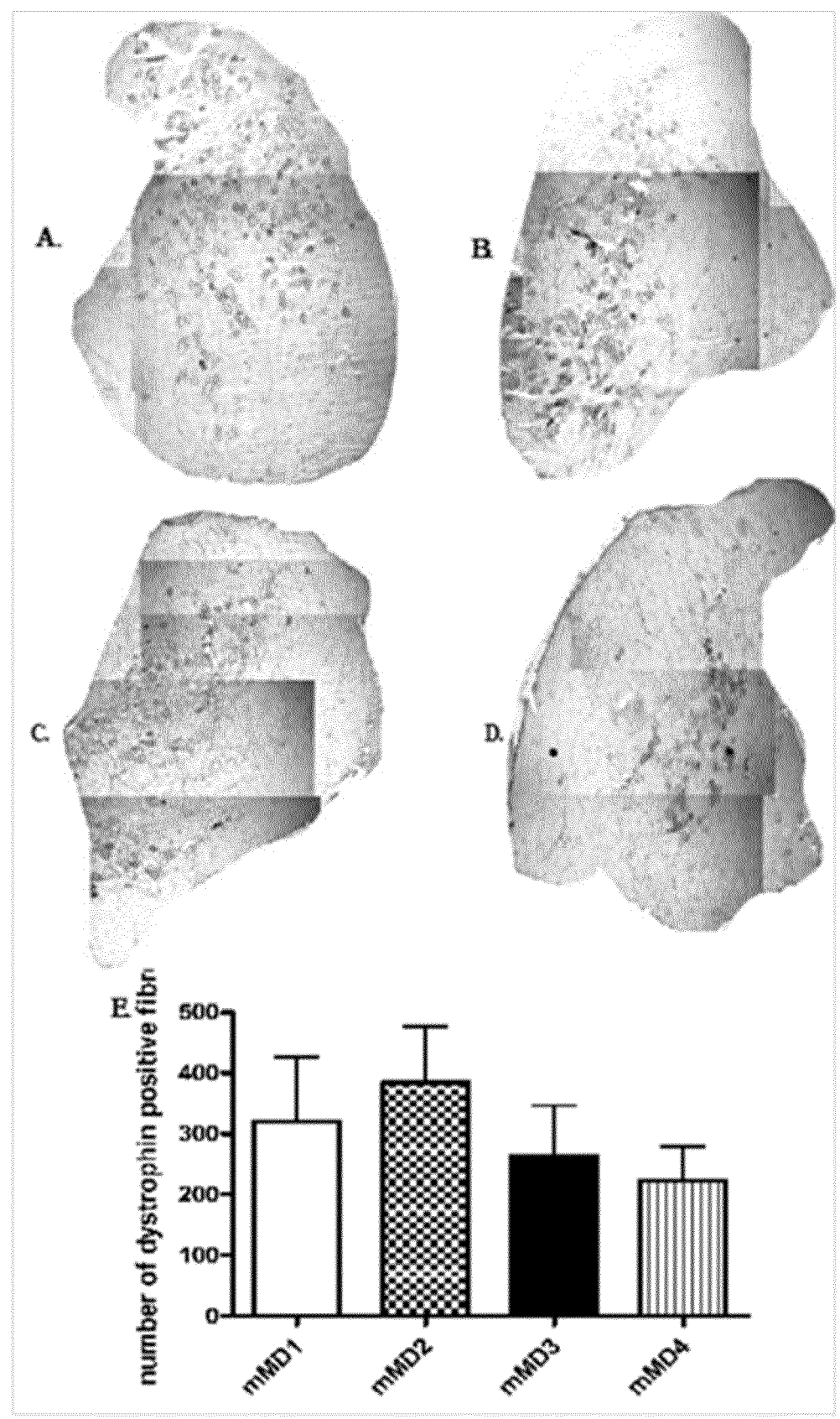

FIG. 4: Examination of expression of mouse specific microdystrophin variants in mdx muscle following in vivo muscle electrotransfer of plasmid vectors.

Plasmid vectors were introduced into TA muscles of mdx mice by eletrotranfer. After 8 days, muscles were recovered and subjected to immunohistology for the dystrophin staining. Low magnification bright-field micrographs are shown for pAAV mMD1 (A), pAAVmMD2 (B), pAAV mMD3 (C) and pAAV mMD4 (D). The number of microdystrophin-positive fibres were counted as described in the histogram (E); mean±SE (n=4). There was no significant difference between the constructs by statistical analysis.

Figure 5:
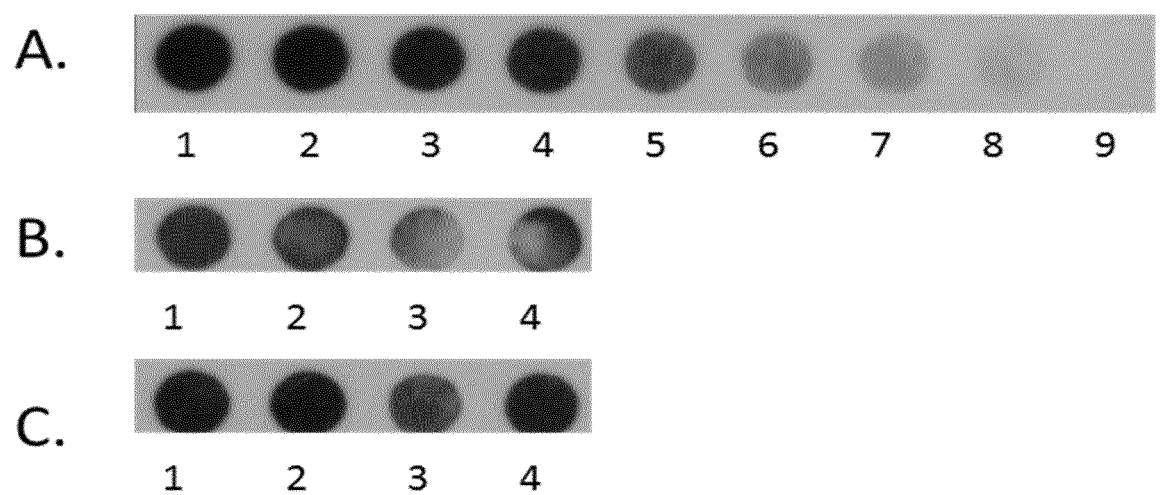

FIG. 5: Determination of AAV vector concentrations by dot-blot hybridisation.

Samples of AAV vector preparations were lysed by treatment with proteinase K, and viral DNA was purified and spotted onto a membrane filter, along with a series of plasmid standards. Filters were then hybridised to a digoxin-labelled probe, and developed with anti-digoxin antibody, the ECL system, and exposure of filters to X-ray film. A montage of developed X-ray film is shown. A. pAAV-mMD1 plasmid standards: 1. 160 ng, 2. 80 ng, 3. 40 ng, 4. 20 ng, 5. 10 ng, 6. 5 ng, 7. 2.5 ng, 8. 1.25 ng, 9. 0.625 ng. B. Extracts of AAV preparations (1 ml): 1. AAV2/9-mMD1, 2. AAV2/9-mMD2, 3. AAV2/9-mMD3, 4. AAV2/9-mMD4. C. Extracts of AAV preparations (2 ml): 1. AAV2/9-mMD1, 2. AAV2/9-mMD2, 3. AAV2/9-mMD3, 4. AAV2/9-mMD4.

Figure 6:
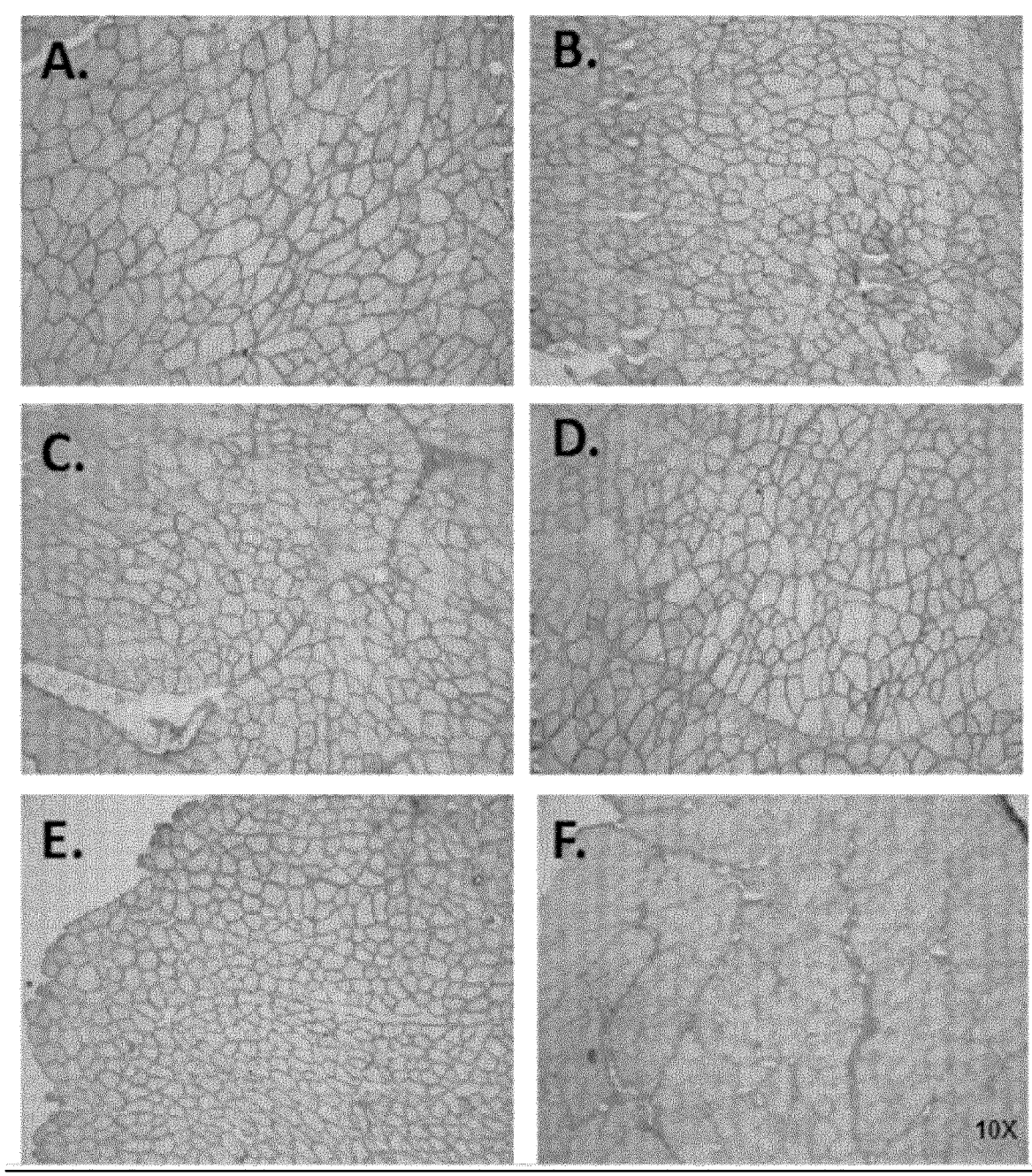

FIG. 6: Assessment of dystrophin immunolabelling in cryosections of mdx muscles injected with AAV2/9 vectors expressing the mMD1, mMD2, mMD3 and mMD4 microdystrophin variants.

The TA muscles of eight week old mdx mice were injected with $2 \times 10^{10}$ vg of AAV 2/9-mMD1, mMD2, mMD3, and mMD4. TA muscles were recovered eight weeks after injection and processed for cryosectioning. The sections were subjected to immunochemical labelling with an antibody (Manex 1011C) against dystrophin. Panels A-F shows AAV2/9-mMD1, mMD2, mMD3, mMD4, C57BL10 and mdx, respectively. Control muscle from age-matched mdx and C57BL/10 were injected with saline only.

Figure 7:
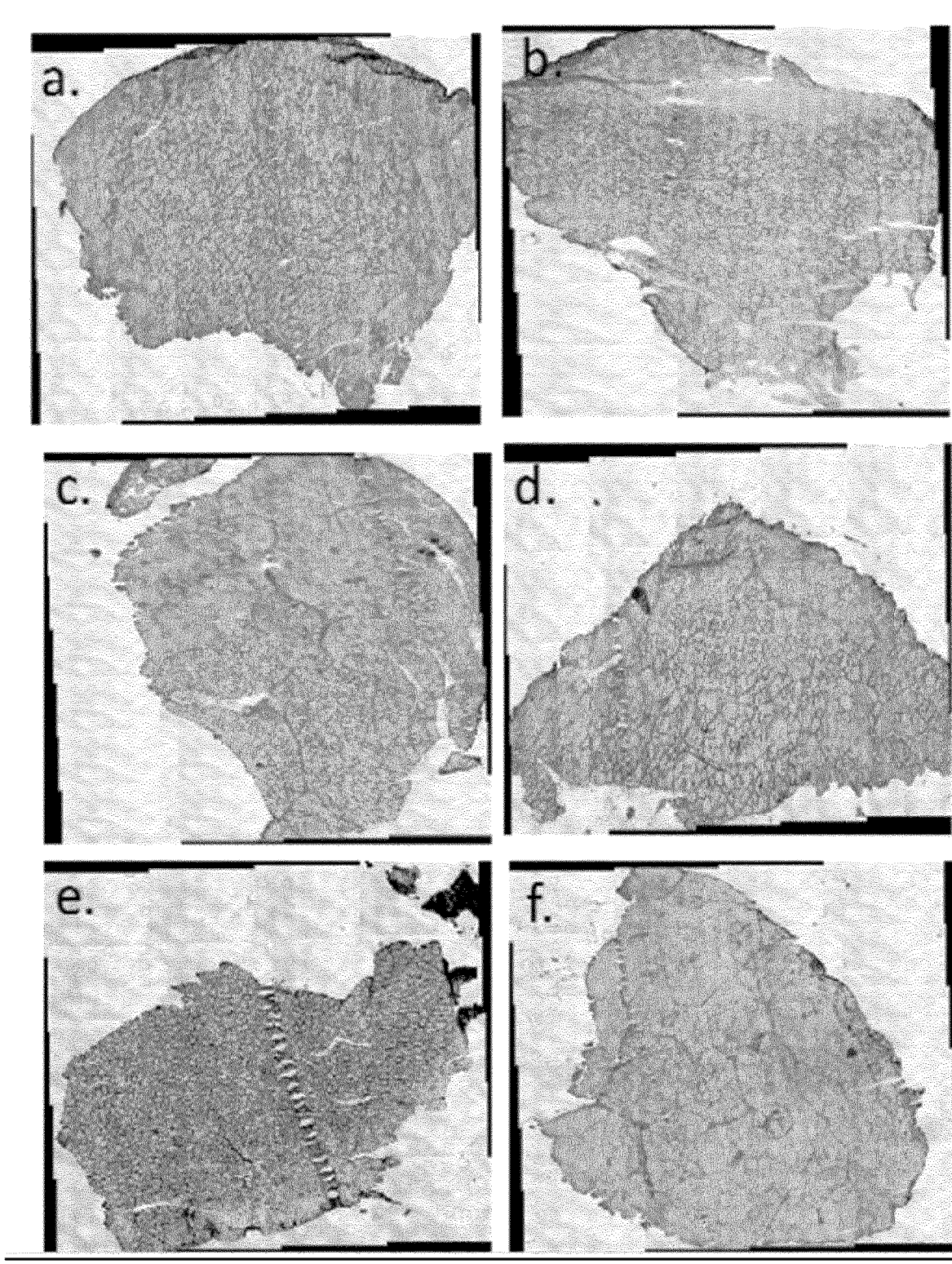

FIG. 7: Wide spread expression of mouse microdystrophin variant in mdx muscle injected with AAV2/9 vectors expressing the mMD1, mMD2, mMD3 and mMD4 microdystrophin variants.

The TA muscles of eight week old mdx mice were injected with $2 \times 10^{10}$ vg of rAAV 2/9-mMD1, mMD2, mMD3, and mMD4. TA muscles were recovered at eight weeks after injection and processed for cryosectioning. The sections were subjected to immune-peroxidase labeling with an antibody (Manex 1011C) against dystrophin. Low magnification bright-field micrographs are shown for AAV2/9-mMD1 (a), AAV2/9-mMD2 (b), AAV2/9-mMD3 (c), and AAV2/9-mMD4 (d). Control muscle from age-matched B57BL/10 (e) and mdx (f) were injected with saline only.

Figure 8:
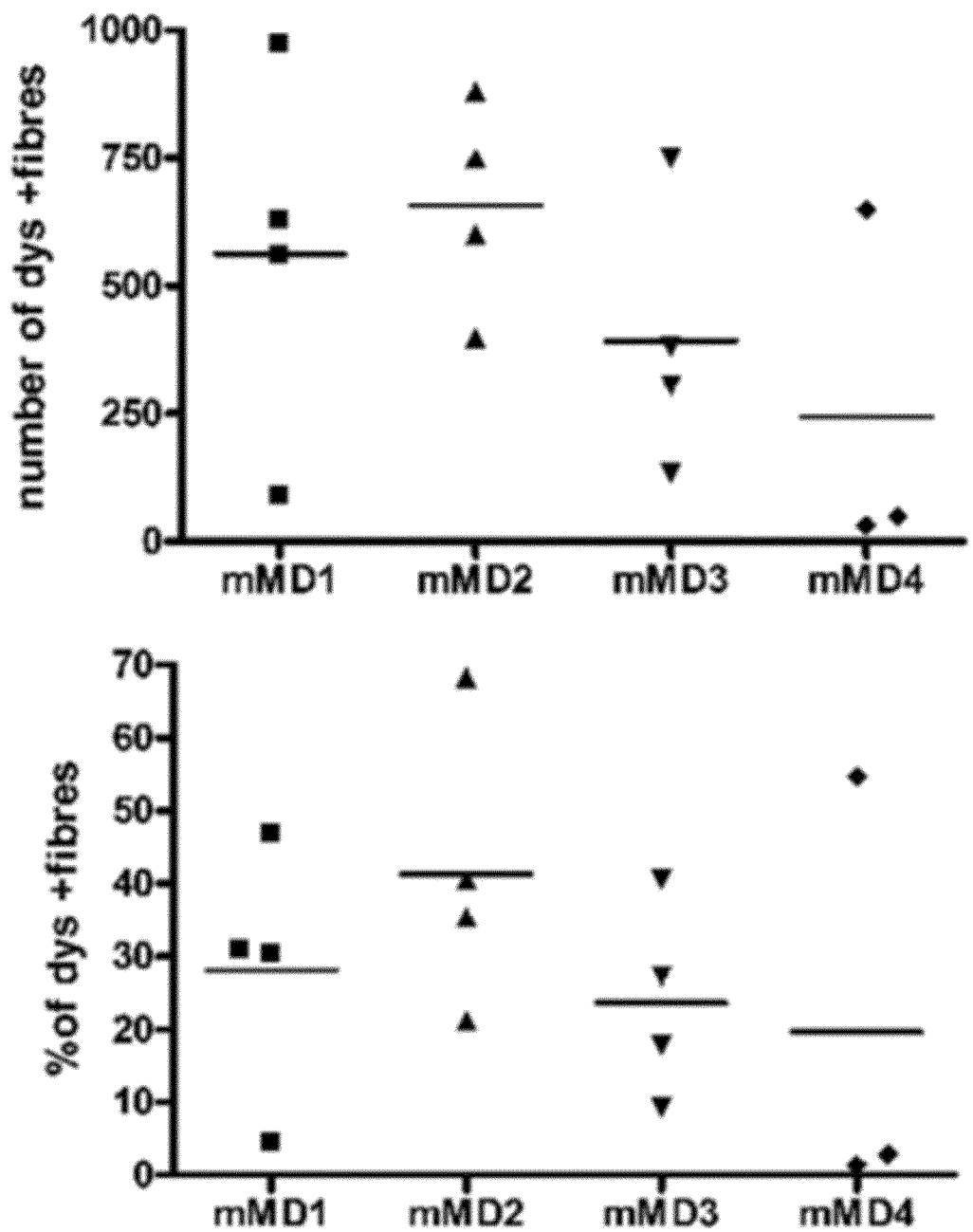

FIG. 8: Expression levels of mouse microdystrophin variant in young adult mdx muscle injected with AAV2/9 vectors expressing the mMD1, mMD2, mMD3 and mMD4. The TA muscles of 8 week old mdx mice were injected with $2 \times 10^{10}$ vg of AAV 2/9-mMD1, mMD2, mMD3, and mMD4. TA muscles were recovered at eight weeks post-injection and processed for cryosectioning. The sections were subjected to immunochemical labelling with an antibody (Manex 1011C) against dystrophin. Total number of microdystrophin-positive fibres was counted in whole TA muscle area. The percentage of dystrophin expression was calculated by dividing the number of dystrophin positive fibres by total number of fibres in TA muscles. (n=3 to 4, no significant difference compared among group analysed by one way ANOVA statistical analysis).

FIG. 9: (top) RT-PCR analysis of mMD4 mRNA levels in TA injected muscles of $mdx^{4cv}$ mice and Western blot analysis of mMD4. (bottom) Percentage of dystrophin positive fibers in mMD4 injected muscles (Bars indicate s.e.m).

FIGS. 10A-10D: Amelioration of the dystrophin deficient mice muscle phenotype.

10A) Dystrophin N-terminal domain (Manexl011B antibody), dystrophin C-terminus domain (Dys2 antibody), α-sarcoglycan, α-syntrophin and α-dystrobrevin immunostaining of mdx4cv TA muscles injected with saline, AAV2/9-µDys-CTL (mMD4) 10B) TA muscle weight of C57BL/6 control mice (C57, n=8) compared to TA muscles of mdx4cv mice (n=8) injected with saline (mdx4cv) or AAV2/9-µDys-CTL (mMD4) 10C) Specific maximal force (sP0) of TA muscles of C57BL/6 control mice (C57, n=8) compared to TA muscles of mdx4cv mice (n=8) injected with saline (mdx4cv) or AAV2/9-µDys-CTL (mMD4) 10D) Resistance to eccentric contractions. Absolute maximal force (P0) following lengthening contractions of TA muscles of C57BL/6 control mice (C57, n=8) compared to TA muscles of mdx4cv mice (n=8) injected with saline (mdx4cv) or AAV2/9-µDys-CTL (mMD4) (Bars indicate s.e.m, * indicates $p<0.05$; ** indicates $p<0.01$ compared to mdx4cv condition. Scale bar indicates 50 µm.)

Figure 11:
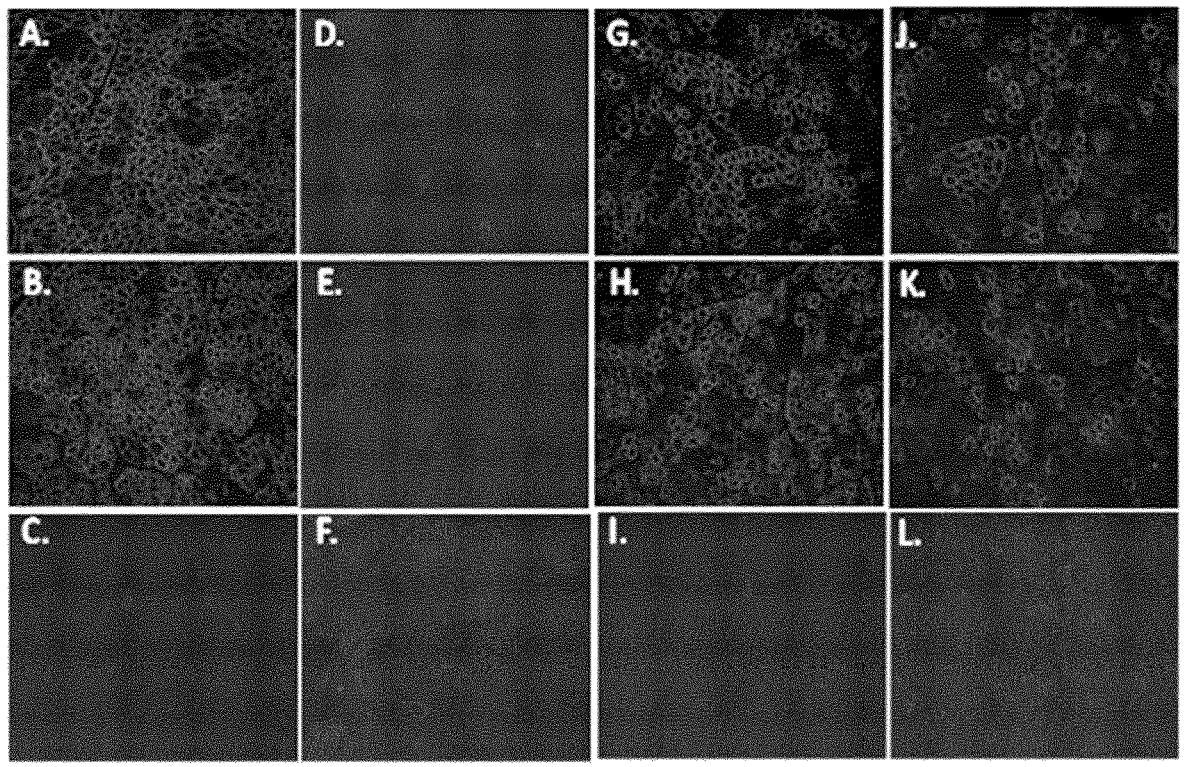

FIG. 11: Transduction of the CXMD TA muscle by AAV2/8-cMD1, cMD2, cMD3 and cMD4 at 2 month after injection. TA muscles of CXMD dogs were injected intramuscularly with $1 \times 10^{13}$ vg of AAV2/8-cMD1 (A, B, C) cMD2 (D, E, F), cMD3 (G, H, I) and cMD4 (J, K, L) and after 2 months tissues were harvested, cryosectioned and evaluated for microdystrophin expression by immunohistology using NCL-dys1 antibody (A, B, D, E, G, H, J, K) or NCL-Dys2 (C, F, I, L). Examples are shown from the apex (A, D, G, J) and base (B, C, E, F, H, I, K, L) regions of the muscles. The signal was visualized with an Alexa 568-conjugated anti-mouse IgG (1:1000). Dystrophin positive fibres in AAV2/8-microdys injected TA muscle was counted in approximately 3,000 numbers of total fibres. The percentage of dystrophin expression was calculated by dividing the number of dystrophin positive fibres by approximately 3,000 fibres in TA muscles.

Figure 12:
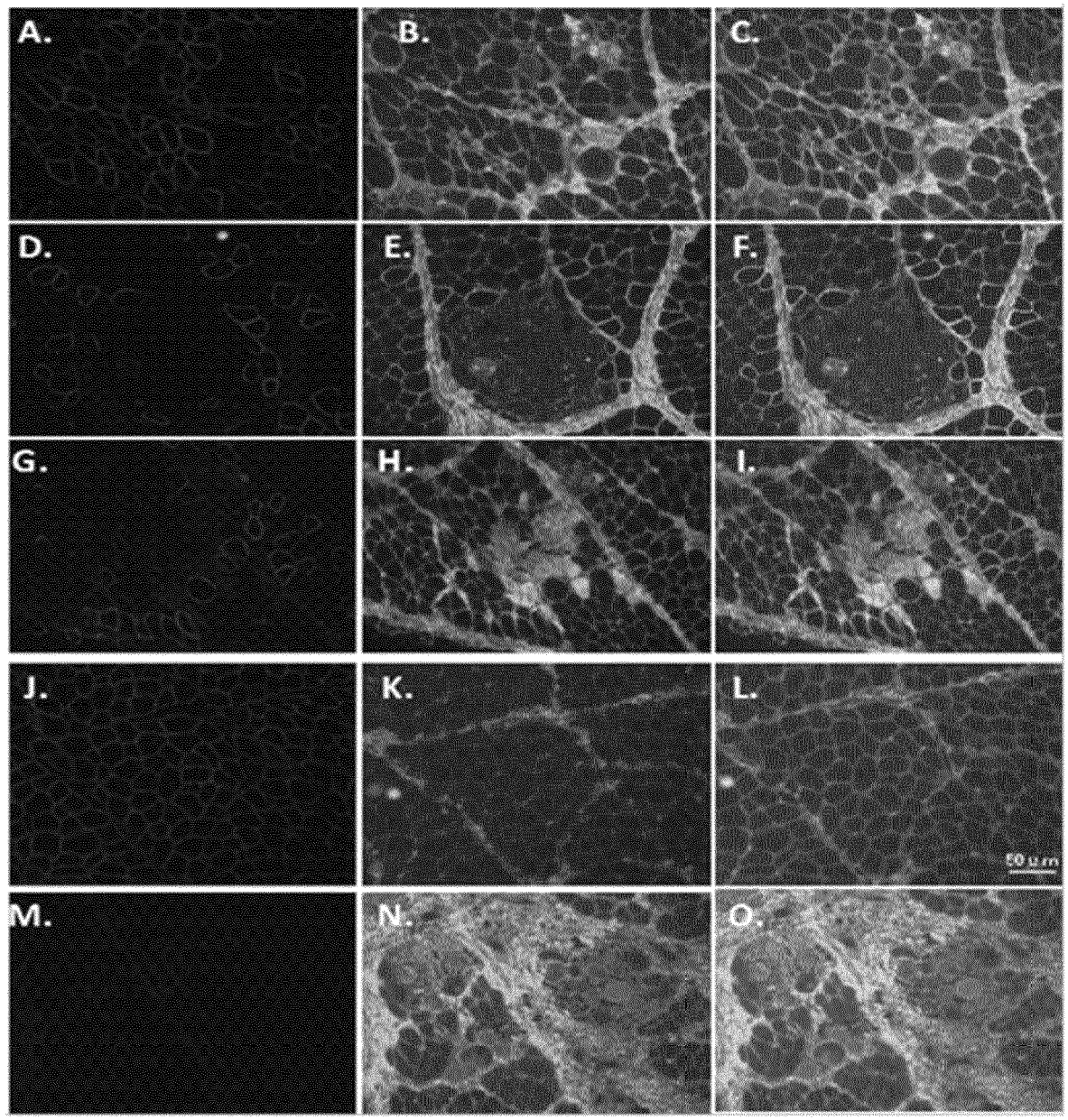

FIG. 12: Examination of muscle membrane integrity of TA muscle of CXMD dog following intramuscular injection of AAV2/8-microdystrophin. The TA muscles of CXMD dogs were injected with $1 \times 10^{13}$ vg of AAV2/8-cMD1 (A, B, C), cMD3 (D, E, F) and cMD4 (G, H, I). Age-matched WT (J, K, L) and CXMD (M, N, O) muscles were used as a positive/negative control. After 2 months tissues were harvested, cryosectioned and subjected to immunohistology of cryosections to examine membrane integrity. Sections were either stained for microdystrophin using NCL-dys1 antibody (A, D, G, J, M) or with Alexa 488-α-canine IgG secondary antibody (B, E, H, K, N). The dystrophin signal was visualized with an Alexa 568-conjugated anti-mouse IgG. Merge between microdystrophin and α-canine IgG (C, F, I, L, O). Magnification bar represents 50 µm.

Figure 13:
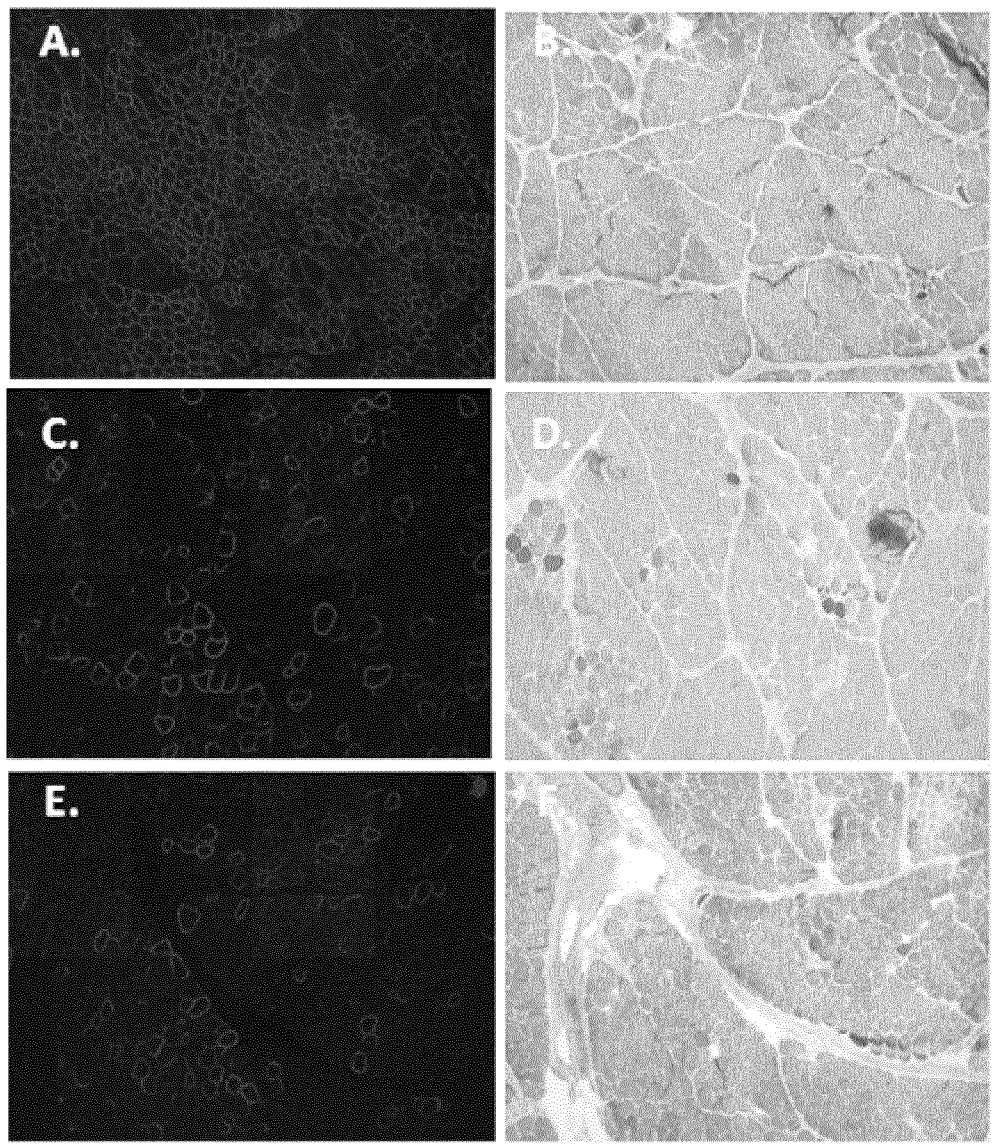

FIG. 13: Improvements in muscle pathology of CXMD following intramuscular injection of AAV2/8-microdystrophin. The TA muscles of CXMD dogs were injected with $1 \times 10^{13}$ vg of AAV2/8-cMD1 (A, B), cMD3 (C, D) and cMD4 (E, F). After 2 months tissues were harvested, cryosectioned and subjected to immunohistological analysis of cryosections to examine muscle restoration. Sections were either stained for microdystrophin using NCL-dys1 antibody (A, C, E) or with hematoxylin and eosin (B, D, F). The dystrophin signal was visualized with an Alexa 568-conjugated anti-mouse IgG.

Figure 14:
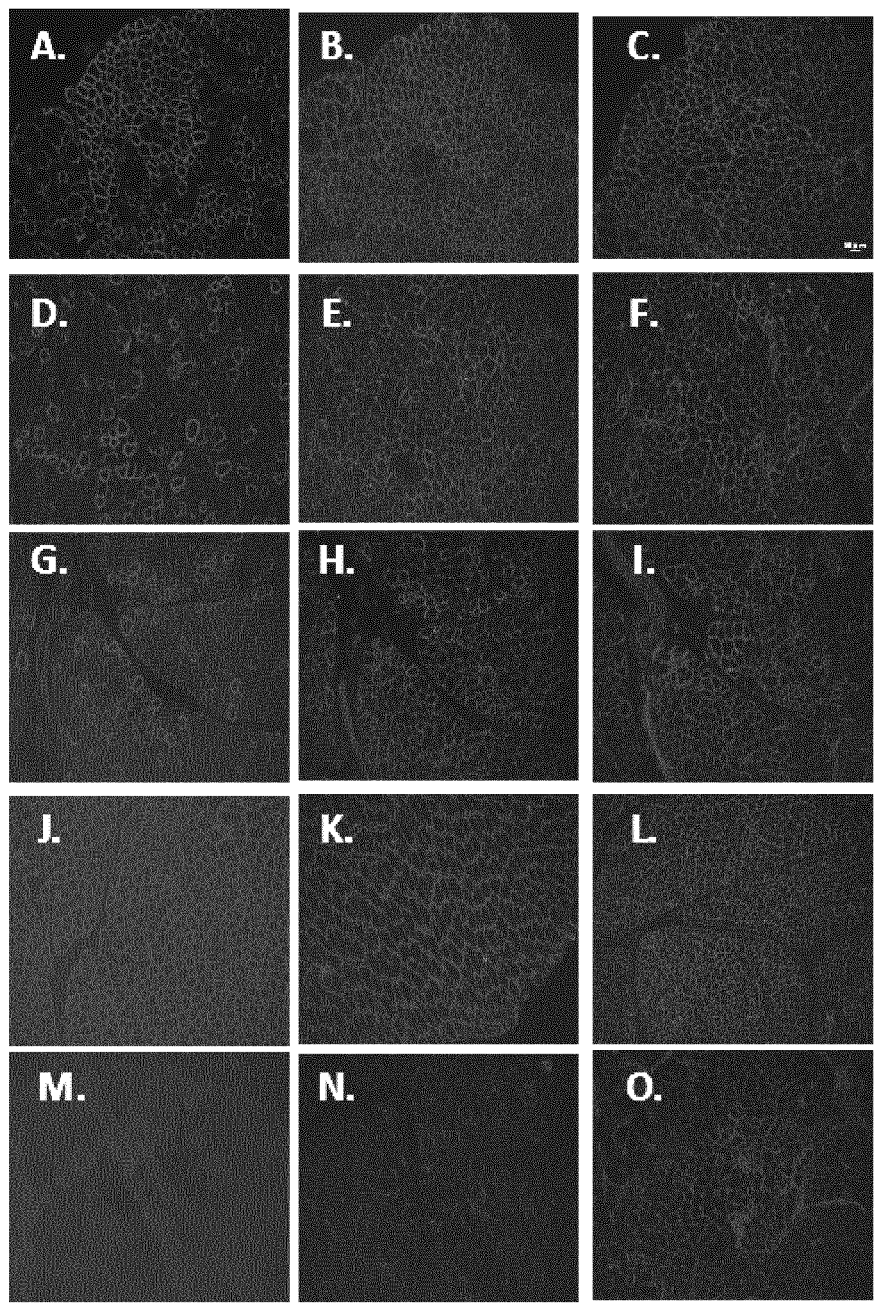

FIG. 14: Co-localisation of dystrophin and the DAP complex in TA muscles of cMD1, cMD2, cMD3 and cMD4 microdystrophin treated CXMD dog. TA muscles of CXMD dogs were injected with $1 \times 10^{13}$ vg of AAV2/8-cMD1(A, B, C) and cMD3 (D, E, F), cMD4 (G, H, I). Age-matched WT (J, K, L) and CXMD muscles (M, N, O) were used as a positive/negative control. After eight weeks tissues were harvested, cryosectioned and subjected to immunohistology of cryosections for Dys/dtn/syn staining to examine co-localisation of these proteins at the sarcolemma by immunohistology using NCL-dys1 antibody against dystrophin (A, D, G, J, M), α-dystrobrevin antibody (B, E, H, K, N) and α1-syntrophin antibody (C, F, I, L, O). The signal was visualized with an Alexa 568-conjugated anti-mouse IgG (1:1000) and fixed using DAPI mount medium. Magnification bar represents 50 µm.

DESIGN OF NOVEL MICRO-DYSTROPHIN (MD) CONSTRUCTS WITH C TERMINAL EXTENSIONS

1 Construction of CT Domains Containing Microdystrophins:

In order to construct CT domain containing microdystrophin variants, human (h), murine (m) and canine (c) specific and codon-optimised microdystrophin (MD) 1 cDNA format was used as the original template. This MD1 cDNA format was based on a widely used design which incorporates deletions of the coding sequence of rod domains 4-23 and the CT domain of the dystrophin. The MD1 encoded microdystrophin thus retains the N-terminal (NT) domain, hinge regions 1, 2 and 4 of spectrin repeats in rod domain, 1, 2, 3 and 24 of cystein-rich (CR) domain and three amino acids of exon 79 of dystrophin (see FIG. 1).

Figure 1:
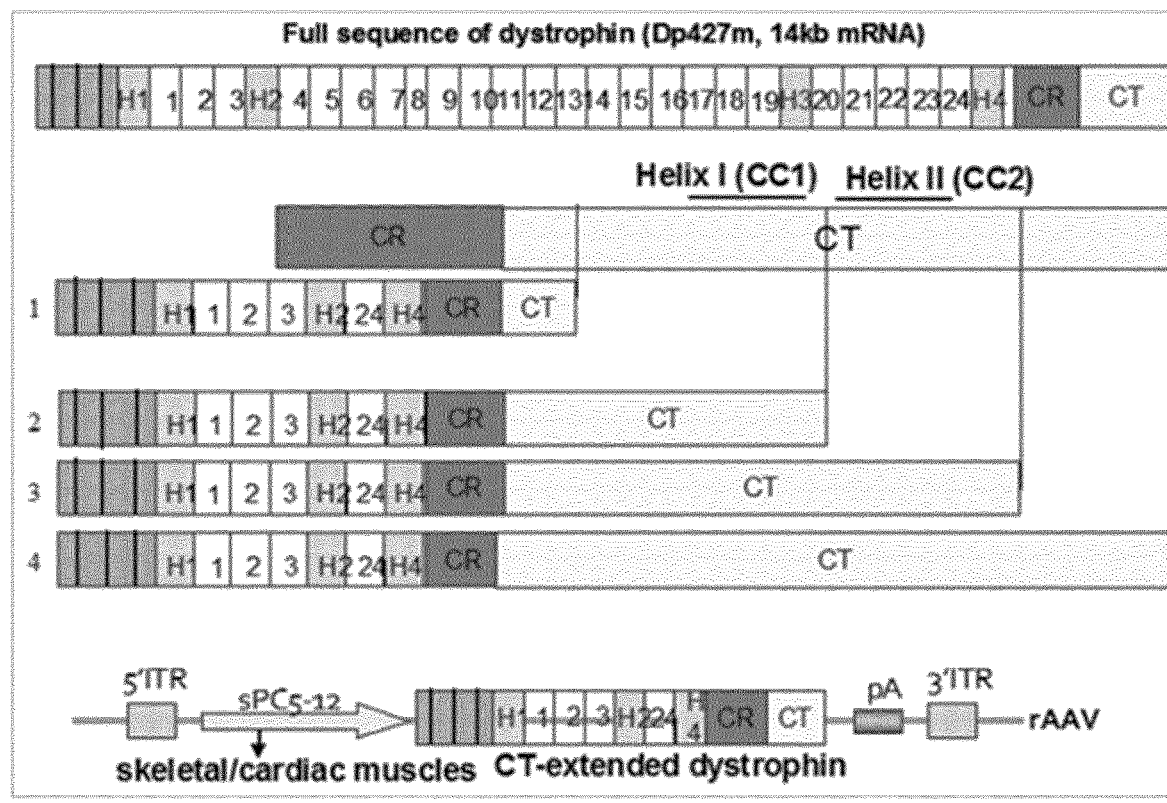
FIG. 1: Scheme of the full-length dystrophin, of various microdystrophins with variant CT domains extensions (1: MD1; 2: MD2; 3: MD3; 4: MD4) and of the expression construct.

Three CT domain containing microdystrophin cDNAs were designed and generated incorporating either part of, or the full CT domain sequence of dystrophin, and based on the originally synthesised MD1 codon optimised-microdystrophin (FIG. 1). The CT extensions were designed to include coiled coil region helix 1 (MD2), coiled-coil region helix 1 and 2 (MD3) or entire CT domain (MD4). The MD2 includes the Helix 1 of coiled coil motif in CT domain (exon 70 to exon 74) which interacts with syntrophin and dystrobrevin. The MD3 contains the Helix 1 and 2 of the coiled coil motif in the CT domain of dystrophin (exon 70 to exon 75) which incorporate the syntrophin and dystrobrevin binding sites. The MD4 includes the full CT domain (exons 70 to 79) of dystrophin. The four microdystrophin cDNA variants were designed for the mouse, canine and human dystrophin proteins, and designated mMD1-4, cMD1-4 and hMD1-4, respectively.

Of particular interest are the MD3 and MD4 proteins which size is predicted to be above the packaging capacity of the AAV vectors.

The corresponding amino acid sequences are as follows:
mMD3: SEQ ID NO: 1 of 1394 aa
mMD4: SEQ ID NO: 4 of 1473 aa
cMD3: SEQ ID NO: 7 of 1393 aa
cMD4: SEQ ID NO: 10 of 1472 aa
hMD3: SEQ ID NO: 13 of 1392 aa
hMD4: SEQ ID NO: 16 of 1471 aa 2 Optimization of the Corresponding mRNA Sequences:

Codon usage of each microdystrophin cDNA was codon-optimised by increasing GC content in the sequence to promote RNA stability based on transfer RNA frequencies in human. Although murine or canine cDNA of microdystrophins were optimised based on human sequences, codon usage and transfer RNA frequencies shows similarity among the vertebrates (Hastings, Emerson 1983). Optimal consensus Kozak sequence (GCCACCATGC) including ATG start codon was incorporated to improve the initiation of the translation. Additionally 5'- and 3'-untranslated regions of the dystrophin cDNA were removed to decrease the size of the microdystrophin cassette flanked by ITR.

The corresponding optimized cDNA sequences are as follows:
mMD3: SEQ ID NO: 2 of 4191 bp
mMD4: SEQ ID NO: 5 of 4428 bp
cMD3: SEQ ID NO: 8 of 4188 bp
cMD4: SEQ ID NO: 11 of 4425 bp
hMD3: SEQ ID NO: 14 of 4185 bp
hMD4: SEQ ID NO: 17 of 4422 bp 3 Construction of the New AAV-MD Plasmids:

In order to be able to produce AAV vectors in due course, the various MDs were incorporated into an AAV vector plasmid under control of the muscle specific Spc5-12 promoter and incorporating the SV40 poly-adenylation site (FIG. 1).

Figure 2:
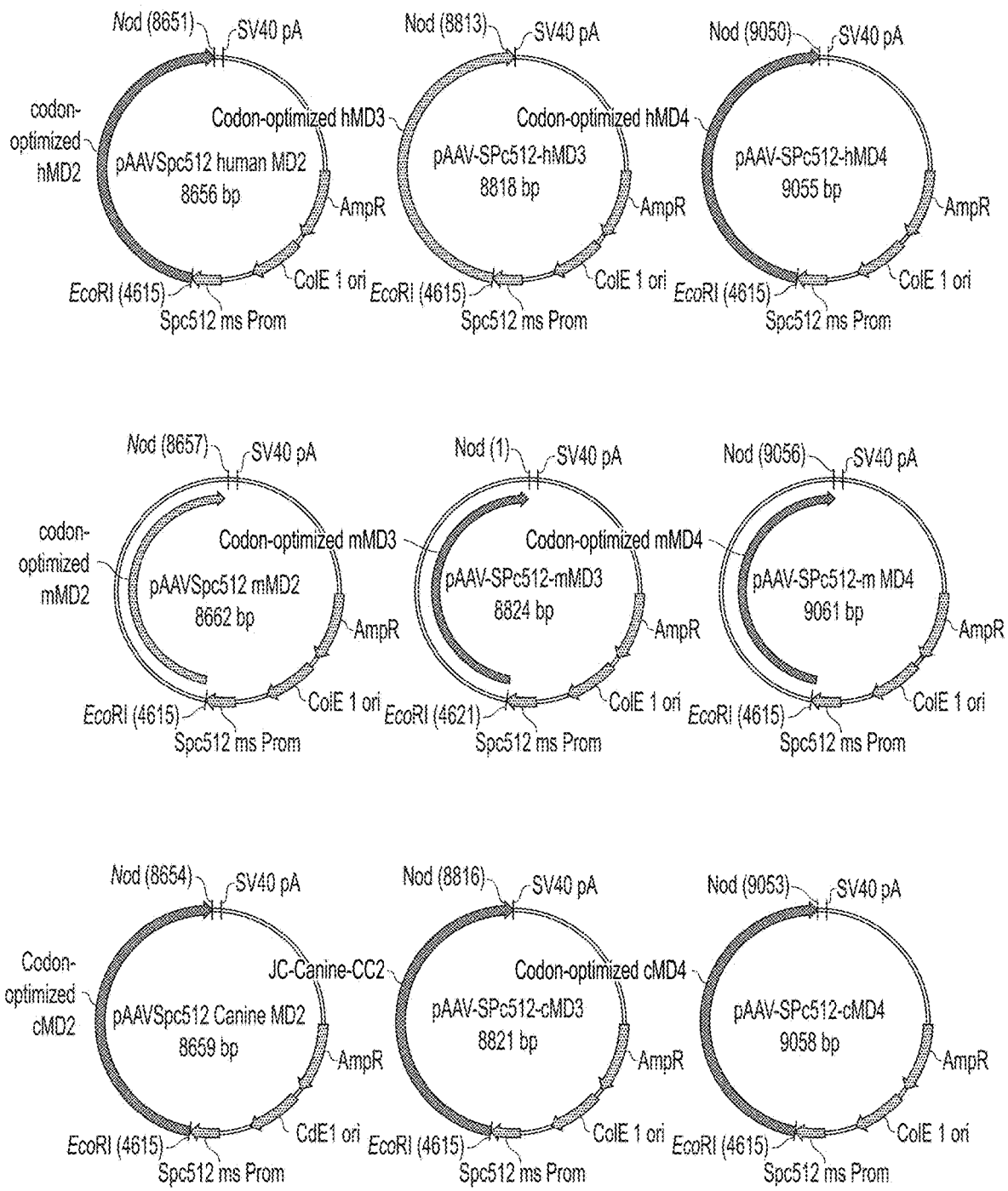
FIG. 2: Diagram of AAV ITR based MD2, MD3, and MD4 vectors plasmids.

Construction of MD3 and MD4 microdystrophin plasmids was accomplished by AvrII/NotI mediated subcloning, using the pAAVSpc512-MD1 plasmid (disclosed e.g. in Koo et al., J Gene Med, 2011. 13(9): 497-506) as the original template (FIG. 2).

Human (h), murine (m), and canine (c) species-specific MD1, MD2, MD3 and mMD4 cDNA was inserted between Spc5-12 muscle specific promoter and SV40 polyadenylation signal. All microdystrophin codon was optimised and this cassette was flanked by two inverted terminal repeats (ITRs) of AAV serotype 2 at the 5' and 3' end of the microdystrophin. To validate species homologues (m; murine, h; human, c; canine), extension of the C-terminal domain of dystrophin (MD1, MD2, MD3, and MD4) and 5' or 3' ITR presence and restriction endonuclease mapping analysis of cloned microdystrophin variants were performed with several enzymes.

As shown on FIG. 2, the insert in each plasmid comprises:
the 5' ITR sequences of the AAV vector (1-145 of SEQ ID NO: 3)
the Spc5.12 promoter of 334 bp (253 to 586 of SEQ ID NO: 3)
the coding sequence for MD3 and MD4 having a size comprised between 4185 bp and 4428 bp;
the polyadenylation signal (polyA) of SV40 of 240 bp (nucleotides 4852 to 5091 of SEQ ID NO: 3)
the 3' ITR sequences of the AAV vector (nucleotides 5138-5283 of SEQ ID NO: 3).

The Inverted Terminal Repeat (ITR) sequences of 145 bases each have the following sequences:

```
                                          (SEQ ID NO: 19)
5'aggaacccct agtgatggag ttggccactc cctctctgcg cgctcgctcg ctcactgagg ccgcccgggc aaagcccggg cgtcgggcga cctttggtcg cccggcctca gtgagcgagc gagcgcgcag agagggagtg gccaa-3'
```

The Spc512 muscle synthetic promoter of 334 bp has the following sequence:

```
                                          (SEQ ID NO: 20)
ggccgtccgc cctcggcacc atcctcacga cacccaaata tggcgacggg tgaggaatgg tggggagtta tttttagagc ggtgaggaag gtgggcaggc agcaggtgtt ggcgctctaa aaataactcc cgggagttat ttttagagcg gaggaatggt ggacacccaa atatggcgac ggttcctcac ccgtcgccat atttgggtgt ccgccctcgg ccggggccgc attcctgggg gccgggcggt gctcccgccc gcctcgataa aaggctccgg ggccggcggc ggcccacgag ctacccggag gagcgggagg cgccaagctc taga
```

The 240 bp SV40polyA signal sequence has the following sequences:

```
                                          (SEQ ID NO: 21)
agacatgata agatacattg atgagtttgg acaaaccaca actagaatgc agtgaaaaaaatgctttatt tgtgaaattt gtgatgctat tgctttattt gtaaccatta taagctgcaa taaacaagtt aacaacaaca attgcattca ttttatgttt caggttcagg gggagatgtg ggaggttttt taaagcaagt aaaacctcta caaatgtggt aaaatccgat aaggactaga
```

Other possible sequences are:

(SEQ ID NO: 22)
```
cagacatgat aagatacatt gatgagtttg gacaaaccac aactagaatg cagtgaaaaa aatgctttat ttgtgaaatt tgtgatgcta ttgctttatt tgtaaccatt ataagctgca ataaacaagt taacaacaac aattgcattc attttatgtt tcaggttcag ggggagatgt gggaggtttt ttaaagcaag taaaacctct acaaatgtgg ta
```
or (SEQ ID NO: 23)
```
atctagataa ctgatcataa tcagccatac cacatttgta gaggttttac ttgctttaaa aaacctccca cacctccccc tgaacctgaa acataaaatg aatgcaattg ttgttgttaa cttgtttatt gcagcttata atggttacaa ataaagcaat agcatcacaa atttcacaaa taaagcattt ttttcactgc attctagttg tggtttgtcc aaactcatca atgtatctta
```
or (SEQ ID NO: 24)
```
agacatgata agatacattg atgagtttgg acaaaccaca actagaatgc agtgaaaaaa atgctttatt tgtgaaattt gtgatgctat tgctttattt gtaaccatta taagctgcaa taaacaagtt aacaacaaca attgcattca ttttatgttt caggttcagg gggaggtggg gaggtttttt aaagcaagta aaacctctac aaatgtggta tggctgatta tgatccggct gcctcgcgcg tttcggtgat gacggtgaaa acctctgaca catgcagctc ccggagacgg tcacagcttg tctgtaagcg gatgccggga gcagacaagc ccgtcagggc gcgtcagcgg gtgttggcgg gtgtcggggc gcagccatga ccggtcgac
```

The sequences corresponding to said inserts (5'ITR to 3-ITR) are as follows:
sequence SEQ ID NO: 3 (mMD3): 5283 bp
sequence SEQ ID NO: 6 (mMD4): 5520 bp
sequence SEQ ID NO: 9 (cMD3): 5280 bp
sequence SEQ ID NO: 12 (cMD4): 5517 bp
sequence SEQ ID NO: 15 (hMD3): 5277 bp
sequence SEQ ID NO: 18 (hMD4): 5514 bp 4 Validation of the New AAV-MD Plasmids:

Transcriptional Activity of the MD Plasmid Vectors by Transfection into Mouse C2C12 Myoblast Cultures:

To assess the functional activity, plasmids expressing CT-extended microdystrophin variants were transfected into primary C2C12 myoblast cells. C2C12 myoblasts were originally isolated from the skeletal muscle of C57BL/10 mouse. Approximately $7.5 \times 10^5$ C2C12 myoblast cells were cultured in 40 mm dishes and transfected 3 days later with pAAV-mMD1, -mMD2, -mMD3, and -mMD4 microdystrophin plasmids using Lipofectamine 2000. Transfection was carried out in serum free conditions. 4 hrs after transfection, transfection mixture was replaced with DMEM medium containing 10% FCS and incubated at 37° C., 8% $CO_2$.

Figure 3:
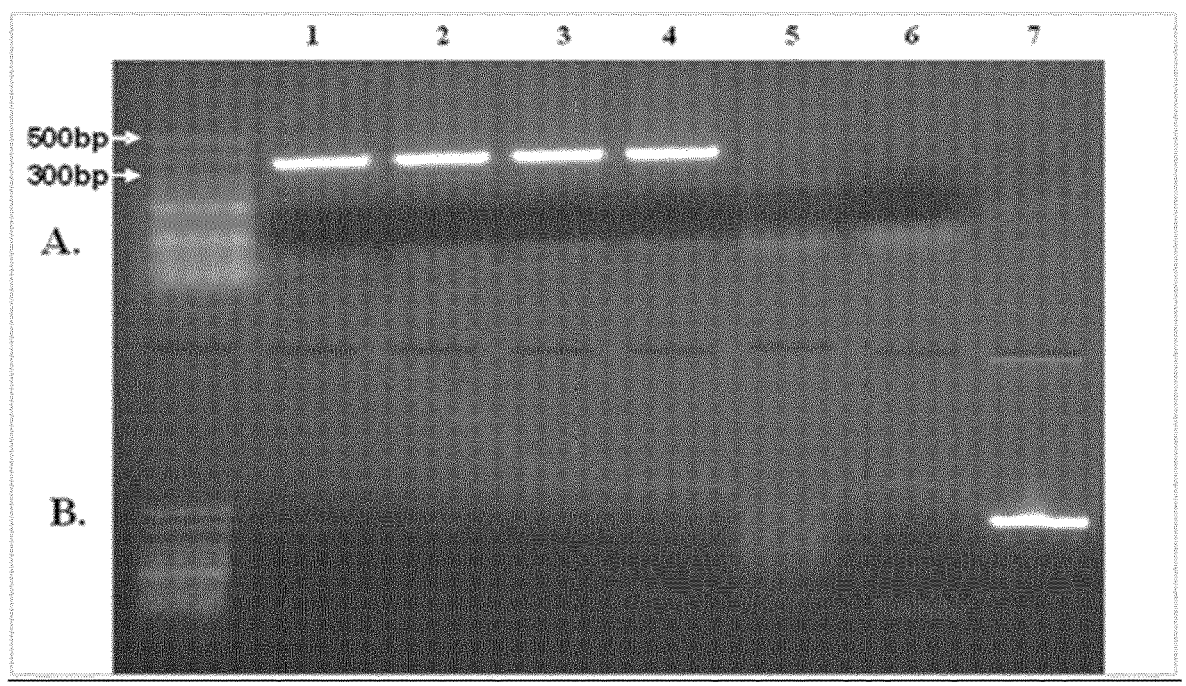
FIG. 3: RT-PCR analysis of RNA from murine myoblast C2C12 cells transfected with mouse microdystrophin expression plasmids.

After 48 h, when the cells were fully differentiated and fused each other to form myotubes, RNA was extracted from the cultures. The presence of dystrophin mRNA transcripts of pAAV-mMD3, and -mMD4 was evaluated by RT-PCR. Codon-optimised cDNA specific primer sets were as follows (5'-3'): TGGAGCAGGAGCACAACAA (forward; SEQ ID NO: 25), ATCTCGGGCTTGTTGTTGG (Reverse; SEQ ID NO: 26). Approximately 346 bp RT-PCR products were amplified in all microdystrophin variants, but not in negative control cultures (FIG. 3).

Conclusion:

This in vitro data demonstrates that all microdystrophin cDNA genes were able to be functionally transcribed in the muscle cells under the control of SPc5-12 promoter. No cDNA from RNA (Reverse transcriptase oblated reactions) was observed by PCR, indicating that amplified cDNA was derived only by cellular RNA in microdystrophin transfected cells.

Expression of MD Variants Following Electroporation of Plasmid Vectors into TA Muscles of Mdx Mice:

To analyse the efficiency of microdystrophin protein expression in muscle, these plasmids were tested in vivo by electrotransfer into tibialis anterior (TA) muscles of mdx mice. 5 month old male mdx were injected with 10 units of bovine hyaluronidase (25 ml at 0.4 units/ml). Two hours later, TA muscles were injected with each 25 mg of pAAV-mMD3, and -mMD4 microdystrophin plasmids in 25 ml of sterile injectable saline solution. Control C57BL/10 and mdx mice were injected with 25 ml of saline solution only. Electrode jelly was placed on the electrode plates to increase the contact area with the skin of mouse. Electrical field was then applied to the injected TA muscle using external electrodes at 175 V/cm in 20 ms square wave pulses at 1 Hz. During injection and electrotransfer procedure, all mice were anaesthetised with 2-4% isoflurane.

At 8 days postinjection, TA muscles were recovered and subjected to immunohistology for the dystrophin staining. Electrotransfer of microdystrophins achieved positive staining of microdystrophin at the sarcolemmal membrane of mdx mice, successfully. Positive dystrophin fibres were counted in microdystrophin electroporated muscle of mdx mice (FIG. 4). Approximately, 320, 380, 260 and 220 of the dystrophin positive fibres were counted in mMD1, mMD2, mMD3, and mMD4 microdystrophin plasmid electroporated TA muscle section of mdx mice, respectively. Reverted/regenerated myofibres, which were labelled with dystrophin antibodies (6D3), was not counted as microdystrophin positive fibres. Statistical analysis by one way ANOVA showed that no significant difference was observed between mMD1, mMD2, mMD3 and mMD4 plasmid transduced muscle of mdx mice (n=4).

Conclusion:

This in vivo result demonstrated that all microdystrophin plasmid could achieve successful dystrophin expression at the sarcolemmal membrane with similar functionality of transduction efficiency in skeletal muscle.

5 Evaluation of AAV 2/9 Vectors Expressing the New MD Variants in Mdx Mouse:

Production and Characterization of the AAV 2/9 Vectors:

To produce AAV vectors, dual or triple-plasmid transfection into 293T cells is required, followed by virus harvesting and purification. In order to optimise the yield of AAV vectors, various transfection protocols were evaluated based upon exposure of cells to $CaPO_4$ precipitates of plasmid DNA formed at different pH values. Substantial transfection efficiencies in 293T cells were observed with an eGFP plasmids vector and using $CaPO_4$ precipitation to optimise the transfection efficiencies in pH 7.0, pH 7.05 and pH 7.1 HEPES buffer. After 2 days, eGFP expression in live cells was observed under the epifluorescence microscope. In pH7.05 HEPES buffer mediated-eGFP plasmid transfected cells, it showed highest transfection efficiencies (data not shown).

For AAV vector production, 293T cells in 1 roller bottle (1700 cm$^2$) were transfected with vector plasmids, pAAVITR-mMD1, mMD2, mMD3, and mMD4 along with pAdDF6 and pAAVhelpercap9 plasmids using CaPO$_4$ precipitation in optimised pH 7.05 HEPES buffer. After transfection of DNA, AAV was harvested and purified, and AAV yields were determined by dot-blot hybridisation (FIG. 5). Routinely AAV vector concentrations were between $1 \times 10^{12}$ and $5 \times 10^{12}$ vector genomes per ml. Virus vectors concentration of AAV2/9-mMD1, mMD2, mMD3 and mMD4 were $3.7 \times 10^{12}$, $3.1 \times 10^{12}$, and $1.6 \times 10^{12}$, $2.6 \times 10^{12}$ vector genome per ml, respectively.

Expression of MD Variants at the Sarcolemmal Membrane Following Intramuscular Delivery of AAV2/9-MD into TA Muscles of Mdx Mice:

To examine the level of the dystrophin expression at the sarcolemma of the young adult mdx mouse, the TA muscle of 2 month old mdx mice were injected with $2 \times 10^{10}$ vg of AAV 2/9-mMD1, mMD2, mMD3 and mMD4 in 25 ml of sterile injectable saline solution. After 8 weeks, TA muscles were recovered, cryosectioned and subjected to immunohistochemical labelling with an Manex 1011C antibody against dystrophin. Microdystrophin proteins were stained at the sarcolemmal membrane of AAV2/9-mMD1, -mMD2, -mMD3 and -mMD4 injected mdx mice, successfully (FIGS. 6 and 7).

To verify the level of dytrophin expression at the sarcolemma, positive fibres in AAV2/9-mMD1, mMD2, mMD3, and mMD4 injected TA muscle were counted in immunohistochemically labelled whole TA muscle areas. Approximately 560, 660, 390 and 240 of mMD1, mMD2, mMD3 and mMD4 microdystrophin positive fibres were counted in AAV2/9 injected whole TA muscles, respectively. The percentage of dystrophin expression was calculated by dividing the number of dystrophin positive fibres by total number of fibres in TA muscles. Approximately 28%, 41%, 24% and 20% of mMD1, mMD2, mMD3 and mMD4 microdystrophin positive fibres were observed in AAV2/9 injected whole TA muscles, respectively (FIG. 8). Statistical analysis by one way ANOVA showed that no significant difference of dystrophin expression level was observed between mMD1, mMD2, mMD3, and mMD4 constructs treated muscle of mdx mice (n=4).

Conclusion:

These in vivo data show that:

Viral particles are produced at acceptable levels;

The corresponding microdystrophins are produced at acceptable levels.

6 Evaluation of AAV 2/9 Vectors Expressing the New MD Variants in mdx4cv Mouse:

Methods:

In Vivo Gene Transfer.

All mouse procedures were done according to protocol approved by the Committee on Animal Resources at the Centre d' Experimentation Fonctionnelle of Pitié-Salpetrière animal facility and under appropriate biological containment. Adeno-associated virus (AAV2/9) vectors were produced using three-plasmid constructs protocol. For microdystrophin (µDys) expression, 2-month-old mdx$^{4cv}$ mice were injected into the Tibialis anterior (TA) with 50 µl of AAV2/9-µDys (mMD4) vectors containing $2.5 \times 10^9$ viral genomes (vg). For each mouse, the left TA muscle was injected with AAV and the contralateral muscle was injected with vehicle alone (PBS). Animals were sacrificed 2 months after AAV-tDys injection and muscles were collected, snap-frozen in liquid nitrogen-cooled isopentane and stored at −80° C.

RNA Extraction and RT-PCR Analysis.

RNAs were isolated using TRIzol reagent (Invitrogen) according to the manufacturer's protocol. 1 µg of RNA was reverse transcribed using M-MLV first strand synthesis system according to the manufacturer's instructions (Invitrogen) in a total of 20 µl. One µl of cDNA preparation was subsequently used in a semi-quantitative PCR analysis according to standard protocol (ReddyMix, Thermo Scientific). PCR amplification was carried out for 20-35 cycles within the linear range of amplification for each gene. PCR products were resolved on 1% agarose or 5% non-denaturing polyacrylamide (for splicing) gels, BET stained and quantified with ImageJ software. To quantify mRNA expression, Real-time PCR was performed using a Lightcycler 480 (Roche). Reactions were performed with SYBR Green kit (Roche) according to the manufacturer's instructions. PCR cycles were a 15 min denaturation step followed by 50 cycles with a 94° C. denaturation for 15 sec, 58° C. annealing for 20 sec, and 72° C. extension for 20 sec. Mouse Rrlp0 mRNA or zebrafish elongation factor alpha (elfa) mRNA were used as standard. Data were analysed with the Lightcycler 480 analysis software.

Immunohistochemistry and Histology.

Hematoxylin and eosin (HE) staining was used to examine the overall muscle morphology of 10 tm TA muscle sections. For immunohistochemistry, muscle cryo-sections were stained using Mouse on Mouse (M.O.M) kit (Vector Labs). Primary antibodies were incubated overnight at 4° C. followed by 3 washes with PBS-0.1% tween, and incubated with goat anti-mouse or goat anti-rabbit secondary antibodies Alexa 488, Alexa 555 or Alexa 647 (Life Technologies). Antibodies against dystrophin (Manex1011B, 1:100, mouse monoclonal, gift from Dr. Glenn Morris; Dys1 and Dys2, 1:100, mouse monoclonal, Novocastra; MANDRA1, 1:1000, Mouse monoclonal, Sigma-Aldrich), α-syntrophin (rabbit polyclonal, 1:200, Abcam), α-dystrobrevin (mouse monoclonal, 1:200, BD Biosciences); anti-MHCIIa (SC71, 1:3, mouse monoclonal IgG; Hybridoma DSHB), anti-MHCIIX (6H1-mouse monoclonal IgM; Hybridoma DHSB), laminin (1:300, rabbit polyclonal, Chemicon) were used.

Electron Microscopy.

TA muscles were dissected, cut into small pieces and immediately fixed in 2% glutaraldehyde, 2% PFA, 0.1M phosphate buffer. After abundant washes and 2% OsO4 post fixation, samples were dehydrated at 40 in graded acetone including a 1% uranyl acetate in 70° acetone step, and were finally embedded in Epon resin. Thin (70 nm) sections were stained with uranyl acetate and lead citrate, observed using a Philips CM120 electron microscope (Philips Electronics NV) and photographed with a digital SIS Morada camera.

In Situ Force Measurement.

The isometric contractile properties of TA muscle were studied in situ as previously described (Mouisel, E. et al. Neurosci. Res., 2006. 55: 389-396). Mice were anesthetized with pentobarbital (60 mg/kg intraperitoneally). The knee and foot were fixed with clamps and pins. The distal tendon of the TA muscle was attached to a lever arm of a servo-moteur system (305B, Dual-Mode Lever). Data were recorded and analysed on a microcomputer using PowerLab system (4SP, ADInstruments) and software (Chart 4, ADInstruments). The sciatic nerve (proximally crushed) was stimulated by a bipolar silver electrode using a supramaximal (10-V) square wave pulse of 0.1 ms duration. All contractions were made at an initial length L0 (length at which maximal tension was first obtained during tetanic contractions). Absolute maximal isometric tetanic force was measured during isometric contractions in response to electrical stimulation (frequency of 25 to 150 Hz, train of stimulation of 500 ms). Maximal specific isometric force was calculated by dividing absolute maximal isometric force by muscle weight.

Resistance to eccentric (lengthening) contractions of TA muscles was then evaluated by measuring the force drop following eccentric contractions (Koo et al., 2011). A maximal isometric contraction of the TA muscle was initiated during the first 500 msec. Then, muscle lengthening (1.1 mm, 10% L0) at a velocity of 0.5 mm/sec (about 0.5 L0/sec) was imposed during the last 200 msec. Nine lengthening contractions of the TA muscles were performed, each separated by a 60-sec rest period. Maximal isometric force was measured after each eccentric contraction and expressed as a percentage of the initial maximal isometric force.

Results:

The test whether the C-ter domain modulates dystrophin activity, the ability of the micro-dystrophin construct µDys-CTL encoding the murine MD4 (mMD4) in restoring muscle function of dystrophin deficient (mdx$^{4cv}$, Charles River Laboratories; Decrouy et al., Gen Ther, 1997. 4(5): 401-8) mice has been tested. Adeno-associated virus (AAV2/9) vectors expressing µDys-CTL (also noted mMD4) were injected locally in Tibialis Anterior (TA) muscles of mdx$^4$cv mice. Muscles transduced with said construct expressed satisfying levels of µDys transcripts (FIG. 9 top) as well as numbers of µDys-positive fibers (FIG. 9 bottom).

They also showed expected localization of µDys at the sarcolemma (FIG. 10a). As described by others for functional µDys constructs mdx$^4$cv muscles injected with µDys-CTL (mMD4) showed a significant reduction in TA muscle weight (FIG. 10b) and a significant improvement of the specific maximal force (FIG. 10c) when compared to saline-injected contralateral muscles. The ability of µDys to protect skeletal muscle from injury by testing resistance to eccentric contractions was then determined. A partial but significant improvement of resistance to eccentric contraction was observed in µDys-CTL (mMD4) injected muscles compared to saline-injected muscles ($p<0.05$) (FIG. 10d).

Conclusion:

These in vivo data show that the microdystrophins are functional since they are able to ameliorate dystrophin-deficient mice muscle phenotype.

I-7 Evaluation of AAV 2/8 Vectors Expressing the New MD Variants in the cxmd Canine Model:

Similar experiments have been performed in the Beagle-based CXMD model with AAV 2/8 vectors expressing the new MD variants.

Production and Characterization of the AAV 2/8 Vectors:

AAV2/8-cMD1, cMD2, cMD3 and cMD4 vectors were produced by CaPO4 transfection of vector plasmids with pAAVITR-cMD1, cMD2, cMD3, and cMD4 along with pAdDF6 and pAAVhelpercap8 plasmids into 392T cells. AAV vectors were harvested and purified by CsCl gradient centrifugation. The viral titres were determined by quantitative PCR using the codon-optimised microdystrophin specific primer; ccaacaaagtgccctactacatc (forward) and ggttgt-gctggtccagggcgt (reverse). The viral concentration of the rAAV2/8-cMD1, cMD2, cMD3 and cMD4 were $4.0\times10^{13}$ vg/ml, $1.4\times10^{13}$ vg/ml, $1.8\times10^{13}$ vg/ml and $1.5\times10^{13}$ vg/ml, respectively.

Transduction of the TA Muscle of CXMD Dog by AAV2/8-Vectors at 2 Month after Injection:

The transduction efficacy of the cDM1 was still efficient at 2 month after injection. Approximately 83.6% dystrophin fibres were positive in TA muscles at eight weeks after injection of AAV2/8-mMD1. In AAV2/8-cMD3 and cMD4 injected TA muscle, approximately 36.5% and 26.5% of the expression of dystrophin was observed at eight weeks after injection (FIG. 11).

To verify the microdystrophin variants, microdystrophin was detected using NCL-Dys 2 antibody which detects the extreme C-terminal domain (amino acids 3669-3685) of the dystrophin. As expected, only cMD4 microdystrophin was detected (FIG. 11)

Examination of Muscle Membrane Integrity of TA Muscle of CXMD Dog Following Intramuscular Injection of AAV2/8-Microdystrophin.

It was also investigated whether microdystrophin expression can restore membrane integrity. Lack of the dystrophin in muscle invariably leads to failure of muscle integrity as assessed by the presence of 'leaky' fibres. Damaged muscle membrane can be indicated by staining with extracellulary applied labelled endogenous extracellular proteins such as albumin, immunoglobulin G (IgG) and IgM (Blake, Weir et al. 2002). Membrane integrity of cMD1, cMD3 and cMD4 positive fibres was examined using an anti-canine IgG immunostaining. Membrane damaged fibres shows cytoplasmic IgG staining due to more permeable muscle membrane. In cMD1, cMD3 and cMD4 transduced TA muscle of CXMD dogs, microdystrophin positive fibres did not render any cytoplasmic IgG staining which indicates that integrity of sarcolemmal membrane was improved by microdystrophin expression (FIG. 12).

Improvements in Muscle Pathology of CXMD Following Intramuscular Injection of AAV2/8-Microdystrophin It was examined whether microdystrophin expression in muscle can prevent or halt the muscle damage in CXMD dogs. Central nucleation is one of the markers of myofibre regeneration in dystrophin muscles. At eight weeks after intramuscular injection of $1\times10^{13}$ vg of AAV2/8-cMD1, cMD3 and cMD4 into the muscle of CXMD dogs, TA muscles were recovered and subjected to immunohistology for the H&E staining which can stain nuclei and cytoplasm. Central nucleation in muscle fibres was not evident in dystrophin positive muscle areas of cMD1, cDM3 and cDM4 injected TA muscle (FIG. 13).

Co-Localisation of Dystrophin and the DAP Complex in TA Muscles of Microdystrophin Treated CXMD Dog.

Dystrophin expression at the sarcolemma in normal muscle allows interactions with DAP complex to form a transmembrane link which acts as a mediator of signalling between extracellular matrix and cytoskeleton in muscle fibres. The ability of codon-optimised microdystrophins to restore the association of the dystrophin-associated protein (DAP) complex at the sarcolemma was investigated.

At eight week after intramuscular injection of $1\times10^{13}$ vg of AAV2/8-cMD1, cMD3 and cMD4 vectors into the muscle of CXMD, TA muscles were recovered and subjected to immunohistology for the dystrophin staining. Co-localisation of DAP complex such as α-dystrobrevin (Dtn) and α1-syntrophin (Syn) was observed at the cMD1, cMD3 and cMD4 positive fibres (FIG. 14).

Conclusion:

These in vivo data show that the microdystrophins are functional in mice (produced with AAV 2/9 vectors) but also in dogs (produced with AAV 2/8 vectors).

The invention claimed is:

1. An adeno-associated viral (AAV) vector comprising an expression construct, wherein:
the expression construct comprises a nucleic acid sequence which encodes a microdystrophin (MD);
the nucleic acid sequence encoding the MD has a size of at least 4.1 kb;
the expression construct has a size of less than 6 kb; and
the MD contains a partial or full-length C terminal domain of dystrophin.

2. The AAV vector according to claim 1, wherein the expression construct comprises two ITR sequences, and wherein the expression construct and the two ITR sequences together have a size of at least 5.1 kb.

3. The AAV vector according to claim 2, wherein the expression construct comprises two ITR sequences, and wherein the expression construct comprises or consists of the nucleic acid sequence of SEQ ID NO: 15 or SEQ ID NO: 18.

4. The AAV vector according to claim 2, wherein the expression construct has a size of at least 5.2 kb.

5. The AAV vector according to claim 2, wherein the expression construct has a size of at least 5.45 kb.

6. The AAV vector according to claim 1, wherein the AVV vector is an AAV vector of serotype 8 (AAV8) or 9 (AAV9).

7. The AAV vector according to claim 6, wherein the AAV vector is an AAV 2/8 or an AAV 2/9 vector.

8. The AAV vector according to claim 1, wherein the expression construct further comprises a muscle-specific promoter which is operably linked to the nucleic acid sequence encoding the MD.

9. The AAV vector according to claim 8, wherein the muscle-specific promoter is a Spc5-12 promoter.

10. The AAV vector according to claim 1, wherein said MD comprises or consists of the sequence of SEQ ID NO: 13 or SEQ ID NO: 16, or a variant thereof having at least 80% sequence identity thereto.

11. A composition comprising the AAV vector according to claim 1 and a pharmaceutically acceptable carrier.

12. A method for treating a subject with a dystrophic disease, comprising administering to the subject an effective amount of the composition of claim 11, thereby treating the dystrophic disease.

13. The method of claim 12, wherein the subject is a human.

14. The method of claim 13, wherein the dystrophic disease is Duchenne muscular dystrophy (DMD) or Becker muscular dystrophy (BMD).

15. The method of claim 12, wherein said MD comprises a central rod domain and a partial or full C-terminal domain, and wherein said MD has a deletion ΔR4-23 in the central rod domain and wherein the partial or full-length C terminal domain is encoded by exons 70 to 75, or exons 70 to 79, respectively.

16. The AAV vector according to claim 1, wherein said MD comprises or consists of the amino acid sequence of SEQ ID NO: 13 or SEQ ID NO: 16 or a variant thereof having at least 90% sequence identity thereto.

17. The AAV vector according to claim 16, wherein said MD comprises or consists of the sequence of SEQ ID NO: 13 or SEQ ID NO: 16.

18. An adeno-associated viral (AAV) vector comprising an expression construct, wherein:
the expression construct comprises a nucleic acid sequence which encodes a microdystrophin (MD);
the nucleic acid sequence encoding the MD has a size of at least 4.1 kb;
the MD contains a partial or full length C terminal domain of dystrophin, and
said MD comprises a central rod domain and has a deletion ΔR4-23 in the central rod domain and wherein the partial or full-length C terminal domain is encoded by exons 70 to 75 or exons 70 to 79, respectively.

19. A method for treating a subject with a dystrophic disease, comprising administering to the subject an effective amount of the composition of claim 18, thereby treating the dystrophic disease.

* * * * *